(12) United States Patent
Li

(10) Patent No.: US 9,719,100 B2
(45) Date of Patent: Aug. 1, 2017

(54) SOYBEAN ADF1 PROMOTER AND ITS USE IN CONSTITUTIVE EXPRESSION OF TRANSGENIC GENES IN PLANTS

(71) Applicant: E. I. DU PONT DE NEMOURS AND COMPANY, Wilmington, DE (US)

(72) Inventor: Zhongsen Li, Hockessin, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 265 days.

(21) Appl. No.: 14/418,291

(22) PCT Filed: Aug. 7, 2013

(86) PCT No.: PCT/US2013/053907
§ 371 (c)(1),
(2) Date: Jan. 29, 2015

(87) PCT Pub. No.: WO2014/025858
PCT Pub. Date: Feb. 13, 2014

(65) Prior Publication Data
US 2015/0184174 A1    Jul. 2, 2015

Related U.S. Application Data

(60) Provisional application No. 61/681,751, filed on Aug. 10, 2012.

(51) Int. Cl.
C12N 15/63    (2006.01)
C12N 15/82    (2006.01)

(52) U.S. Cl.
CPC ..... *C12N 15/8216* (2013.01); *C12N 15/8245* (2013.01); *C12N 15/8247* (2013.01); *C12N 15/8251* (2013.01); *C12N 15/8257* (2013.01); *C12N 15/8261* (2013.01); *C12N 15/8273* (2013.01); *C12N 15/8274* (2013.01); *C12N 15/8279* (2013.01); *C12N 15/8286* (2013.01)

(58) Field of Classification Search
None
See application file for complete search history.

(56) References Cited

PUBLICATIONS

GenBank Accession No. BT096470. Soybean clone JCVIFLGm-20D18. Published Aug. 6, 2009. pp. 1.*
Ponappa et al. Transient expression and stable transformation of soybean using the jellyfish green fluorescent protein. Plant Cell Reports. 1999. 19: pp. 6-12.*
Schmutz et al. Genome sequence of the paleopolyploid soybean. Nature. 2010/ 463(7278): 178-183.*
Ruzicka et al. The ancient subclasses of Arabidopsis Actin Depolymerizing Factor genes exhibit novel and differential expression. The Plant Journal. 2007. 52: 460-472.*

(Continued)

*Primary Examiner* — Ashley K Buran

(57) ABSTRACT

The invention relates to gene expression regulatory sequences from soybean, specifically to the promoter of a soybean actin depolymerizing factor gene and fragments thereof and their use in promoting the expression of one or more heterologous nucleic acid fragments in a constitutive manner in plants. The invention further discloses compositions, polynucleotide constructs, transformed host cells, transgenic plants and seeds containing the recombinant construct with the promoter, and methods for preparing and using the same.

17 Claims, 15 Drawing Sheets

(56)  References Cited

PUBLICATIONS

Figure 1:
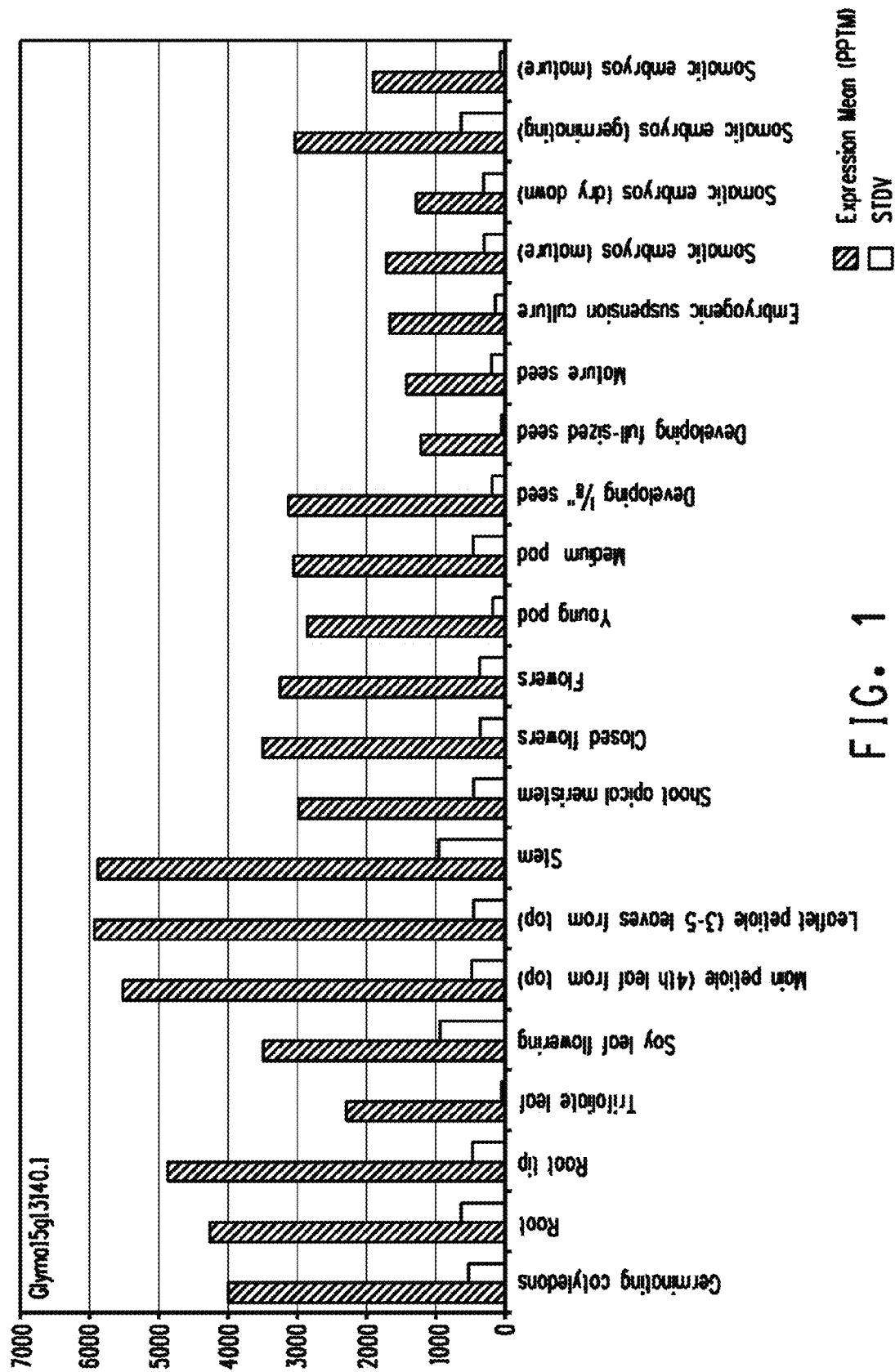

Young-Min Jeong et al., An upstream region in the first intron of petunia actin-depolymerizing factor 1 affects tissue-specific expression in transgenic Arabidopsis (Arabidopsis thaliana), The Plant Journal, 2007, pp. 230-239, vol. 2007.
Sutherland K Maciver et al., The ADF/cofilin family: actin-remodeling proteins, Genome Biology, 2002, p. 3007, vol. 3, No. 5.
Jeremy Schmutz et al., Genome sequence of the palaeopolyploid soybean, Nature, 2010, pp. 178-183, vol. 463, No. 7278.
Database Accession No. CG816032, Nov. 13, 2003, XP002715207.
Database Accession No. ED709374, Nov. 1, 2006, XP002715208.
Database Accession No. Al437585, Mar. 16, 1999, XP002715209.
Database Accession No. AZM60229, Oct. 27, 2011, XP002715210.
National Center for Biotechnology Information Accession No. NM_001249519, Dec. 4, 2015.
National Center for Biotechnology Information Accession No. XM_003534986, Nov. 8, 2011.
International Search Report for PCT/US2013/053907—mailed Nov. 13, 2013.

\* cited by examiner

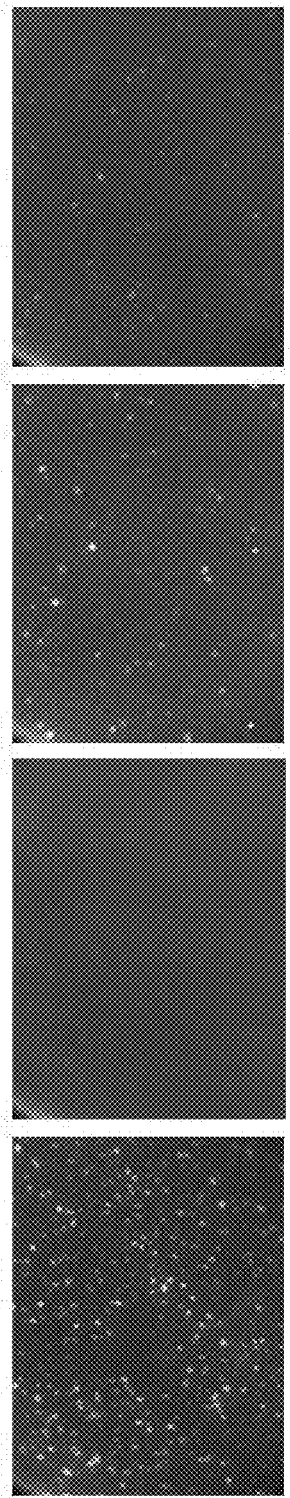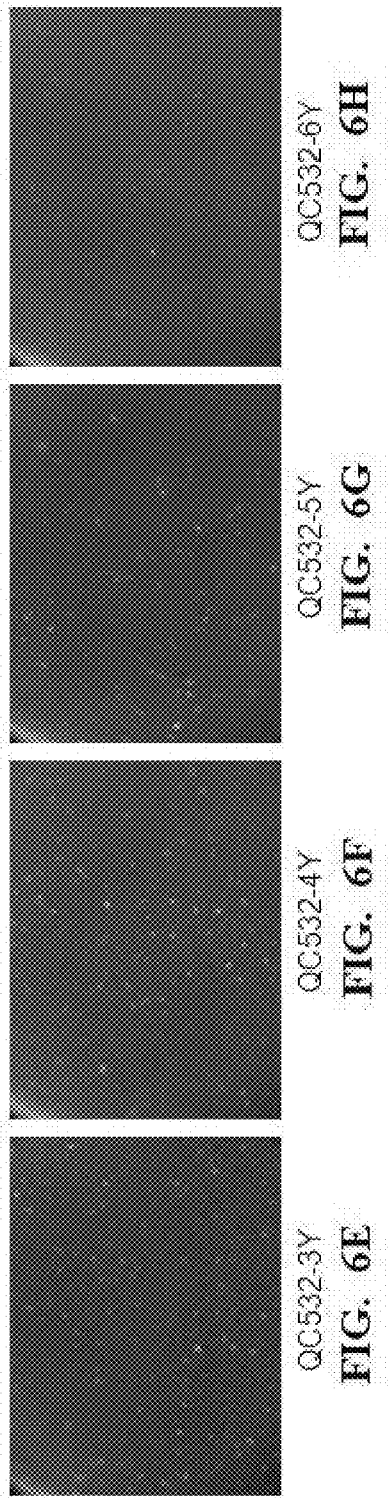

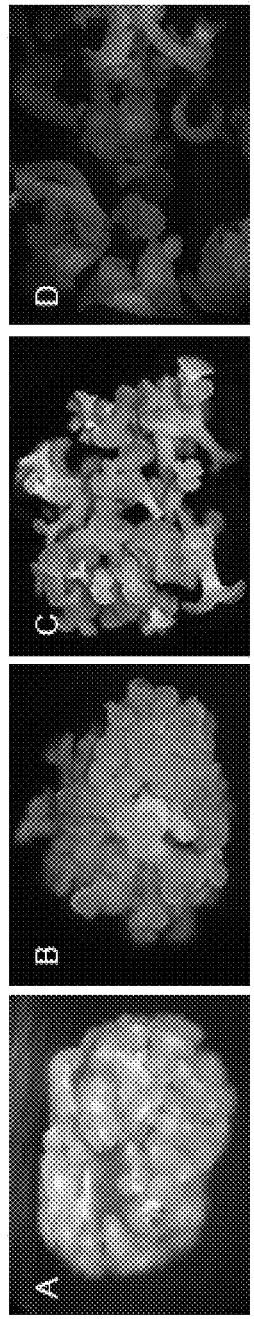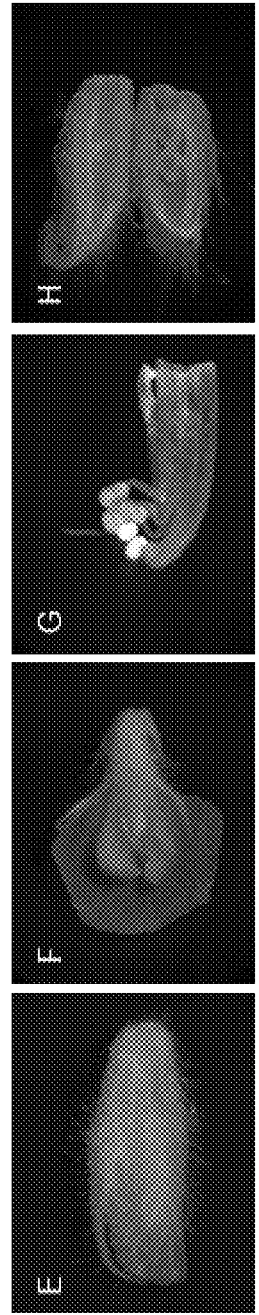

SEQUENCE LISTING

<160> NUMBER OF SEQ ID NOS: 44

<210> SEQ ID NO 1
<211> LENGTH: 1567
<212> TYPE: DNA
<213> ORGANISM: Glycine max

<400> SEQUENCE: 1

```
cccgggagtt cacatgctat gaatccgtta tcataaactc caaagccatg attacaacat      60
aaagagatgt tattaaaatt gaaataaata aaatttgagg cttaggtcct cgtgcacata     120
aacttgcatg atgatttaca gctctctctc ccactttgag tcttgtggta atttgaggta     180
aatattggat ccaactcagc aactactagt aagctttctc tcaaaagaaa aaaaaaacca     240
ctagtaagct ttattttcta gtgaagcaac tgctatagtc ttgggttttg gagaaattgt     300
caggtgtgcc attaaattaa gagttgcgtc gattatcctt acctttttta tataaaaaaa     360
tattccattt aattttgatt aaaatatata ttatttcacg acaaaaaaat actcgtgtag     420
attctattta tacaaatttg ctagattaag aaaattaaga atagacaaat tataatgtga     480
cataaatatt tctatgattg cttgaagtaa aatagcaaaa attagtttaa attgttttta     540
tataattcaa gtataaaatt gtcatatttt tctataaaag tgtcaacttt taatagaatg     600
tggttaaatg atgatttctc attgggtatc catgtaaaaa tattgttgtc attttatttg     660
tcatactttt acacaatttt tcatgatgtg atataattga taaataatct tatactttaa     720
gtataaaatt agagattgaa ttcccaaata taaaaataat attattgaga gagatcaact     780
tcttagataa atcttgatac ttcgagtagc accctgactt aaaaaatgtc cttggtaaat     840
ttttatttat taatatgatg cggttataaa gtaaattctt attagataat tgtgtaaaaa     900
ttcatctgtt ttttgtttaa gaatgtgtat atagttgatt aatttaatct atataataat     960
ttgtacggaa aaaatatact atttgggacc ctgagattat tatgtttggt agaaatttggg    1020 aggtgggaag attggatgtt aggtggaacg aggtcaggag acgacacatc tggtcgggga    1080
ggggaggtag aaaaattata cattgacaca ataggataat tggtacctag tgagataaaa    1140
ttttaaaaaa atatagatat tcatattata ggtattatga tttggtatga aagagaaaaa    1200
aagaagatga aaagtgttta aaaaataagt ttaatattta tgcattgaaa tcatgatgaa    1260
ttatgagtag atgtgtgttt aatgtccatc tatcatcttc acagtatggg acaacacaaa    1320
agcaatatga atgtgatgga ccacaattgg gccctcaagc cccaattcgg cccattgggc    1380
catcgaaaag aaaaagcatg cgctgcggat attaataatt ttgtgacgct ccaccacaat    1440
tccccatccc caaatttcct cattctccct ttcctctccg aaccctcgat cactctcacg    1500
cgctcctata ttcgctcctc caccgtcgct ctctcgaaca accacaacac catcttcatc    1560
accatgg                                                              1567
```

<210> SEQ ID NO 2
<211> LENGTH: 1559
<212> TYPE: DNA
<213> ORGANISM: Glycine max

<400> SEQUENCE: 2

```
gggagttcac atgctatgaa tccgttatca taaactccaa agccatgatt acaacataaa      60
gagatgttat taaaattgaa ataaataaaa tttgaggctt aggtcctcgt gcacataaac     120
ttgcatgatg atttacagct ctctctccca ctttgagtct tgtggtaatt tgaggtaaat     180
attggatcca actcagcaac tactagtaag ctttctctca aagaaaaaa aaaaccacta     240
```

```
gtaagcttta ttttctagtg aagcaactgc tatagtcttg ggttttggag aaattgtcag      300
gtgtgccatt aaattaagag ttgcgtcgat tatccttacc ttttttatat aaaaaaatat      360
tccatttaat tttgattaaa atatatatta tttcacgaca aaaaaatact cgtgtagatt      420
ctatttatac aaatttgcta gattaagaaa attaagaata gacaaattat aatgtgacat      480
aaatatttct atgattgctt gaagtaaaat agcaaaaatt agtttaaatt gttttatat       540 aattcaagta taaaattgtc atattttct  ataaagtgt  caacttttaa tagaatgtgg      600
ttaaatgatg atttctcatt gggtatccat gtaaaaatat tgttgtcatt ttatttgtca      660
tacttttaca caattttca  tgatgtgata taattgataa ataatcttat actttaagta      720
taaaattaga gattgaattc ccaaatataa aaataatatt attgagagag atcaacttct      780
tagataaatc ttgatacttc gagtagcacc ctgacttaaa aaatgtcctt ggtaaatttt      840
tatttattaa tatgatgcgg ttataaagta aattcttatt agataattgt gtaaaaattc      900
atctgttttt tgtttaagaa tgtgtatata gttgattaat ttaatctata taataatttg      960
tacggaaaaa atatactatt tgggaccctg agattattat gtttggtaga atttgggagg     1020
tgggaagatt ggatgttagg tggaacgagg tcaggagacg acacatctgg tcggggaggg     1080
gaggtagaaa aattatacat tgacacaata ggataattgg tacctagtga gataaaattt     1140
taaaaaaata tagatattca tattataggt attatgattt ggtatgaaag agaaaaaaag     1200
aagatgaaaa gtgtttaaaa aataagttta atatttatgc attgaaatca tgatgaatta     1260
tgagtagatg tgtgtttaat gtccatctat catcttcaca gtatgggaca acacaaaagc     1320
aatatgaatg tgatggacca caattgggcc ctcaagcccc aattcggccc attgggccat     1380
cgaaaagaaa aagcatgcgc tgcggatatt aataattttg tgacgctcca ccacaattcc     1440
ccatccccaa aatttctcat tctccctttc ctctccgaac cctcgatcac tctcacgcgc     1500
tcctatattc gctcctccac cgtcgctctc tcgaacaacc acaacaccat cttcatcac      1559
```

<210> SEQ ID NO 3
<211> LENGTH: 1243
<212> TYPE: DNA
<213> ORGANISM: Glycine max

<400> SEQUENCE: 3

```
agagttgcgt cgattatcct tacctttttt atataaaaaa atattccatt taattttgat       60
taaaatatat attatttcac gacaaaaaaa tactcgtgta gattctattt atacaaattt      120
gctagattaa gaaaattaag aatagacaaa ttataatgtg acataaatat ttctatgatt      180
gcttgaagta aaatagcaaa aattagttta aattgttttt ataattca   agtataaaat      240 tgtcatattt ttctataaaa gtgtcaactt ttaatagaat gtggttaaat gatgatttct      300
cattgggtat ccatgtaaaa atattgttgt cattttattt gtcatacttt tacacaattt      360
ttcatgatgt gatataattg ataaataatc ttatacttta agtataaaat tagagattga      420
attcccaaat ataaaaataa tattattgag agagatcaac ttcttagata aatcttgata      480
cttcgagtag caccctgact taaaaaatgt ccttggtaaa ttttattta ttaatatgat       540 gcggttataa agtaaattct tattagataa ttgtgtaaaa attcatctgt ttttgttta      600 agaatgtgta tatagttgat taatttaatc tatataataa tttgtacgga aaaatatac      660 tatttgggac cctgagatta ttatgtttgg tagaatttgg gaggtgggaa gattggatgt      720
taggtggaac gaggtcagga gacgacacat ctggtcgggg aggggaggta gaaaaattat      780
```

| | |
|---|---|
| acattgacac aataggataa ttggtaccta gtgagataaa attttaaaaa aatatagata | 840 |
| ttcatattat aggtattatg atttggtatg aaagagaaaa aaagaagatg aaaagtgttt | 900 |
| aaaaaataag tttaatattt atgcattgaa atcatgatga attatgagta gatgtgtgtt | 960 |
| taatgtccat ctatcatctt cacagtatgg gacaacacaa aagcaatatg aatgtgatgg | 1020 |
| accacaattg ggccctcaag ccccaattcg gcccattggg ccatcgaaaa gaaaaagcat | 1080 |
| gcgctgcgga tattaataat tttgtgacgc tccaccacaa ttccccatcc ccaaaatttc | 1140 |
| tcattctccc tttcctctcc gaaccctcga tcactctcac gcgctcctat attcgctcct | 1200 |
| ccaccgtcgc tctctcgaac aaccacaaca ccatcttcat cac | 1243 |

<210> SEQ ID NO 4
<211> LENGTH: 985
<212> TYPE: DNA
<213> ORGANISM: Glycine max

<400> SEQUENCE: 4

| | |
|---|---|
| aagtgtcaac ttttaataga atgtggttaa atgatgattt ctcattgggt atccatgtaa | 60 |
| aaatattgtt gtcattttat ttgtcatact tttacacaat ttttcatgat gtgatataat | 120 |
| tgataaaataa tcttatactt taagtataaa attagagatt gaattcccaa atataaaaat | 180 |
| aatattattg agagagatca acttcttaga taaatcttga tacttcgagt agcaccctga | 240 |
| cttaaaaaat gtccttggta aattttatt tattaatatg atgcggttat aaagtaaatt | 300 |
| cttattagat aattgtgtaa aaattcatct gttttttgtt taagaatgtg tatatagttg | 360 |
| attaattttaa tctatataat aatttgtacg gaaaaaatat actatttggg accctgagat | 420 |
| tattatgttt ggtagaattt gggaggtggg aagattggat gttaggtgga acgaggtcag | 480 |
| gagacgacac atctggtcgg ggaggggagg tagaaaaatt atacattgac acaataggat | 540 |
| aattggtacc tagtgagata aaatttttaaa aaaatataga tattcatatt ataggtatta | 600 |
| tgatttggta tgaaagagaa aaaagaagaa tgaaagtgt ttaaaaaata gtttaatat | 660 |
| ttatgcattg aaatcatgat gaattatgag tagatgtgtg tttaatgtcc atctatcatc | 720 |
| ttcacagtat gggacaacac aaaagcaata tgaatgtgat ggaccacaat tgggccctca | 780 |
| agccccaatt cggcccattg gccatcgaa agaaaaagc atgcgctgcg gatattaata | 840 |
| attttgtgac gctccaccac aattccccat ccccaaaatt tctcattctc cctttcctct | 900 |
| ccgaaccctc gatcactctc acgcgctcct atattcgctc ctccaccgtc gctctctcga | 960 |
| acaaccacaa caccatcttc atcac | 985 |

<210> SEQ ID NO 5
<211> LENGTH: 770
<212> TYPE: DNA
<213> ORGANISM: Glycine max

<400> SEQUENCE: 5

| | |
|---|---|
| cttgatactt cgagtagcac cctgacttaa aaaatgtcct tggtaaattt ttatttatta | 60 |
| atatgatgcg gttataaagt aaattcttat tagataattg tgtaaaaatt catctgtttt | 120 |
| ttgtttaaga atgtgtatat agttgattaa tttaatctat ataataattt gtacggaaaa | 180 |
| aatatactat ttgggaccct gagattatta tgtttggtag aatttgggag gtgggaagat | 240 |
| tggatgttag gtggaacgag gtcaggagac gacacatctg gtcggggagg ggaggtagaa | 300 |
| aaattataca ttgacacaat aggataattg gtacctagtg agataaaatt ttaaaaaaat | 360 |
| atagatattc atattatagg tattatgatt tggtatgaaa gagaaaaaaa gaagatgaaa | 420 |

```
agtgtttaaa aaataagttt aatatttatg cattgaaatc atgatgaatt atgagtagat    480
gtgtgtttaa tgtccatcta tcatcttcac agtatgggac aacacaaaag caatatgaat    540
gtgatggacc acaattgggc cctcaagccc caattcggcc cattgggcca tcgaaaagaa    600
aaagcatgcg ctgcggatat taataatttt gtgacgctcc accacaattc cccatcccca    660
aaatttctca ttctcccttt cctctccgaa ccctcgatca ctctcacgcg ctcctatatt    720
cgctcctcca ccgtcgctct ctcgaacaac cacaacacca tcttcatcac                770

<210> SEQ ID NO 6
<211> LENGTH: 458
<212> TYPE: DNA
<213> ORGANISM: Glycine max

<400> SEQUENCE: 6
gacacaatag gataattggt acctagtgag ataaaatttt aaaaaaatat agatattcat     60
attataggta ttatgatttg gtatgaaaga gaaaaaaaga agatgaaaag tgtttaaaaa    120
ataagtttaa tatttatgca ttgaaatcat gatgaattat gagtagatgt gtgtttaatg    180
tccatctatc atcttcacag tatgggacaa cacaaaagca atatgaatgt gatggaccac    240
aattgggccc tcaagcccca attcggccca ttgggccatc gaaaagaaaa agcatgcgct    300
gcggatatta ataattttgt gacgctccac cacaattccc catccccaaa atttctcatt    360
ctccctttcc tctccgaacc ctcgatcact ctcacgcgct cctatattcg ctcctccacc    420
gtcgctctct cgaacaacca acaccatc ttcatcac                              458

<210> SEQ ID NO 7
<211> LENGTH: 212
<212> TYPE: DNA
<213> ORGANISM: Glycine max

<400> SEQUENCE: 7
gccctcaagc cccaattcgg cccattgggc catcgaaaag aaaaagcatg cgctgcggat     60
attaataatt ttgtgacgct ccaccacaat tccccatccc caaatttct cattctccct    120 ttcctctccg aaccctcgat cactctcacg cgctcctata ttcgctcctc caccgtcgct    180
ctctcgaaca accacaacac catcttcatc ac                                  212

<210> SEQ ID NO 8
<211> LENGTH: 34
<212> TYPE: DNA
<213> ORGANISM: Artificial Sequence
<220> FEATURE:
<223> OTHER INFORMATION: primer, PSO315053Xma

<400> SEQUENCE: 8
taactaaccc gggagttcac atgctatgaa tccg                                 34

<210> SEQ ID NO 9
<211> LENGTH: 33
<212> TYPE: DNA
<213> ORGANISM: Artificial Sequence
<220> FEATURE:
<223> OTHER INFORMATION: primer, PSO315053Nco

<400> SEQUENCE: 9
tgaatgacca tggtgatgaa gatggtgttg tgg                                  33

<210> SEQ ID NO 10
```

```
<211> LENGTH: 21
<212> TYPE: DNA
<213> ORGANISM: Artificial Sequence
<220> FEATURE:
<223> OTHER INFORMATION: primer, QC532-A

<400> SEQUENCE: 10
gtgatgaaga tggtgttgtg g                                            21

<210> SEQ ID NO 11
<211> LENGTH: 24
<212> TYPE: DNA
<213> ORGANISM: Artificial Sequence
<220> FEATURE:
<223> OTHER INFORMATION: primer, QC532-S1

<400> SEQUENCE: 11
gggagttcac atgctatgaa tccg                                         24

<210> SEQ ID NO 12
<211> LENGTH: 24
<212> TYPE: DNA
<213> ORGANISM: Artificial Sequence
<220> FEATURE:
<223> OTHER INFORMATION: primer, QC532-S2

<400> SEQUENCE: 12
agagttgcgt cgattatcct tacc                                         24

<210> SEQ ID NO 13
<211> LENGTH: 28
<212> TYPE: DNA
<213> ORGANISM: Artificial Sequence
<220> FEATURE:
<223> OTHER INFORMATION: primer, QC532-S3

<400> SEQUENCE: 13
aagtgtcaac ttttaataga atgtggtt                                     28

<210> SEQ ID NO 14
<211> LENGTH: 26
<212> TYPE: DNA
<213> ORGANISM: Artificial Sequence
<220> FEATURE:
<223> OTHER INFORMATION: primer, QC532-S4

<400> SEQUENCE: 14
cttgatactt cgagtagcac cctgac                                       26

<210> SEQ ID NO 15
<211> LENGTH: 30
<212> TYPE: DNA
<213> ORGANISM: Artificial Sequence
<220> FEATURE:
<223> OTHER INFORMATION: primer, QC532-S5

<400> SEQUENCE: 15
gacacaatag gataattggt acctagtgag                                   30

<210> SEQ ID NO 16
<211> LENGTH: 19
<212> TYPE: DNA
<213> ORGANISM: Artificial Sequence
<220> FEATURE:
<223> OTHER INFORMATION: primer, QC532-S6

<400> SEQUENCE: 16
```

```
gccctcaagc cccaattcg                                              19
```

<210> SEQ ID NO 17
<211> LENGTH: 1084
<212> TYPE: DNA
<213> ORGANISM: Glycine max

<400> SEQUENCE: 17

```
cgagcacaat tccccacgag caaaatttct cattctccct ttcctctccg aaccctcgat    60
cactctcacg cgctcctata ttcgctcctc caccgtcgct ctctcgaaca accacaacac   120
catcttcatc acatggcaaa cgcagcatct ggtatggcag tccatgatga ctgcaagttg   180
aggttttgg agctgaaggc aaaaaggaca caccgtttca tagttttaa gattgaggag     240
cagcagaagc aggtcattgt ggagaagctt ggtgagcctg cccagggcta tgaagatttc   300
actgccagcc ttcctgctga cgagtgccgt tatgctgttt atgattttga gtatctgact   360
gaagggaatg tccctaaaag cagaattttt ttcattgcgt ggtcccctga cacatcaagg   420
gtgaggagca agatgattta tgcaagctcc aaagacagat caagaggga gctggatgga   480
attcaagtag agttgcaagc aactgatcct actgagatgg tcttgatgt gttcaaaagc    540
cgtgccaact aaaatgatta tataaaatag taggctttct ggtgggagca gcacccctga   600
agccttagtt actcatatgg aaaatatcct agtttgtggg atggtcaact tgggtagtta   660
tggtcccaaa ctctcaattt tccaagttgt ggcataaaat tctattgcac cttttgacaa   720
gctttgcttg ttccagtgtg ttttattatg atttgtgatt tatacaacct ttgcgtttga   780
gtgccatttt agtcgtctta tcccttacta gttgaatttg taactgtttt gtgttatcag   840
acaaaaaatg ggggttcttc acttattgac actcgtcatc cactaatgct tgtgacttc    900
ttttggccga tatatgcttt cttttgtatg agcatacaaa ggcctcttgt ttgctatatt   960
cctttttgt tttatgtttt gggagaatga gatttattca attggttggg tgttcttact   1020
tgaaaccaga gtatacttaa ttcatagcaa tagcacataa gcgacttgtc atgctttatg   1080
gtac                                                              1084
```

<210> SEQ ID NO 18
<211> LENGTH: 139
<212> TYPE: PRT
<213> ORGANISM: Glycine max

<400> SEQUENCE: 18

```
Met Ala Asn Ala Ala Ser Gly Met Ala Val His Asp Asp Cys Lys Leu
1               5                   10                  15
Arg Phe Leu Glu Leu Lys Ala Lys Arg Thr His Arg Phe Ile Val Phe
            20                  25                  30
Lys Ile Glu Glu Gln Gln Lys Gln Val Ile Val Glu Lys Leu Gly Glu
        35                  40                  45
Pro Ala Gln Gly Tyr Glu Asp Phe Thr Ala Ser Leu Pro Ala Asp Glu
    50                  55                  60
Cys Arg Tyr Ala Val Tyr Asp Phe Glu Tyr Leu Thr Glu Gly Asn Val
65                  70                  75                  80
Pro Lys Ser Arg Ile Phe Phe Ile Ala Trp Ser Pro Asp Thr Ser Arg
                85                  90                  95
Val Arg Ser Lys Met Ile Tyr Ala Ser Ser Lys Asp Arg Phe Lys Arg
            100                 105                 110
Glu Leu Asp Gly Ile Gln Val Glu Leu Gln Ala Thr Asp Pro Thr Glu
```

```
            115                 120                 125
Met Gly Leu Asp Val Phe Lys Ser Arg Ala Asn
    130                 135

<210> SEQ ID NO 19
<211> LENGTH: 4844
<212> TYPE: DNA
<213> ORGANISM: Artificial Sequence
<220> FEATURE:
<223> OTHER INFORMATION: plasmid QC532

<400> SEQUENCE: 19
cccgggagtt cacatgctat gaatccgtta tcataaactc caaagccatg attacaacat      60
aaagagatgt tattaaaatt gaaataaata aaatttgagg cttaggtcct cgtgcacata     120
aacttgcatg atgatttaca gctctctctc ccactttgag tcttgtggta atttgaggta     180
aatattggat ccaactcagc aactactagt aagctttctc tcaaaagaaa aaaaaaacca     240
ctagtaagct ttatttttcta gtgaagcaac tgctatagtc ttgggttttg gagaaattgt     300
caggtgtgcc attaaattaa gagttgcgtc gattatcctt accttttta tataaaaaaa      360
tattccattt aattttgatt aaaatatata ttatttcacg acaaaaaaat actcgtgtag     420
attctatttta tacaaatttg ctagattaag aaaattaaga atagacaaat tataatgtga     480
cataaatatt tctatgattg cttgaagtaa aatagcaaaa attagtttaa attgttttta     540
tataattcaa gtataaaatt gtcatatttt tctataaaag tgtcaacttt taatagaatg     600
tggttaaatg atgatttctc attgggtatc catgtaaaaa tattgttgtc attttatttg     660
tcatactttt acacaatttt tcatgatgtg atataattga taaataatct tatactttaa     720
gtataaaatt agagattgaa ttcccaaata taaaaataat attattgaga gagatcaact     780
tcttagataa atcttgatac ttcgagtagc accctgactt aaaaaatgtc cttggtaaat     840
ttttatttat taatatgatg cggttataaa gtaaattctt attagataat tgtgtaaaaa     900
ttcatctgtt ttttgtttaa gaatgtgtat atagttgatt aatttaatct atataataat     960
ttgtacggaa aaaatatact atttgggacc ctgagattat tatgtttggt agaatttggg    1020
aggtgggaag attggatgtt aggtggaacg aggtcaggag acgacacatc tggtcgggga    1080
ggggaggtag aaaaattata cattgacaca ataggataat tggtacctag tgagataaaa    1140
ttttaaaaaa atatagatat tcatattata ggtattatga tttggtatga agagaaaaa     1200
aagaagatga aaagtgttta aaaaataagt ttaatattta tgcattgaaa tcatgatgaa    1260
ttatgagtag atgtgtgttt aatgtccatc tatcatcttc acagtatggg acaacacaaa    1320
agcaatatga atgtgatgga ccacaattgg gccctcaagc cccaattcgg cccattgggc    1380
catcgaaaag aaaaagcatg cgctgcggat attaataatt ttgtgacgct ccaccacaat    1440
tccccatccc caaatttct cattctccct ttcctctccg aaccctcgat cactctcacg    1500
cgctcctata ttcgctcctc caccgtcgct ctctcgaaca accacaacac catcttcatc    1560
accatggccc acagcaagca cggcctgaag gaggagatga ccatgaagta ccacatggag    1620
ggctgcgtga acggccacaa gttcgtgatc accggcgagg gcatcggcta cccccttcaag    1680
ggcaagcaga ccatcaacct gtgcgtgatc gagggcggcc ccctgccctt cagcgaggac    1740
atcctgagcg ccggcttcaa gtacggcgac cggatcttca ccgagtaccc ccaggacatc    1800
gtggactact tcaagaacag ctgccccgcc ggctacacct ggggccggag cttcctgttc    1860
gaggacggcg ccgtgtgcat ctgtaacgtg gacatcaccg tgagcgtgaa ggagaactgc    1920
```

```
atctaccaca agagcatctt caacggcgtg aacttccccg ccgacggccc cgtgatgaag    1980
aagatgacca ccaactggga ggccagctgc gagaagatca tgcccgtgcc taagcagggc    2040
atcctgaagg gcgacgtgag catgtacctg ctgctgaagg acggcggccg gtaccggtgc    2100
cagttcgaca ccgtgtacaa ggccaagagc gtgcccagca agatgcccga gtggcacttc    2160
atccagcaca agctgctgcg ggaggaccgg agcgacgcca agaaccagaa gtggcagctg    2220
accgagcacg ccatcgcctt ccccagcgcc ctggcctgag agctcgaatt tccccgatcg    2280
ttcaaacatt tggcaataaa gtttcttaag attgaatcct gttgccggtc ttgcgatgat    2340
tatcatataa tttctgttga attacgttaa gcatgtaata attaacatgt aatgcatgac    2400
gttatttatg agatgggttt ttatgattag agtcccgcaa ttatacattt aatacgcgat    2460
agaaaacaaa atatagcgcg caaactagga taaattatcg cgcgcggtgt catctatgtt    2520
actagatcgg gaattctagt ggccggccca gctgatatcc atcacactgg cggccgcact    2580
cgactgaatt ggttccggcg ccagcctgct tttttgtaca aagttggcat tataaaaaag    2640
cattgcttat caatttgttg caacgaacag gtcactatca gtcaaaataa aatcattatt    2700
tggggcccga gcttaagtaa ctaactaaca ggaagagttt gtagaaacgc aaaaaggcca    2760
tccgtcagga tggccttctg cttagtttga tgcctggcag tttatggcgg gcgtcctgcc    2820
cgccaccctc cgggccgttg cttcacaacg ttcaaatccg ctcccggcgg atttgtccta    2880
ctcaggagag cgttcaccga caaacaacag ataaaacgaa aggcccagtc ttccgactga    2940
gcctttcgtt ttatttgatg cctggcagtt ccctactctc gcttagtagt tagacgtccc    3000
cgagatccat gctagcggta atacggttat ccacagaatc aggggataac gcaggaaaga    3060
acatgtgagc aaaaggccag caaaaggcca ggaaccgtaa aaaggccgcg ttgctggcgt    3120
ttttccatag gctccgcccc cctgacgagc atcacaaaaa tcgacgctca agtcagaggt    3180
ggcgaaaccc gacaggacta taaagatacc aggcgtttcc ccctggaagc tccctcgtgc    3240
gctctcctgt tccgaccctg ccgcttaccg gatacctgtc cgcctttctc ccttcgggaa    3300
gcgtggcgct ttctcatagc tcacgctgta ggtatctcag ttcggtgtag gtcgttcgct    3360
ccaagctggg ctgtgtgcac gaaccccccg ttcagcccga ccgctgcgcc ttatccggta    3420
actatcgtct tgagtccaac ccggtaagac acgacttatc gccactggca gcagccactg    3480
gtaacaggat tagcagagcg aggtatgtag gcggtgctac agagttcttg aagtggtggc    3540
ctaactacgg ctacactaga agaacagtat ttggtatctg cgctctgctg aagccagtta    3600
ccttcggaaa aagagttggt agctcttgat ccggcaaaca aaccaccgct ggtagcggtg    3660
gtttttttgt ttgcaagcag cagattacgc gcagaaaaaa aggatctcaa gaagatcctt    3720
tgatcttttc tacggggtct gacgctcagt ggaacgggc ccaatctgaa taatgttaca    3780
accaattaac caattctgat tagaaaaact catcgagcat caaatgaaac tgcaatttat    3840
tcatatcagg attatcaata ccatattttt gaaaaagccg tttctgtaat gaaggagaaa    3900
actcaccgag gcagttccat aggatggcaa gatcctggta tcggtctgcg attccgactc    3960
gtccaacatc aatacaacct attaatttcc cctcgtcaaa aataaggtta tcaagtgaga    4020
aatcaccatg agtgacgact gaatccggtg agaatggcaa aagtttatgc atttctttcc    4080
agacttgttc aacaggccag ccattacgct cgtcatcaaa atcactcgca tcaaccaaac    4140
cgttattcat tcgtgattgc gcctgagcga gacgaaatac gcgatcgctg ttaaaaggac    4200
aattacaaac aggaatcgaa tgcaaccggc gcaggaacac tgccagcgca tcaacaatat    4260
tttcacctga atcaggatat tcttctaata cctggaatgc tgttttcccg gggatcgcag    4320
```

-continued

```
tggtgagtaa ccatgcatca tcaggagtac ggataaaatg cttgatggtc ggaagaggca    4380
taaattccgt cagccagttt agtctgacca tctcatctgt aacatcattg gcaacgctac    4440
ctttgccatg tttcagaaac aactctggcg catcgggctt cccatacaag cgatagattg    4500
tcgcacctga ttgcccgaca ttatcgcgag cccatttata cccatataaa tcagcatcca    4560
tgttggaatt taatcgcggc ctcgacgttt cccgttgaat atggctcata acacccttg     4620 tattactgtt tatgtaagca gacagtttta ttgttcatga tgatatattt ttatcttgtg    4680
caatgtaaca tcagagattt tgagacacgg gccagagctg cagctggatg caaataatg     4740 atttatttt gactgatagt gacctgttcg ttgcaacaaa ttgataagca atgctttctt     4800
ataatgccaa ctttgtacaa gaaagctggg tctagatatc tcga                    4844
```

<210> SEQ ID NO 20
<211> LENGTH: 4910
<212> TYPE: DNA
<213> ORGANISM: Artificial Sequence
<220> FEATURE:
<223> OTHER INFORMATION: plasmid QC635

<400> SEQUENCE: 20

```
cccgggagtt cacatgctat gaatccgtta tcataaactc caaagccatg attacaacat      60
aaagagatgt tattaaaatt gaaataaata aaatttgagg cttaggtcct cgtgcacata     120
aacttgcatg atgatttaca gctctctctc ccactttgag tcttgtggta atttgaggta     180
aatattggat ccaactcagc aactactagt aagctttctc tcaaaagaaa aaaaaaacca     240
ctagtaagct ttattttcta gtgaagcaac tgctatagtc ttgggttttg gagaaattgt     300
caggtgtgcc attaaattaa gagttgcgtc gattatcctt accttttta tataaaaaa      360 tattccattt aattttgatt aaaatatata ttatttcacg acaaaaaaat actcgtgtag     420
attctattta tacaaatttg ctagattaag aaaattaaga atagacaaat tataatgtga     480
cataaatatt tctatgattg cttgaagtaa aatagcaaaa attagtttaa attgttttta     540
tataattcaa gtataaaatt gtcatatttt tctataaaag tgtcaacttt taatagaatg     600
tggttaaatg atgattctc attgggtatc catgtaaaaa tattgttgtc atttatttg      660 tcatactttt acacaatttt tcatgatgtg atataattga taaataatct tatactttaa    720
gtataaaatt agagattgaa ttcccaaata taaaaataat attattgaga gagatcaact    780
tcttagataa atcttgatac ttcgagtagc accctgactt aaaaaatgtc cttggtaaat    840
ttttatttat taatatgatg cggttataaa gtaaattctt attagataat tgtgtaaaaa    900
ttcatctgtt ttttgtttaa gaatgtgtat atagttgatt aatttaatct atataataat    960
ttgtacggaa aaaatatact atttgggacc ctgagattat tatgtttggt agaatttggg   1020
aggtgggaag attggatgtt aggtggaacg aggtcaggag acgacacatc tggtcgggga   1080
ggggaggtag aaaaattata cattgacaca ataggataat tggtacctag tgagataaaa   1140
ttttaaaaaa atatagatat tcatattata ggtattatga tttggtatga agagaaaaa    1200 aagaagatga aaagtgttta aaaaataagt ttaatattta tgcattgaaa tcatgatgaa   1260
ttatgagtag atgtgtgttt aatgtccatc tatcatcttc acagtatggg acaacacaaa   1320
agcaatatga atgtgatgga ccacaattgg gccctcaagc cccaattcgg cccattgggc   1380
catcgaaaag aaaaagcatg cgctgcggat attaataatt ttgtgacgct ccaccacaat   1440
tccccatccc caaatttct cattctccct ttcctctccg aaccctcgat cactctcacg   1500
```

```
cgctcctata ttcgctcctc caccgtcgct ctctcgaaca accacaacac catcttcatc    1560
accatggccc agtccaagca cggcctgacc aaggagatga ccatgaagta ccgcatggag    1620
ggctgcgtgg acggccacaa gttcgtgatc accggcgagg gcatcggcta ccccttcaag    1680
ggcaagcagg ccatcaacct gtgcgtggtg gagggcggcc ccttgccctt cgccgaggac    1740
atcttgtccg ccgccttcat gtacggcaac cgcgtgttca ccgagtaccc ccaggacatc    1800
gtcgactact tcaagaactc ctgccccgcc ggctacacct gggaccgctc cttcctgttc    1860
gaggacggcg ccgtgtgcat ctgcaacgcc gacatcaccg tgagcgtgga ggagaactgc    1920
atgtaccacg agtccaagtt ctacggcgtg aacttccccg ccgacggccc cgtgatgaag    1980
aagatgaccg acaactggga gccctcctgc gagaagatca tccccgtgcc caagcagggc    2040
atcttgaagg cgacgtgag catgtacctg ctgctgaagg acggtggccg cttgcgctgc    2100
cagttcgaca ccgtgtacaa ggccaagtcc gtgccccgca agatgcccga ctggcacttc    2160
atccagcaca agctgacccg cgaggaccgc agcgacgcca agaaccagaa gtggcacctg    2220
accgagcacg ccatcgcctc cggctccgcc ttgccctccg gactcagatc tcgactagag    2280
tcgaacctag acttgtccat cttctggatt ggccaactta attaatgtat gaaataaaag    2340
gatgcacaca tagtgacatg ctaatcacta taatgtgggc atcaaagttg tgtgttatgt    2400
gtaattacta gttatctgaa taaaagagaa agagatcatc catatttctt atcctaaatg    2460
aatgtcacgt gtctttataa ttctttgatg aaccagatgc atttcattaa ccaaatccat    2520
atacatataa atattaatca tatataatta atatcaattg ggttagcaaa acaaatctag    2580
tctaggtgtg ttttgcgaat tctagtggcc ggcccagctg atatccatca cactggcggc    2640
cgcactcgac tgaattggtt ccggcgccag cctgcttttt tgtacaaagt tggcattata    2700
aaaaagcatt gcttatcaat ttgttgcaac gaacaggtca ctatcagtca aaataaaatc    2760
attatttggg gcccgagctt aagtaactaa ctaacaggaa gagtttgtag aaacgcaaaa    2820
aggccatccg tcaggatggc cttctgctta gtttgatgcc tggcagttta tggcgggcgt    2880
cctgcccgcc accctccggg ccgttgcttc acaacgttca aatccgctcc cggcggattt    2940
gtcctactca ggagagcgtt caccgacaaa caacagataa aacgaaaggc ccagtcttcc    3000
gactgagcct ttcgttttat ttgatgcctg gcagttccct actctcgctt agtagttaga    3060
cgtccccgag atccatgcta gcggtaatac ggttatccac agaatcaggg gataacgcag    3120
gaaagaacat gtgagcaaaa ggccagcaaa aggccaggaa ccgtaaaaag gccgcgttgc    3180
tggcgttttt ccataggctc cgcccccctg acgagcatca caaaaatcga cgctcaagtc    3240
agaggtggcg aaacccgaca ggactataaa gataccaggc gtttccccct ggaagctccc    3300
tcgtgcgctc tcctgttccg accctgccgc ttaccggata cctgtccgcc tttctccctt    3360
cgggaagcgt ggcgctttct catagctcac gctgtaggta tctcagttcg gtgtaggtcg    3420
ttcgctccaa gctgggctgt gtgcacgaac cccccgttca gcccgaccgc tgcgccttat    3480
ccggtaacta tcgtcttgag tccaacccgg taagacacga cttatcgcca ctggcagcag    3540
ccactggtaa caggattagc agagcgaggt atgtaggcgg tgctacagag ttcttgaagt    3600
ggtggcctaa ctacggctac actagaagaa cagtatttgg tatctgcgct ctgctgaagc    3660
cagttacctt cggaaaaaga gttggtagct cttgatccgg caaacaaacc accgctggta    3720
gcggtggttt ttttgtttgc aagcagcaga ttacgcgcag aaaaaaagga tctcaagaag    3780
atcctttgat cttttctacg gggtctgacg ctcagtggaa cggggcccaa tctgaataat    3840
gttacaacca attaaccaat tctgattaga aaaactcatc gagcatcaaa tgaaactgca    3900
```

```
atttattcat atcaggatta tcaataccat attttttgaaa aagccgtttc tgtaatgaag      3960
gagaaaactc accgaggcag ttccatagga tggcaagatc ctggtatcgg tctgcgattc      4020
cgactcgtcc aacatcaata caacctatta atttcccctc gtcaaaaata aggttatcaa      4080
gtgagaaatc accatgagtg acgactgaat ccggtgagaa tggcaaaagt ttatgcattt      4140
ctttccagac ttgttcaaca ggccagccat tacgctcgtc atcaaaatca ctcgcatcaa      4200
ccaaaccgtt attcattcgt gattgcgcct gagcgagacg aaatacgcga tcgctgttaa      4260
aaggacaatt acaaacagga atcgaatgca accggcgcag gaacactgcc agcgcatcaa      4320
caatattttc acctgaatca ggatattctt ctaatacctg gaatgctgtt tttccgggga      4380
tcgcagtggt gagtaaccat gcatcatcag gagtacggat aaaatgcttg atggtcggaa      4440
gaggcataaa ttccgtcagc cagtttagtc tgaccatctc atctgtaaca tcattggcaa      4500
cgctaccttt gccatgtttc agaaacaact ctggcgcatc gggcttccca tacaagcgat      4560
agattgtcgc acctgattgc ccgacattat cgcgagccca tttataccca tataaatcag      4620
catccatgtt ggaatttaat cgcggcctcg acgtttcccg ttgaatatgg ctcataacac      4680
cccttgtatt actgtttatg taagcagaca gttttattgt tcatgatgat atatttttat      4740
cttgtgcaat gtaacatcag agattttgag acacgggcca gagctgcagc tggatggcaa      4800
ataatgattt tattttgact gatagtgacc tgttcgttgc aacaaattga taagcaatgc      4860
tttcttataa tgccaacttt gtacaagaaa gctgggtcta gatatctcga                 4910

<210> SEQ ID NO 21
<211> LENGTH: 8482
<212> TYPE: DNA
<213> ORGANISM: Artificial Sequence
<220> FEATURE:
<223> OTHER INFORMATION: plasmid QC478i

<400> SEQUENCE: 21
atcgaaccac tttgtacaag aaagctgaac gagaaacgta aaatgatata aatatcaata       60
tattaaatta gattttgcat aaaaaacaga ctacataata ctgtaaaaca caacatatcc      120
agtcactatg gtcgacctgc agactggctg tgtataaggg agcctgacat ttatattccc      180
cagaacatca ggttaatggc gtttttgatg tcatttttcgc ggtggctgag atcagccact      240
tcttccccga taacggagac cggcacactg gccatatcgg tggtcatcat cgcgccagctt     300 tcatccccga tatgcaccac cgggtaaagt tcacggggga ctttatctga cagcagacgt      360
gcactggcca gggggatcac catccgtcgc ccgggcgtgt caataatatc actctgtaca      420
tccacaaaca gacgataacg gctctctctt ttataggtgt aaaccttaaa ctgcatttca      480
ccagcccctg ttctcgtcag caaaagagcc gttcatttca ataaaccggg cgacctcagc      540
catcccttcc tgattttccg ctttccagcg ttcggcacgc agacgacggg cttcattctg      600
catggttgtg cttaccagac cggagatatt gacatcatat atgccttgag caactgatag      660
ctgtcgctgt caactgtcac tgtaatacgc tgcttcatag catacctctt tttgacatac      720
ttcgggtata catatcagta tatattctta taccgcaaaa atcagcgcgc aaatacgcat      780
actgttatct ggcttttagt aagccggatc ctctagatta cgccccgcct gccactcatc      840
gcagtactgt tgtaattcat taagcattct gccgacatgg aagccatcac aaacggcatg      900
atgaacctga atcgccagcg gcatcagcac cttgtcgcct tgcgtataat atttgcccat      960
ggtgaaaacg ggggcgaaga agttgtccat attggccacg tttaaatcaa aactggtgaa     1020
```

```
actcacccag ggattggctg agacgaaaaa catattctca ataaacccct tagggaaata    1080
ggccaggttt tcaccgtaac acgccacatc ttgcgaatat atgtgtagaa actgccggaa    1140
atcgtcgtgg tattcactcc agagcgatga aaacgtttca gtttgctcat ggaaaacggt    1200
gtaacaaggg tgaacactat cccatatcac cagctcaccg tctttcattg ccatacggaa    1260
ttccggatga gcattcatca ggcgggcaag aatgtgaata aaggccggat aaaacttgtg    1320 cttattttc tttacggtct ttaaaaaggc cgtaatatcc agctgaacgg tctggttata    1380
ggtacattga gcaactgact gaaatgcctc aaaatgttct ttacgatgcc attgggatat    1440
atcaacggtg gtatatccag tgatttttt ctccatttta gcttccttag ctcctgaaaa    1500
tctcgacgga tcctaactca aaatccacac attatacgag ccggaagcat aaagtgtaaa    1560
gcctggggtg cctaatgcgg ccgccatagt gactggatat gttgtgtttt acagtattat    1620
gtagtctgtt ttttatgcaa aatctaattt aatatattga tatttatatc attttacgtt    1680
tctcgttcag cttttttgta caaacttgtt tgataaacac tagtaacggc cgccagtgtg    1740
ctggaattcg ccctccccaa gctttgctct agatcaaact cacatccaaa cataacatgg    1800
atatcttcct taccaatcat actaattatt ttgggttaaa tattaatcat tatttttaag    1860
atattaatta agaaattaaa agattttta aaaaaatgta taaaattata ttattcatga    1920
tttttcatac atttgatttt gataataaat atatttttt taatttctta aaaaatgttg    1980
caagacactt attagacata gtcttgttct gtttacaaaa gcattcatca tttaatacat    2040
taaaaaatat ttaatactaa cagtagaatc ttcttgtgag tggtgtggga gtaggcaacc    2100
tggcattgaa acgagagaaa gagagtcaga accagaagac aaataaaaag tatgcaacaa    2160
acaaatcaaa atcaaagggc aaaggctggg gttggctcaa ttggttgcta cattcaattt    2220
tcaactcagt caacggttga gattcactct gacttcccca atctaagccg cggatgcaaa    2280
cggttgaatc taacccacaa tccaatctcg ttacttaggg cttttccgt cattaactca    2340 cccctgccac ccggtttccc tataaattgg aactcaatgc tccctctaa actcgtatcg    2400 cttcagagtt gagaccaaga cacactcgtt catatatctc tctgctcttc tcttctcttc    2460
tacctctcaa ggtacttttc ttctccctct accaaatcct agattccgtg gttcaatttc    2520
ggatcttgca cttctggttt gctttgcctt gcttttcct caactgggtc catctaggat    2580
ccatgtgaaa ctctactctt tctttaatat ctgcggaata cgcgtttgac tttcagatct    2640
agtcgaaatc atttcataat tgcctttctt tcttttagct tatgagaaat aaaatcactt    2700 ttttttatt tcaaaataaa ccttgggcct tgtgctgact gagatggggt ttggtgatta    2760 cagaattta gcgaattttg taattgtact tgtttgtctg tagttttgtt ttgttttctt    2820
gtttctcata cattccttag gcttcaattt tattcgagta taggtcacaa taggaattca    2880
aactttgagc aggggaatta atcccttcct tcaaatccag tttgtttgta tatatgttta    2940
aaaaatgaaa cttttgcttt aaattctatt ataacttttt ttatggctga aattttgca    3000 tgtgtctttg ctctctgttg taaatttact gtttaggtac taactctagg cttgttgtgc    3060 agttttgaa gtataacaac agaagttcct attccgaagt tcctattctc tagaaagtat    3120
aggaacttcc accacacaac acaatggcgg ccaccgcttc cagaaccacc cgattctctt    3180
cttcctcttc acacccccacc ttccccaaac gcattactag atccaccctc cctctctctc    3240 atcaaacccct caccaaaccc aaccacgctc tcaaaatcaa atgttccatc tccaaacccc    3300
ccacggcggc gcccttcacc aaggaagcgc cgaccacgga gccctcgtg tcacggttcg    3360 cctccggcga acctcgcaag ggcgcggaca tccttgtgga ggcgctggag aggcagggcg    3420
```

```
tgacgacggt gttcgcgtac cccggcggtg cgtcgatgga gatccaccag gcgctcacgc    3480
gctccgccgc catccgcaac gtgctcccgc gccacgagca gggcggcgtc ttcgccgccg    3540
aaggctacgc gcgttcctcc ggcctccccg gcgtctgcat tgccacctcc ggccccggcg    3600
ccaccaacct cgtgagcggc ctcgccgacg ctttaatgga cagcgtccca gtcgtcgcca    3660
tcaccggcca ggtcgcccgc cggatgatcg gcaccgacgc cttccaagaa accccgatcg    3720
tggaggtgag cagatccatc acgaagcaca actacctcat cctcgacgtc gacgacatcc    3780
cccgcgtcgt cgccgaggct ttcttcgtcg ccacctccgg ccgccccggt ccggtcctca    3840
tcgacattcc caaagacgtt cagcagcaac tcgccgtgcc taattgggac gagcccgtta    3900
acctccccgg ttacctcgcc aggctgccca ggccccccgc cgaggcccaa ttggaacaca    3960
ttgtcagact catcatggag gcccaaaagc ccgttctcta cgtcggcggt ggcagtttga    4020
attccagtgc tgaattgagg cgctttgttg aactcactgg tattcccgtt gctagcactt    4080
taatgggtct tggaactttt cctattggtg atgaatattc ccttcagatg ctgggtatgc    4140
atggtactgt ttatgctaac tatgctgttg acaatagtga tttgttgctt gcctttgggg    4200
taaggtttga tgaccgtgtt actgggaagc ttgaggcttt tgctagtagg gctaagattg    4260
ttcacattga tattgattct gccgagattg ggaagaacaa gcaggcgcac gtgtcggttt    4320
gcgcggattt gaagttggcc ttgaagggaa ttaatatgat tttggaggag aaaggagtgg    4380
agggtaagtt tgatcttgga ggttggagag aagagattaa tgtgcagaaa cacaagtttc    4440
cattgggtta caagacattc caggacgcga tttctccgca gcatgctatc gaggttcttg    4500
atgagttgac taatggagat gctattgtta gtactggggt tgggcagcat caaatgtggg    4560
ctgcgcagtt ttacaagtac aagagaccga ggcagtggtt gacctcaggg ggtcttggag    4620
ccatgggttt tggattgcct gcggctattg gtgctgctgt tgctaaccct ggggctgttg    4680
tggttgacat tgatggggat ggtagtttca tcatgaatgt tcaggagttg gccactataa    4740
gagtggagaa tctcccagtt aagatattgt tgttgaacaa tcagcatttg ggtatggtgg    4800
ttcagttgga ggataggttc tacaagtcca atagagctca cacctatctt ggagatccgt    4860
ctagcgagag cgagatattc ccaaacatgc tcaagtttgc tgatgcttgt gggataccgg    4920
cagcgcgagt gacgaagaag gaagagctta gagcggcaat tcagagaatg ttggacaccc    4980
ctggccccta ccttcttgat gtcattgtgc cccatcagga gcatgtgttg ccgatgattc    5040
ccagtaatgg atccttcaag gatgtgataa ctgagggtga tggtagaacg aggtactgat    5100
tgcctagacc aaatgttcct tgatgcttgt tttgtacaat atatataaga taatgctgtc    5160
ctagttgcag gatttggcct gtggtgagca tcatagtctg tagtagtttt ggtagcaaga    5220
cattttattt tccttttatt taacttacta catgcagtag catctatcta tctctgtagt    5280
ctgatatctc ctgttgtctg tattgtgccg ttggattttt tgctgtagtg agactgaaaa    5340
tgatgtgcta gtaataatat ttctgttaga aatctaagta gagaatctgt tgaagaagtc    5400
aaaagctaat ggaatcaggt tacatattca atgttttttct tttttttagcg gttggtagac    5460 gtgtagattc aacttctctt ggagctcacc taggcaatca gtaaaatgca tattccttt    5520 ttaacttgcc atttatttac ttttagtgga aattgtgacc aatttgttca tgtagaacgg    5580
atttggacca ttgcgtccac aaaacgtctc ttttgctcga tcttcacaaa gcgataccga    5640
aatccagaga tagttttcaa aagtcagaaa tggcaaagtt ataaatagta aaacagaata    5700
gatgctgtaa tcgacttcaa taacaagtgg catcacgttt ctagttctag acccatcagc    5760
```

```
tgggccggcc cagctgatga tcccggtgaa gttcctattc cgaagttcct attctccaga    5820
aagtatagga acttcactag agcttgcggc cgcgcatgct gacttaatca gctaacgcca    5880
ctcgaggggg ggcccggtac cggcgcgccg ttctatagtg tcacctaaat cgtatgtgta    5940
tgatacataa ggttatgtat taattgtagc cgcgttctaa cgacaatatg tccatatggt    6000
gcactctcag tacaatctgc tctgatgccg catagttaag ccagcccga cacccgccaa     6060 cacccgctga cgcgccctga cgggcttgtc tgctcccggc atccgcttac agacaagctg    6120
tgaccgtctc cgggagctgc atgtgtcaga ggttttcacc gtcatcaccg aaacgcgcga    6180
gacgaagggg cctcgtgata cgcctatttt tataggttaa tgtcatgacc aaaatccctt    6240
aacgtgagtt ttcgttccac tgagcgtcag accccgtaga aaagatcaaa ggatcttctt    6300
gagatccttt ttttctgcgc gtaatctgct gcttgcaaac aaaaaaacca ccgctaccag    6360
cggtggtttg tttgccggat caagagctac caactctttt tccgaaggta actggcttca    6420
gcagagcgca gataccaaat actgtccttc tagtgtagcc gtagttaggc caccacttca    6480
agaactctgt agcaccgcct acatacctcg ctctgctaat cctgttacca gtggctgctg    6540
ccagtggcga taagtcgtgt cttaccgggt tggactcaag acgatagtta ccggataagg    6600
cgcagcggtc gggctgaacg ggggggttcgt gcacacagcc cagcttggag cgaacgacct    6660
acaccgaact gagataccta cagcgtgagc attgagaaag cgccacgctt cccgaaggga    6720
gaaaggcgga caggtatccg gtaagcggca gggtcggaac aggagagcgc acgagggagc    6780
ttccaggggg aaacgcctgg tatctttata gtcctgtcgg gtttcgccac tctgacttg     6840 agcgtcgatt tttgtgatgc tcgtcagggg ggcggagcct atggaaaaac gccagcaacg    6900 cggcctttt acggttcctg gccttttgct ggccttttgc tcacatgttc tttcctgcgt     6960
tatcccctga ttctgtggat aaccgtatta ccgcctttga gtgagctgat accgctcgcc    7020
gcagccgaac gaccgagcgc agcgagtcag tgagcgagga agcggaagag cgcccaatac    7080
gcaaaccgcc tctccccgcg cgttggccga ttcattaatg caggttgatc agatctcgat    7140
cccgcgaaat taatacgact cactataggg agaccacaac ggtttccctc tagaaataat    7200
tttgtttaac tttaagaagg agatatacc atggaaaagc tgaactcac cgcgacgtct     7260 gtcgagaagt ttctgatcga aaagttcgac agcgtctccg acctgatgca gctctcggag    7320
ggcgaagaat ctcgtgcttt cagcttcgat gtaggagggc gtggatatgt cctgcgggta    7380
aatagctgcg ccgatggttt ctacaaagat cgttatgttt atcggcactt tgcatcggcc    7440
gcgctcccga ttccggaagt gcttgacatt ggggaattca gcgagagcct gacctattgc    7500
atctcccgcc gtgcacaggg tgtcacgttg caagacctgc ctgaaaccga actgcccgct    7560
gttctgcagc cggtcgcgga ggctatggat gcgatcgctg cggccgatct tagccagacg    7620
agcgggttcg gcccattcgg accgcaagga atcggtcaat acactacatg gcgtgatttc    7680
atatgcgcga ttgctgatcc ccatgtgtat cactggcaaa ctgtgatgga cgaccacgtc    7740
agtgcgtccg tcgcgcaggc tctcgatgag ctgatgcttt gggccgagga ctgccccgaa    7800
gtccggcacc tcgtgcacgc ggatttcggc tccaacaatg tcctgacgga caatggccgc    7860
ataacagcgg tcattgactg gagcgaggcg atgttcgggg attcccaata cgaggtcgcc    7920
aacatcttct tctggaggcc gtggttggct tgtatggagc agcagacgcg ctacttcgag    7980
cggaggcatc cggagcttgc aggatcgccg cggctccggg cgtatatgct ccgcattggt    8040
cttgaccaac tctatcagag cttggttgac ggcaatttcg atgatgcagc ttgggcgcag    8100
ggtcgatgcg acgcaatcgt ccgatccgga gccgggactg tcgggcgtac acaaatcgcc    8160
```

```
cgcagaagcg cggccgtctg gaccgatggc tgtgtagaag tactcgccga tagtggaaac    8220
cgacgcccca gcactcgtcc gagggcaaag gaatagtgag gtacagcttg gatcgatccg    8280
gctgctaaca aagcccgaaa ggaagctgag ttggctgctg ccaccgctga gcaataacta    8340
gcataacccc ttggggcctc taaacgggtc ttgaggggtt ttttgctgaa aggaggaact    8400
atatccggat gctcgggcgc gccggtaccc gggtaccgag ctcactagac gcggtgaaat    8460
tacctaatta acaccggtgt tt                                             8482

<210> SEQ ID NO 22
<211> LENGTH: 9509
<212> TYPE: DNA
<213> ORGANISM: Artificial Sequence
<220> FEATURE:
<223> OTHER INFORMATION: plasmid QC644

<400> SEQUENCE: 22
cccgggagtt cacatgctat gaatccgtta tcataaactc caaagccatg attacaacat      60
aaagagatgt tattaaaatt gaaataaata aaatttgagg cttaggtcct cgtgcacata     120
aacttgcatg atgatttaca gctctctctc ccactttgag tcttgtggta atttgaggta     180
aatattggat ccaactcagc aactactagt aagctttctc tcaaaagaaa aaaaaaacca     240
ctagtaagct ttatttttcta gtgaagcaac tgctatagtc ttgggttttg gagaaattgt     300
caggtgtgcc attaaattaa gagttgcgtc gattatcctt acctttttta tataaaaaaa     360
tattccattt aattttgatt aaaatatata ttatttcacg acaaaaaaat actcgtgtag     420 attctatttta tacaaatttg ctagattaag aaaattaaga atagacaaat tataatgtga     480
cataaatatt tctatgattg cttgaagtaa aatagcaaaa attagtttaa attgttttta     540
tataattcaa gtataaaatt gtcatatttt tctataaaag tgtcaacttt taatagaatg     600
tggttaaatg atgatttctc attgggtatc catgtaaaaa tattgttgtc atttttattg     660
tcatactttt acacaatttt tcatgatgtg atataattga taaataatct tatactttaa     720 gtataaaaatt agagattgaa ttcccaaata taaaaataat attattgaga gagatcaact     780
tcttagataa atcttgatac ttcgagtagc accctgactt aaaaaatgtc cttggtaaat     840
ttttatttat taatatgatg cggttataaa gtaaattctt attagataat tgtgtaaaaa     900
ttcatctgtt ttttgtttaa gaatgtgtat atagttgatt aatttaatct atataataat     960
ttgtacggaa aaatatact atttgggacc ctgagattat tatgtttggt agaatttggg    1020
aggtgggaag attggatgtt aggtggaacg aggtcaggaa cgacacatc tggtcgggga    1080 ggggaggtag aaaattata cattgacaca ataggataat tggtacctag tgagataaaa    1140 tttaaaaaa atatagatat tcatattata ggtattatga tttggtatga agagaaaaa    1200 aagaagatga aaagtgttta aaaataagt ttaatattta tgcattgaaa tcatgatgaa    1260
ttatgagtag atgtgtgttt aatgtccatc tatcatcttc acagtatggg acaacacaaa    1320
agcaatatga atgtgatgga ccacaattgg gccctcaagc cccaattcgg cccattgggc    1380
catcgaaaag aaaaagcatg cgctgcggat attaataatt ttgtgacgct ccaccacaat    1440
tccccatccc caaatttct cattctccct ttcctctccg aaccctcgat cactctcacg    1500
cgctcctata ttcgctcctc caccgtcgct ctctcgaaca accacaacac catcttcatc    1560
accatggccc agtccaagca cggcctgacc aaggagatga ccatgaagta ccgcatggag    1620
ggctgcgtgg acggccacaa gttcgtgatc accggcgagg gcatcggcta cccccttcaag    1680
```

```
ggcaagcagg ccatcaacct gtgcgtggtg gagggcggcc ccttgccctt cgccgaggac    1740
atcttgtccg ccgccttcat gtacggcaac cgcgtgttca ccgagtaccc ccaggacatc    1800
gtcgactact tcaagaactc ctgccccgcc ggctacacct gggaccgctc cttcctgttc    1860
gaggacggcg ccgtgtgcat ctgcaacgcc gacatcaccg tgagcgtgga ggagaactgc    1920
atgtaccacg agtccaagtt ctacggcgtg aacttccccg ccgacggccc cgtgatgaag    1980
aagatgaccg acaactggga gccctcctgc gagaagatca tccccgtgcc caagcagggc    2040
atcttgaagg gcgacgtgag catgtacctg ctgctgaagg acggtggccg cttgcgctgc    2100
cagttcgaca ccgtgtacaa ggccaagtcc gtgccccgca gatgcccgga ctggcacttc    2160
atccagcaca agctgacccg cgaggaccgc agcgacgcca agaaccagaa gtggcacctg    2220
accgagcacg ccatcgcctc cggctccgcc ttgccctccg gactcagatc tcgactagag    2280
tcgaacctag acttgtccat cttctggatt ggccaactta attaatgtat gaaataaaag    2340
gatgcacaca tagtgacatg ctaatcacta taatgtgggc atcaaagttg tgtgttatgt    2400
gtaattacta gttatctgaa taaaagagaa agagatcatc catatttctt atcctaaatg    2460
aatgtcacgt gtctttataa ttctttgatg aaccagatgc atttcattaa ccaaatccat    2520
atacatataa atattaatca tatataatta atatcaattg ggttagcaaa acaaatctag    2580
tctaggtgtg ttttgcgaat tctagtggcc ggcccagctg atatccatca cactggcggc    2640
cgcactcgac tgaattggtt ccggcgccag cctgcttttt tgtacaaact tgtttgataa    2700
acactagtaa cggccgccag tgtgctggaa ttcgcccttc ccaagctttg ctctagatca    2760
aactcacatc caaacataac atggatatct tccttaccaa tcatactaat tattttgggt    2820
taaatattaa tcattatttt taagatatta attaagaaat taaagatttt tttaaaaaaa    2880
tgtataaaat tatattattc atgattttc  atacatttga ttttgataat aaatatattt    2940
tttttaattt cttaaaaaat gttgcaagac acttattaga catagtcttg ttctgtttac    3000
aaaagcattc atcatttaat acattaaaaa atatttaata ctaacagtag aatcttcttg    3060
tgagtggtgt gggagtaggc aacctggcat tgaaacgaga gaaagagagt cagaaccaga    3120
agacaaataa aaagtatgca acaaacaaat caaaatcaaa gggcaaaggc tggggttggc    3180
tcaattggtt gctacattca attttcaact cagtcaacgg ttgagattca ctctgacttc    3240
cccaatctaa gccgcggatg caaacggttg aatctaaccc acaatccaat ctcgttactt    3300 aggggcttt  ccgtcattaa ctcaccctg  ccacccggtt tccctataaa ttggaactca    3360
atgctcccct ctaaactcgt atcgcttcag agttgagacc aagacacact cgttcatata    3420
tctctctgct cttctcttct cttctacctc tcaaggtact tttcttctcc ctctaccaaa    3480
tcctagattc cgtggttcaa tttcggatct tgcacttctg gtttgctttg ccttgctttt    3540
tcctcaactg ggtccatcta ggatccatgt gaaactctac tctttcttta atatctgcgg    3600
aatacgcgtt tgactttcag atctagtcga aatcatttca taattgcctt tctttctttt    3660
agcttatgag aaataaaatc actttttttt tatttcaaaa taaaccttgg gccttgtgct    3720
gactgagatg gggtttggtg attacagaat tttagcgaat tttgtaattg tacttgtttg    3780
tctgtagttt tgtttgtttt tcttgttct  catacattcc ttaggcttca attttattcg    3840
agtataggtc acaataggaa ttcaaacttt gagcagggga attaatccct tccttcaaat    3900
ccagtttgtt tgtatatatg tttaaaaaat gaaactttg  ctttaaattc tattataact    3960
ttttttatgg ctgaaatttt tgcatgtgtc tttgctctct gttgtaaatt tactgtttag    4020
gtactaactc taggcttgtt gtgcagtttt tgaagtataa caacagaagt tcctattccg    4080
```

```
aagttcctat tctctagaaa gtataggaac ttccaccaca caacacaatg gcggccaccg   4140
cttccagaac cacccgattc tcttcttcct cttcacaccc caccttcccc aaacgcatta   4200
ctagatccac cctccctctc tctcatcaaa ccctcaccaa acccaaccac gctctcaaaa   4260
tcaaatgttc catctccaaa ccccccacgg cggcgcccett caccaaggaa gcgccgacca   4320
cggagcccett cgtgtcacgg ttcgcctccg gcgaacctcg caagggcgcg gacatccttg   4380
tggaggcgct ggagaggcag ggcgtgacga cggtgttcgc gtaccccggc ggtgcgtcga   4440
tggagatcca ccaggcgctc acgcgctccg ccgccatccg caacgtgctc ccgcgccacg   4500
agcagggcgg cgtcttcgcc gccgaaggct acgcgcgttc ctccggcctc cccggcgtct   4560
gcattgccac ctccggcccc ggcgccacca acctcgtgag cggcctcgcc gacgctttaa   4620
tggacagcgt cccagtcgtc gccatcaccg gccaggtcgc ccgccggatg atcggcaccg   4680
acgccttcca agaaaccccg atcgtggagg tgagcagatc catcacgaag cacaactacc   4740
tcatcctcga cgtcgacgac atcccccgcg tcgtcgccga ggctttcttc gtcgccacct   4800
ccggccgccc cggtccggtc ctcatcgaca ttcccaaaga cgttcagcag caactcgccg   4860
tgcctaattg ggacgagccc gttaacctcc ccggttacct cgccaggctg cccaggcccc   4920
ccgccgaggc ccaattggaa cacattgtca gactcatcat ggaggcccaa aagcccgttc   4980
tctacgtcgg cggtggcagt ttgaattcca gtgctgaatt gaggcgcttt gttgaactca   5040
ctggtattcc cgttgctagc actttaatgg gtcttggaac ttttcctatt ggtgatgaat   5100
attcccttca gatgctgggt atgcatggta ctgtttatgc taactatgct gttgacaata   5160
gtgatttgtt gcttgccttt ggggtaaggt ttgatgaccg tgttactggg aagcttgagg   5220
cttttgctag tagggctaag attgttcaca ttgatattga ttctgccgag attgggaaga   5280
acaagcaggc gcacgtgtcg gtttgcgcgg atttgaagtt ggccttgaag ggaattaata   5340
tgattttgga ggagaaagga gtggagggta agtttgatct tggaggttgg agagaagaga   5400
ttaatgtgca gaaacacaag tttccattgg gttacaagac attccaggac gcgatttctc   5460
cgcagcatgc tatcgaggtt cttgatgagt tgactaatgg agatgctatt gttagtactg   5520
gggttgggca gcatcaaatg tgggctgcgc agttttacaa gtacaagaga ccgaggcagt   5580
ggttgacctc aggggtett ggagccatgg gttttggatt gcctgcggct attggtgctg   5640
ctgttgctaa ccctggggct gttgtggttg acattgatgg ggatggtagt ttcatcatga   5700
atgttcagga gttggccact ataagagtgg agaatctccc agttaagata ttgttgttga   5760
acaatcagca tttgggtatg gtggttcagt tggaggatag gttctacaag tccaatagag   5820
ctcacaccta tcttggagat ccgtctagcg agagcgagat attcccaaac atgctcaagt   5880
ttgctgatgc ttgtgggata ccggcagcgc gagtgacgaa gaaggaagag cttagagcgg   5940
caattcagag aatgttggac acccctggcc cctaccttct tgatgtcatt gtgccccatc   6000
aggagcatgt gttgccgatg attcccagta atggatcctt caaggatgtg ataactgagg   6060
gtgatggtag aacgaggtac tgattgccta gaccaaatgt tccttgatgc ttgttttgta   6120
caatatatat aagataatgc tgtcctagtt gcaggatttg gcctgtggtg agcatcatag   6180
tctgtagtag ttttggtagc aagacatttt attttccttt tatttaactt actacatgca   6240
gtagcatcta tctatctctg tagtctgata tctcctgttg tctgtattgt gccgttggat   6300
tttttgctgt agtgagactg aaaatgatgt gctagtaata atatttctgt tagaaatcta   6360
agtagagaat ctgttgaaga agtcaaaagc taatggaatc aggttacata ttcaatgttt   6420
```

```
ttcttttttt agcggttggt agacgtgtag attcaacttc tcttggagct cacctaggca   6480
atcagtaaaa tgcatattcc ttttttaact tgccatttat ttacttttag tggaaattgt   6540
gaccaatttg ttcatgtaga acggatttgg accattgcgt ccacaaaacg tctcttttgc   6600
tcgatcttca caaagcgata ccgaaatcca gagatagttt tcaaaagtca gaaatggcaa   6660
agttataaat agtaaaacag aatagatgct gtaatcgact tcaataacaa gtggcatcac   6720
gtttctagtt ctagacccat cagctgggcc ggcccagctg atgatcccgg tgaagttcct   6780
attccgaagt tcctattctc cagaaagtat aggaacttca ctagagcttg cggccgcgca   6840
tgctgactta atcagctaac gccactcgag gggggggccg gtaccggcgc gccgttctat   6900
agtgtcacct aaatcgtatg tgtatgatac ataaggttat gtattaattg tagccgcgtt   6960
ctaacgacaa tatgtccata tggtgcactc tcagtacaat ctgctctgat gccgcatagt   7020
taagccagcc ccgacacccg ccaacacccg ctgacgcgcc ctgacgggct tgtctgctcc   7080
cggcatccgc ttacagacaa gctgtgaccg tctccgggag ctgcatgtgt cagaggtttt   7140
caccgtcatc accgaaacgc gcgagacgaa agggcctcgt gatacgccta ttttttatagg   7200 ttaatgtcat gaccaaaatc ccttaacgtg agttttcgtt ccactgagcg tcagaccccg   7260
tagaaaagat caaaggatct tcttgagatc ctttttttct gcgcgtaatc tgctgcttgc   7320
aaacaaaaaa accaccgcta ccagcggtgg tttgtttgcc ggatcaagag ctaccaactc   7380
tttttccgaa ggtaactggc ttcagcagag cgcagatacc aaatactgtc cttctagtgt   7440
agccgtagtt aggccaccac ttcaagaact ctgtagcacc gcctacatac ctcgctctgc   7500
taatcctgtt accagtggct gctgccagtg gcgataagtc gtgtcttacc gggttggact   7560
caagacgata gttaccggat aaggcgcagc ggtcgggctg aacggggggt tcgtgcacac   7620
agcccagctt ggagcgaacg acctacaccg aactgagata cctacagcgt gagcattgag   7680
aaagcgccac gcttcccgaa gggagaaagg cggacaggta tccggtaagc ggcagggtcg   7740
gaacaggaga gcgcacgagg gagcttccag ggggaaacgc ctggtatctt tatagtcctg   7800
tcgggtttcg ccacctctga cttgagcgtc gatttttgtg atgctcgtca ggggggcgga   7860
gcctatggaa aaacgccagc aacgcggcct ttttacggtt cctggccttt tgctggcctt   7920
ttgctcacat gttctttcct gcgttatccc ctgattctgt ggataaccgt attaccgcct   7980
ttgagtgagc tgataccgct cgccgcagcc gaacgaccga gcgcagcgag tcagtgagcg   8040
aggaagcgga agagcgccca atacgcaaac cgcctctccc cgcgcgttgg ccgattcatt   8100
aatgcaggtt gatcagatct cgatcccgcg aaattaatac gactcactat agggagacca   8160
caacggtttc cctctagaaa taattttgtt taactttaag aaggagatat acccatggaa   8220
aagcctgaac tcaccgcgac gtctgtcgag aagtttctga tcgaaaagtt cgacagcgtc   8280
tccgacctga tgcagctctc ggagggcgaa gaatctcgtg ctttcagctt cgatgtagga   8340
gggcgtggat atgtcctgcg ggtaaatagc tgcgccgatg gtttctacaa agatcgttat   8400
gtttatcggc actttgcatc ggccgcgctc ccgattccgg aagtgcttga cattgggaa    8460 ttcagcgaga gcctgaccta ttgcatctcc cgccgtgcac agggtgtcac gttgcaagac   8520
ctgcctgaaa ccgaactgcc cgctgttctg cagccggtcg cggaggctat ggatgcgatc   8580
gctgcggccg atcttagcca cgagcgggt tcggcccat tcggaccgca aggaatcggt    8640
caatacacta catggcgtga tttcatatgc gcgattgctg atccccatgt gtatcactgg   8700
caaactgtga tggacgacac cgtcagtgcg tccgtcgcgc aggctctcga tgagctgatg   8760
ctttgggccg aggactgccc cgaagtccgg cacctcgtgc acgcggattt cggctccaac   8820
```

| | |
|---|---:|
| aatgtcctga cggacaatgg ccgcataaca gcggtcattg actggagcga ggcgatgttc | 8880 |
| ggggattccc aatacgaggt cgccaacatc ttcttctgga ggccgtggtt ggcttgtatg | 8940 |
| gagcagcaga cgcgctactt cgagcggagg catccggagc ttgcaggatc gccgcggctc | 9000 |
| cgggcgtata tgctccgcat tggtcttgac caactctatc agagcttggt tgacggcaat | 9060 |
| ttcgatgatg cagcttgggc gcagggtcga tgcgacgcaa tcgtccgatc cggagccggg | 9120 |
| actgtcgggc gtacacaaat cgcccgcaga agcgcggccg tctggaccga tggctgtgta | 9180 |
| gaagtactcg ccgatagtgg aaaccgacgc cccagcactc gtccgagggc aaaggaatag | 9240 |
| tgaggtacag cttggatcga tccggctgct aacaaagccc gaaaggaagc tgagttggct | 9300 |
| gctgccaccg ctgagcaata actagcataa cccctggggg cctctaaacg ggtcttgagg | 9360 |
| ggttttttgc tgaaaggagg aactatatcc ggatgctcgg gcgcgccggt acccgggtac | 9420 |
| cgagctcact agacgcggtg aaattaccta attaacaccg gtgtttatcg aaccactttg | 9480 |
| tacaagaaag ctgggtctag atatctcga | 9509 |

<210> SEQ ID NO 23
<211> LENGTH: 4376
<212> TYPE: DNA
<213> ORGANISM: Artificial Sequence
<220> FEATURE:
<223> OTHER INFORMATION: plasmid QC532-1

<400> SEQUENCE: 23

| | |
|---|---:|
| gggagttcac atgctatgaa tccgttatca taaactccaa agccatgatt acaacataaa | 60 |
| gagatgttat taaaattgaa ataaataaaa tttgaggctt aggtcctcgt gcacataaac | 120 |
| ttgcatgatg atttacagct ctctctccca ctttgagtct tgtggtaatt tgaggtaaat | 180 |
| attggatcca actcagcaac tactagtaag ctttctctca aaagaaaaaa aaaaccacta | 240 |
| gtaagcttta ttttctagtg aagcaactgc tatagtcttg ggttttggag aaattgtcag | 300 |
| gtgtgccatt aaattaagag ttgcgtcgat tatccttacc tttttttatat aaaaaaatat | 360 |
| tccatttaat tttgattaaa atatatatta tttcacgaca aaaaaatact cgtgtagatt | 420 |
| ctatttatac aaatttgcta gattaagaaa attaagaata gacaaattat aatgtgacat | 480 |
| aaatatttct atgattgctt gaagtaaaat agcaaaaatt agtttaaatt gttttttatat | 540 |
| aattcaagta taaaattgtc atattttttct ataaaagtgt caacttttaa tagaatgtgg | 600 |
| ttaaatgatg atttctcatt gggtatccat gtaaaaatat tgttgtcatt ttatttgtca | 660 |
| tacttttaca caatttttca tgatgtgata taattgataa ataatcttat actttaagta | 720 |
| taaaattaga gattgaattc ccaaatataa aaataatatt attgagagag atcaacttct | 780 |
| tagataaatc ttgatacttc gagtagcacc ctgacttaaa aaatgtcctt ggtaaatttt | 840 |
| tatttattaa tatgatgcgg ttataaagta aattcttatt agataattgt gtaaaaattc | 900 |
| atctgttttt tgtttaagaa tgtgtatata gttgattaat ttaatctata taataatttg | 960 |
| tacggaaaaa atatactatt tgggaccctg agattattat gtttggtaga atttgggagg | 1020 |
| tgggaagatt ggatgttagg tggaacgagg tcaggagacg acacatctgg tcgggagggg | 1080 |
| gaggtagaaa aattatacat tgacacaata ggataattgg tacctagtga gataaaatttt | 1140 |
| taaaaaaata tagatattca tattataggt attatgattt ggtatgaaag agaaaaaaag | 1200 |
| aagatgaaaa gtgtttaaaa aataagttta atatttatgc attgaaatca tgatgaatta | 1260 |
| tgagtagatg tgtgttaat gtccatctat catcttcaca gtatgggaca acacaaaagc | 1320 |

```
aatatgaatg tgatggacca caattgggcc ctcaagcccc aattcggccc attgggccat      1380
cgaaaagaaa aagcatgcgc tgcggatatt aataattttg tgacgctcca ccacaattcc      1440
ccatccccaa aatttctcat tctccctttc ctctccgaac cctcgatcac tctcacgcgc      1500
tcctatattc gctcctccac cgtcgctctc tcgaacaacc acaacaccat cttcatcaca      1560
agggcgaatt cgacccagct ttcttgtaca aagttggcat tataaaaaat aattgctcat      1620
caatttgttg caacgaacag gtcactatca gtcaaaataa aatcattatt tgccatccag      1680
ctgatatccc ctatagtgag tcgtattaca tggtcatagc tgtttcctgg cagctctggc      1740
ccgtgtctca aaatctctga tgttacattg cacaagataa aaatatatca tcatgcctcc      1800
tctagaccag ccaggacaga aatgcctcga cttcgctgct gcccaaggtt gccgggtgac      1860
gcacaccgtg gaaacggatg aaggcacgaa cccagtggac ataagcctgt tcggttcgta      1920
agctgtaatg caagtagcgt atgcgctcac gcaactggtc cagaaccttg accgaacgca      1980
gcggtggtaa cggcgcagtg gcggttttca tggcttgtta tgactgtttt tttggggtac      2040
agtctatgcc tcgggcatcc aagcagcaag cgcgttacgc cgtgggtcga tgtttgatgt      2100
tatggagcag caacgatgtt acgcagcagg gcagtcgccc taaaacaaag ttaaacatca      2160
tgagggaagc ggtgatcgcc gaagtatcga ctcaactatc agaggtagtt ggcgtcatcg      2220
agcgccatct cgaaccgacg ttgctggccg tacatttgta cggctccgca gtggatggcg      2280
gcctgaagcc acacagtgat attgatttgc tggttacggt gaccgtaagg cttgatgaaa      2340
caacgcggcg agctttgatc aacgaccttt tggaaacttc ggcttcccct ggagagagcg      2400
agattctccg cgctgtagaa gtcaccattg ttgtgcacga cgacatcatt ccgtggcgtt      2460
atccagctaa gcgcgaactg caatttggag aatggcagcg caatgacatt cttgcaggta      2520
tcttcgagcc agccacgatc gacattgatc tggctatctt gctgacaaaa gcaagagaac      2580
atagcgttgc cttggtaggt ccagcggcgg aggaactctt tgatccggtt cctgaacagg      2640
atctatttga ggcgctaaat gaaaccttaa cgctatggaa ctcgccgccc gactgggctg      2700
gcgatgagcg aaatgtagtg cttacgttgt cccgcatttg gtacagcgca gtaaccggca      2760
aaatcgcgcc gaaggatgtc gctgccgact gggcaatgga gcgcctgccg gcccagtatc      2820
agcccgtcat acttgaagct agacaggctt atcttggaca agaagaagat cgcttggcct      2880
cgcgcgcaga tcagttggaa gaatttgtcc actacgtgaa aggcgagatc accaaggtag      2940
tcggcaaata accctcgagc cacccatgac caaaatccct taacgtgagt tacgcgtcgt      3000
tccactgagc gtcagacccc gtagaaaaga tcaaaggatc ttcttgagat cctttttttc      3060
tgcgcgtaat ctgctgcttg caaacaaaaa aaccaccgct accagcggtg gtttgtttgc      3120
cggatcaaga gctaccaact cttttttccga aggtaactgg cttcagcaga gcgcagatac      3180
caaatactgt ccttctagtg tagccgtagt taggccacca cttcaagaac tctgtagcac      3240
cgcctacata cctcgctctg ctaatcctgt taccagtggc tgctgccagt ggcgataagt      3300
cgtgtcttac cgggttggac tcaagacgat agttaccgga taaggcgcag cggtcgggct      3360
gaacgggggg ttcgtgcaca cagcccagct tggagcgaac gacctacacc gaactgagat      3420
acctacagcg tgagcattga gaaagcgcca cgcttcccga agggagaaag gcggacaggt      3480
atccggtaag cggcagggtc ggaacaggag agcgcacgag ggagcttcca gggggaaacg      3540
cctggtatct ttatagtcct gtcgggtttc gccacctctg acttgagcgt cgatttttgt      3600
gatgctcgtc aggggggcgg agcctatgga aaaacgccag caacgcggcc ttttacggtt      3660
tcctggcctt ttgctggcct tttgctcaca tgttctttcc tgcgttatcc cctgattctg      3720
```

```
tggataaccg tattaccgcc tttgagtgag ctgataccgc tcgccgcagc cgaacgaccg    3780
agcgcagcga gtcagtgagc gaggaagcgg aagagcgccc aatacgcaaa ccgcctctcc    3840
ccgcgcgttg gccgattcat taatgcagct ggcacgacag gtttcccgac tggaaagcgg    3900
gcagtgagcg caacgcaatt aatacgcgta ccgctagcgg gaagagtttg tagaaacgc     3960 aaaaaggcca tccgtcagga tggccttctg cttagtttga tgcctggcag tttatggcgg    4020
gcgtcctgcc cgccaccctc cgggccgttg cttcacaacg ttcaaatccg ctcccggcgg    4080
atttgtccta ctcaggagag cgttcaccga caaacaacag ataaaacgaa aggcccagtc    4140
ttccgactga gcctttcgtt ttatttgatg cctggcagtt ccctactctc gcgttaacgc    4200
tagcatggat gttttcccag tcacgacgtt gtaaaacgac ggccagtctt aagctcgggc    4260
cccaaataat gatttatttt tgactgatag tgacctgttc gttgcaacaa attgatgagc    4320
aatgcttttt tataatgcca actttgtaca aaaaagcagg ctccgaattc gcccttt       4376

<210> SEQ ID NO 24
<211> LENGTH: 5286
<212> TYPE: DNA
<213> ORGANISM: Artificial Sequence
<220> FEATURE:
<223> OTHER INFORMATION: plasmid QC330

<400> SEQUENCE: 24
atcaacaagt ttgtacaaaa aagctgaacg agaaacgtaa aatgatataa atatcaatat      60
attaaattag atttttgcata aaaaacagac tacataatac tgtaaaacac aacatatcca    120
gtcatattgg cggccgcatt aggcacccca ggctttacac tttatgcttc cggctcgtat    180
aatgtgtgga ttttgagtta ggatccgtcg agattttcag gagctaagga agctaaaatg    240
gagaaaaaaa tcactggata taccaccgtt gatatatccc aatggcatcg taaagaacat    300
tttgaggcat ttcagtcagt tgctcaatgt acctataacc agaccgttca gctggatatt    360
acggcctttt taaagaccgt aaagaaaaat aagcacaagt tttatccggc ctttattcac    420
attcttgccc gcctgatgaa tgctcatccg gaattccgta tggcaatgaa agacggtgag    480
ctggtgatat gggatagtgt tcaccttgt tacaccgttt tccatgagca aactgaaacg    540
ttttcatcgc tctggagtga ataccacgac gatttccggc agtttctaca catatattcg    600
caagatgtgg cgtgttacgg tgaaaacctg gcctatttcc ctaaagggtt tattgagaat    660 atgttttttcg tctcagccaa tccctgggtg agtttcacca gttttgattt aaacgtggcc    720
aatatgagca acttcttcgc ccccgttttc accatgggca atattatac gcaaggcgac    780 aaggtgctga tgccgctggc gattcaggtt catcatgccg tttgtgatgg cttccatgtc    840
ggcagaatgc ttaatgaatt acaacagtac tgcgatgagt ggcagggcgg ggcgtaaaga    900
tctggatccg gcttactaaa agccagataa cagtatgcgt atttgcgcgc tgattttttgc   960 ggtataagaa tatatactga tatgtatacc cgaagtatgt caaaaagagg tatgctatga   1020
agcagcgtat tacagtgaca gttgacagcg acagctatca gttgctcaag gcatatatga   1080
tgtcaatatc tccggtctgg taagcacaac catgcagaat gaagcccgtc gtctgcgtgc   1140
cgaacgctgg aaagcggaaa atcaggaagg atggctgag tcgcccggt ttattgaaat    1200 gaacggctct tttgctgacg agaacagggg ctggtgaaat gcagtttaag gtttacacct   1260
ataaaagaga gagccgttat cgtctgtttg tggatgtaca gagtgatatt attgacacgc   1320
ccgggcgacg gatggtgatc ccctggcca gtgcacgtct gctgtcagat aaagtctccc   1380
```

```
gtgaacttta cccggtggtg catatcgggg atgaaagctg gcgcatgatg accaccgata    1440
tggccagtgt gccggtctcc gttatcgggg aagaagtggc tgatctcagc caccgcgaaa    1500
atgacatcaa aaacgccatt aacctgatgt tctggggaat ataaatgtca ggctccctta    1560
tacacagcca gtctgcaggt cgaccatagt gactggatat gttgtgtttt acagtattat    1620
gtagtctgtt ttttatgcaa aatctaattt aatatattga tatttatatc attttacgtt    1680
tctcgttcag ctttcttgta caaagtggtt gatgggatcc atgcccaca gcaagcacgg    1740 cctgaaggag gagatgacca tgaagtacca catggagggc tgcgtgaacg ccacaagtt    1800 cgtgatcacc ggcgagggca tcggctaccc cttcaagggc aagcagacca tcaacctgtg    1860
cgtgatcgag ggcggccccc tgcccttcag cgaggacatc ctgagcgccg gcttcaagta    1920
cggcgaccgg atcttcaccg agtacccca ggacatcgtg gactacttca agaacagctg    1980
ccccgccggc tacacctggg gccggagctt cctgttcgag gacggcgccg tgtgcatctg    2040
taacgtggac atcaccgtga gcgtgaagga gaactgcatc taccacaaga gcatcttcaa    2100
cggcgtgaac ttccccgccg acggcccgt gatgaagaag atgaccacca actgggaggc    2160
cagctgcgag aagatcatgc ccgtgcctaa gcagggcatc ctgaagggcg acgtgagcat    2220
gtacctgctg ctgaaggacg gcggccgta ccggtgccag ttcgacaccg tgtacaaggc    2280
caagagcgtg cccagcaaga tgcccgagtg gcacttcatc cagcacaagc tgctgcggga    2340
ggaccggagc gacgccaaga accagaagtg gcagctgacc gagcacgcca tcgccttccc    2400
cagcgccctg gcctgagagc tcgaatttcc ccgatcgttc aaacatttgg caataaagtt    2460
tcttaagatt gaatcctgtt gccggtcttg cgatgattat catataattt ctgttgaatt    2520
acgttaagca tgtaataatt aacatgtaat gcatgacgtt atttatgaga tgggttttta    2580
tgattagagt cccgcaatta tacatttaat acgcgataga aaacaaaata tagcgcgcaa    2640
actaggataa attatcgcgc gcggtgtcat ctatgttact agatcgggaa ttctagtggc    2700
cggcccagct gatatccatc acactggcgg ccgctcgagt tctatagtgt cacctaaatc    2760
gtatgtgtat gatacataag gttatgtatt aattgtagcc gcgttctaac gacaatatgt    2820
ccatatggtg cactctcagt acaatctgct ctgatgccgc atagttaagc cagccccgac    2880
acccgccaac acccgctgac gcgccctgac gggcttgtct gctcccggca tccgcttaca    2940
gacaagctgt gaccgtctcc gggagctgca tgtgtcagag gttttcaccg tcatcaccga    3000
aacgcgcgag acgaaagggc ctcgtgatac gcctattttt ataggttaat gtcatgacca    3060
aaatccctta acgtgagttt tcgttccact gagcgtcaga ccccgtagaa aagatcaaag    3120
gatcttcttg agatcctttt tttctgcgcg taatctgctg cttgcaaaca aaaaaaccac    3180
cgctaccagc ggtggtttgt ttgccggatc aagagctacc aactcttttt ccgaaggtaa    3240
ctggcttcag cagagcgcag ataccaaata ctgtccttct agtgtagccg tagttaggcc    3300
accacttcaa gaactctgta gcaccgccta catacctcgc tctgctaatc ctgttaccag    3360
tggctgctgc cagtggcgat aagtcgtgtc ttaccgggtt ggactcaaga cgatagttac    3420
cggataaggc gcagcggtcg ggctgaacgg ggggttcgtg cacacagccc agcttggagc    3480
gaacgaccta caccgaactg agatacctac agcgtgagca ttgagaaagc gccacgcttc    3540
ccgaagggag aaaggcggac aggtatccgg taagcggcag gtcggaaca ggagagcgca    3600 cgagggagct tccaggggga aacgcctggt atctttatag tcctgtcggg tttcgccacc    3660
tctgacttga gcgtcgattt ttgtgatgct cgtcaggggg gcggagccta tggaaaaacg    3720
ccagcaacgc ggcctttttta cggttcctgg ccttttgctg gccttttgct cacatgttct    3780
```

```
ttcctgcgtt atcccctgat tctgtggata accgtattac cgcctttgag tgagctgata      3840
ccgctcgccg cagccgaacg accgagcgca gcgagtcagt gagcgaggaa gcggaagagc      3900
gcccaatacg caaaccgcct ctccccgcgc gttggccgat tcattaatgc aggttgatca      3960
gatctcgatc ccgcgaaatt aatacgactc actataggga gaccacaacg gtttccctct      4020
agaaataatt ttgtttaact ttaagaagga gatataccca tggaaaagcc tgaactcacc      4080
gcgacgtctg tcgagaagtt tctgatcgaa aagttcgaca cgtctccga cctgatgcag       4140 ctctcggagg gcgaagaatc tcgtgctttc agcttcgatg taggagggcg tggatatgtc      4200
ctgcgggtaa atagctgcgc cgatggtttc tacaaagatc gttatgttta tcggcacttt      4260
gcatcggccg cgctcccgat tccggaagtg cttgacattg gggaattcag cgagagcctg      4320
acctattgca tctcccgccg tgcacagggt gtcacgttgc aagacctgcc tgaaaccgaa      4380
ctgcccgctg ttctgcagcc ggtcgcggag gctatggatg cgatcgctgc ggccgatctt      4440
agccagacga gcgggttcgg cccattcgga ccgcaaggaa tcggtcaata cactacatgg      4500
cgtgatttca tatgcgcgat tgctgatccc catgtgtatc actggcaaac tgtgatggac      4560
gacaccgtca gtgcgtccgt cgcgcaggct ctcgatgagc tgatgctttg gccgaggac       4620 tgccccgaag tccggcacct cgtgcacgcg gatttcggct ccaacaatgt cctgacggac      4680
aatggccgca taacagcggt cattgactgg agcgaggcga tgttcgggga ttcccaatac      4740
gaggtcgcca acatcttctt ctggaggccg tggttggctt gtatggagca gcagacgcgc      4800
tacttcgagc ggaggcatcc ggagcttgca ggatcgccgc ggctccgggc gtatatgctc      4860
cgcattggtc ttgaccaact ctatcagagc ttggttgacg gcaatttcga tgatgcagct      4920
tgggcgcagg tcgatgcgca cgcaatcgtc cgatccggag ccgggactgt cgggcgtaca      4980
caaatcgccc gcagaagcgc ggccgtctgg accgatggct gtgtagaagt actcgccgat      5040
agtggaaacc gacgccccag cactcgtccg agggcaaagg aatagtgagg tacagcttgg      5100
atcgatccgg ctgctaacaa agcccgaaag gaagctgagt tggctgctgc caccgctgag      5160
caataactag cataaccct tggggcctct aaacgggtct tgaggggttt tttgctgaaa       5220
ggaggaacta tatccggatg atcgtcgagg cctcacgtgt taacaagctt gcatgcctgc      5280
aggttt                                                                5286
```

<210> SEQ ID NO 25
<211> LENGTH: 5217
<212> TYPE: DNA
<213> ORGANISM: Artificial Sequence
<220> FEATURE:
<223> OTHER INFORMATION: plasmid QC532-1Y

<400> SEQUENCE: 25

```
gggagttcac atgctatgaa tccgttatca taaactccaa agccatgatt acaacataaa        60
gagatgttat taaaattgaa ataaataaaa tttgaggctt aggtcctcgt gcacataaac       120
ttgcatgatg atttacagct ctctctccca ctttgagtct tgtggtaatt tgaggtaaat       180
attggatcca actcagcaac tactagtaag cttttctctca aaagaaaaaa aaaaccacta     240
gtaagcttta ttttctagtg aagcaactgc tatagtcttg ggttttggag aaattgtcag      300
gtgtgccatt aaattaagag ttgcgtcgat tatccttacc tttttttatat aaaaaaatat    360 tccatttaat tttgattaaa atatatatta tttcacgaca aaaaaatact cgtgtagatt      420
ctatttatac aaatttgcta gattaagaaa attaagaata gacaaattat aatgtgacat      480
```

```
aaatatttct atgattgctt gaagtaaaat agcaaaaatt agtttaaatt gttttttatat    540 aattcaagta taaaattgtc atattttttct ataaaagtgt caacttttaa tagaatgtgg    600
ttaaatgatg atttctcatt gggtatccat gtaaaaatat tgttgtcatt ttatttgtca    660
tacttttaca caattttttca tgatgtgata taattgataa ataatcttat actttaagta   720
taaaattaga gattgaattc ccaaatataa aaataatatt attgagagag atcaacttct    780
tagataaatc ttgatacttc gagtagcacc ctgacttaaa aaatgtcctt ggtaaatttt    840
tatttattaa tatgatgcgg ttataaagta aattcttatt agataattgt gtaaaaattc    900
atctgttttt tgtttaagaa tgtgtatata gttgattaat ttaatctata taataatttg    960
tacggaaaaa atatactatt tgggaccctg agattattat gtttggtaga atttgggagg   1020
tgggaagatt ggatgttagg tggaacgagg tcaggagacg acacatctgg tcggggaggg   1080
gaggtagaaa aattatacat tgacacaata ggataattgg tacctagtga gataaaattt   1140
taaaaaaata tagatattca tattataggt attatgattt ggtatgaaag agaaaaaaag   1200
aagatgaaaa gtgtttaaaa aataagttta atatttatgc attgaaatca tgatgaatta   1260
tgagtagatg tgtgtttaat gtccatctat catcttcaca gtatgggaca acacaaaagc   1320
aatatgaatg tgatgaccca caattgggcc ctcaagcccc aattcggccc attgggccat   1380 cgaaagaaa aagcatgcgc tgcggatatt aataattttg tgacgctcca ccacaattcc    1440
ccatccccaa aatttctcat tctcccttc ctctccgaac cctcgatcac tctcacgcgc    1500
tcctatattc gctcctccac cgtcgctctc tcgaacaacc acaacaccat cttcatcaca   1560
agggcgaatt cgacccagct ttcttgtaca aagtggttga tgggatccat ggcccacagc   1620
aagcacggcc tgaaggagga gatgaccatg aagtaccaca tggagggctg cgtgaacggc   1680
cacaagttcg tgatcaccgg cgagggcatc ggctacccct tcaagggcaa gcagaccatc   1740
aacctgtgcg tgatcgaggg cggccccctg cccttcagcg aggacatcct gagcgccggc   1800
ttcaagtacg gcgaccggat cttcaccgag taccccagg acatcgtgga ctacttcaag   1860
aacagctgcc ccgccggcta cacctgggc cggagcttcc tgttcgagga cggcgccgtg    1920
tgcatctgta acgtggacat caccgtgagc gtgaaggaga actgcatcta ccacaagagc   1980
atcttcaacg gcgtgaactt ccccgccgac ggccccgtga tgaagaagat gaccaccaac   2040
tgggaggcca gctgcgagaa gatcatgccc gtgcctaagc agggcatcct gaagggcgac   2100
gtgagcatgt acctgctgct gaaggacggc ggccggtacc ggtgccagtt cgacaccgtg   2160
tacaaggcca agagcgtgcc cagcaagatg cccgagtggc acttcatcca gcacaagctg   2220
ctgcgggagg accggagcga cgccaagaac cagaagtggc agctgaccga gcacgccatc   2280
gccttcccca gcgccctggc ctgagagctc gaatttcccc gatcgttcaa acatttggca   2340
ataaagtttc ttaagattga atcctgttgc cggtcttgcg atgattatca tataatttct   2400
gttgaattac gttaagcatg taataattaa catgtaatgc atgacgttat ttatgagatg   2460
ggtttttatg attagagtcc cgcaattata catttaatac gcgatagaaa acaaaatata   2520
gcgcgcaaac taggataaat tatcgcgcgc ggtgtcatct atgttactag atcgggaatt   2580
ctagtggccg gccagctga tatccatcac actggcggcc gctcgagttc tatagtgtca   2640
cctaaatcgt atgtgtatga tacataaggt tatgtattaa ttgtagccgc gttctaacga   2700
caatatgtcc atatggtgca ctctcagtac aatctgctct gatgccgcat agttaagcca    2760
gccccgacac ccgccaacac ccgctgacgc gccctgacgg gcttgtctgc tcccggcatc   2820
cgcttacaga caagctgtga ccgtctccgg gagctgcatg tgtcagaggt tttcaccgtc    2880
```

```
atcaccgaaa cgcgcgagac gaaagggcct cgtgatacgc ctattttat aggttaatgt    2940 catgaccaaa atcccttaac gtgagttttc gttccactga gcgtcagacc ccgtagaaaa    3000
gatcaaagga tcttcttgag atccttttt tctgcgcgta atctgctgct tgcaaacaaa    3060
aaaaccaccg ctaccagcgg tggtttgttt gccggatcaa gagctaccaa ctcttttcc    3120 gaaggtaact ggcttcagca gagcgcagat accaaatact gtccttctag tgtagccgta    3180
gttaggccac cacttcaaga actctgtagc accgcctaca tacctcgctc tgctaatcct    3240
gttaccagtg gctgctgcca gtggcgataa gtcgtgtctt accgggttgg actcaagacg    3300
atagttaccg gataaggcgc agcggtcggg ctgaacgggg ggttcgtgca cacagcccag    3360
cttggagcga acgacctaca ccgaactgag atacctacag cgtgagcatt gagaaagcgc    3420
cacgcttccc gaagggagaa aggcggacag gtatccggta agcggcaggg tcggaacagg    3480
agagcgcacg agggagcttc caggggggaaa cgcctggtat ctttatagtc ctgtcgggtt    3540
tcgccacctc tgacttgagc gtcgattttt gtgatgctcg tcaggggggc ggagcctatg    3600
gaaaaacgcc agcaacgcgg cctttttacg gttcctggcc ttttgctggc cttttgctca    3660
catgttcttt cctgcgttat cccctgattc tgtggataac cgtattaccg cctttgagtg    3720
agctgatacc gctcgccgca gccgaacgac cgagcgcagc gagtcagtga gcgaggaagc    3780
ggaagagcgc ccaatacgca aaccgcctct ccccgcgcgt tggccgattc attaatgcag    3840
gttgatcaga tctcgatccc gcgaaattaa tacgactcac tatagggaga ccacaacggt    3900
ttccctctag aaataattt gtttaacttt aagaaggaga tatacccatg gaaaagcctg    3960
aactcaccgc gacgtctgtc gagaagtttc tgatcgaaaa gttcgacagc gtctccgacc    4020
tgatgcagct ctcggagggc gaagaatctc gtgctttcag cttcgatgta ggagggcgtg    4080
gatatgtcct gcgggtaaat agctgcgccg atggtttcta caaagatcgt tatgtttatc    4140
ggcactttgc atcggccgcg ctcccgattc cggaagtgct tgacattggg gaattcagcg    4200
agagcctgac ctattgcatc tcccgccgtg cacagggtgt cacgttgcaa gacctgcctg    4260
aaaccgaact gcccgctgtt ctgcagccgg tcgcggaggc tatggatgcg atcgctgcgg    4320
ccgatcttag ccagacgagc gggttcggcc cattcggacc gcaaggaatc ggtcaataca    4380
ctacatggcg tgatttcata tgcgcgattg ctgatcccca tgtgtatcac tggcaaactg    4440
tgatggacga caccgtcagt gcgtccgtcg cgcaggctct cgatgagctg atgctttggg    4500
ccgaggactg ccccgaagtc cggcacctcg tgcacgcgga tttcggctcc aacaatgtcc    4560
tgacggacaa tggccgcata acagcggtca ttgactggag cgaggcgatg ttcgggatt    4620 cccaatacga ggtcgccaac atcttcttct ggaggccgtg gttggcttgt atggagcagc    4680
agacgcgcta cttcgagcgg aggcatccgg agcttgcagg atcgccgcgg ctccgggcgt    4740
atatgctccg cattggtctt gaccaactct atcagagctt ggttgacggc aatttcgatg    4800
atgcagcttg ggcgcagggt cgatgcgacg caatcgtccg atccggagcc gggactgtcg    4860
ggcgtacaca atcgcccgc agaagcgcgg ccgtctggac cgatggctgt gtagaagtac    4920
tcgccgatag tggaaaccga cgccccagca ctcgtccgag ggcaaaggaa tagtgaggta    4980
cagcttggat cgatccggct gctaacaaag cccgaaagga agctgagttg gctgctgcca    5040
ccgctgagca ataactagca taaccccttg gggcctctaa acgggtcttg agggggtttt    5100
tgctgaaagg aggaactata tccggatgat cgtcgaggcc tcacgtgtta acaagcttgc    5160
atgcctgcag gtttatcaac aagtttgtac aaaaaagcag gctccgaatt cgcccctt    5217
```

```
<210> SEQ ID NO 26
<211> LENGTH: 22
<212> TYPE: DNA
<213> ORGANISM: Artificial Sequence
<220> FEATURE:
<223> OTHER INFORMATION: SAMS forward primer: (SAMS-76F

<400> SEQUENCE: 26
aggcttgttg tgcagttttt ga                                              22

<210> SEQ ID NO 27
<211> LENGTH: 22
<212> TYPE: DNA
<213> ORGANISM: Artificial Sequence
<220> FEATURE:
<223> OTHER INFORMATION: FAM labeled ALS probe: (ALS-100T

<400> SEQUENCE: 27
ccacacaaca caatggcggc ca                                              22

<210> SEQ ID NO 28
<211> LENGTH: 22
<212> TYPE: DNA
<213> ORGANISM: Artificial Sequence
<220> FEATURE:
<223> OTHER INFORMATION: ALS reverse primer: (ALS-163R)

<400> SEQUENCE: 28
ggaagaagag aatcgggtgg tt                                              22

<210> SEQ ID NO 29
<211> LENGTH: 24
<212> TYPE: DNA
<213> ORGANISM: Artificial Sequence
<220> FEATURE:
<223> OTHER INFORMATION: GFP forward primer: (GFP-24F)

<400> SEQUENCE: 29
gaccaaggag atgaccatga agta                                            24

<210> SEQ ID NO 30
<211> LENGTH: 14
<212> TYPE: DNA
<213> ORGANISM: Artificial Sequence
<220> FEATURE:
<223> OTHER INFORMATION: FAM labeled GFP probe: (GFP-51T

<400> SEQUENCE: 30
catggagggc tgcg                                                       14

<210> SEQ ID NO 31
<211> LENGTH: 20
<212> TYPE: DNA
<213> ORGANISM: Artificial Sequence
<220> FEATURE:
<223> OTHER INFORMATION: GFP reverse primer: (GFP-92R)

<400> SEQUENCE: 31
ccggtgatca cgaacttgtg                                                 20

<210> SEQ ID NO 32
<211> LENGTH: 24
<212> TYPE: DNA
<213> ORGANISM: Artificial Sequence
<220> FEATURE:
<223> OTHER INFORMATION: HSP forward primer: (HSP-F1)
```

<400> SEQUENCE: 32
caaacttgac aaagccacaa ctct                                           24

<210> SEQ ID NO 33
<211> LENGTH: 20
<212> TYPE: DNA
<213> ORGANISM: Artificial Sequence
<220> FEATURE:
<223> OTHER INFORMATION: VIC labeled HSP probe: (HSP probe)

<400> SEQUENCE: 33
ctctcatctc atataaatac                                                20

<210> SEQ ID NO 34
<211> LENGTH: 21
<212> TYPE: DNA
<213> ORGANISM: Artificial Sequence
<220> FEATURE:
<223> OTHER INFORMATION: HSP reverse primer: (HSP-R1)

<400> SEQUENCE: 34
ggagaaattg gtgtcgtgga a                                              21

<210> SEQ ID NO 35
<211> LENGTH: 100
<212> TYPE: DNA
<213> ORGANISM: Artificial Sequence
<220> FEATURE:
<223> OTHER INFORMATION: attL1

<400> SEQUENCE: 35
caaataatga ttttattttg actgatagtg acctgttcgt tgcaacaaat tgataagcaa    60
tgctttttta taatgccaac tttgtacaaa aaagcaggct                         100

<210> SEQ ID NO 36
<211> LENGTH: 100
<212> TYPE: DNA
<213> ORGANISM: Artificial Sequence
<220> FEATURE:
<223> OTHER INFORMATION: attL2;

<400> SEQUENCE: 36
caaataatga ttttattttg actgatagtg acctgttcgt tgcaacaaat tgataagcaa    60
tgctttctta taatgccaac tttgtacaag aaagctgggt                         100

<210> SEQ ID NO 37
<211> LENGTH: 125
<212> TYPE: DNA
<213> ORGANISM: Artificial Sequence
<220> FEATURE:
<223> OTHER INFORMATION: attR1

<400> SEQUENCE: 37
acaagtttgt acaaaaaagc tgaacgagaa acgtaaaatg atataaatat caatatatta    60
aattagattt tgcataaaaa acagactaca taatactgta aaacacaaca tatccagtca   120
ctatg                                                              125

<210> SEQ ID NO 38
<211> LENGTH: 125
<212> TYPE: DNA
<213> ORGANISM: Artificial Sequence
<220> FEATURE:

<223> OTHER INFORMATION: attR2

<400> SEQUENCE: 38

```
accactttgt acaagaaagc tgaacgagaa acgtaaaatg atataaatat caatatatta      60
aattagattt tgcataaaaa acagactaca taatactgta aaacacaaca tatccagtca     120
ctatg                                                                 125
```

<210> SEQ ID NO 39
<211> LENGTH: 21
<212> TYPE: DNA
<213> ORGANISM: Artificial Sequence
<220> FEATURE:
<223> OTHER INFORMATION: attB1

<400> SEQUENCE: 39

```
caagtttgta caaaaaagca g                                                21
```

<210> SEQ ID NO 40
<211> LENGTH: 21
<212> TYPE: DNA
<213> ORGANISM: Artificial Sequence
<220> FEATURE:
<223> OTHER INFORMATION: attB2

<400> SEQUENCE: 40

```
ccactttgta caagaaagct g                                                21
```

<210> SEQ ID NO 41
<211> LENGTH: 1025
<212> TYPE: DNA
<213> ORGANISM: Glycine max

<400> SEQUENCE: 41

```
acagacaacc ctcgatcact cccacgcgct cctatatcct ctccttcacc gtcgctctct      60
ccaacgatca caacaacatc gtcatcccat ggcaaacgcc gcatctggta tggcagtcca     120
tgatgactgc aagttaaggt ttttggagct gaagacaaag aggacacacc gtttcatagt     180
ttttaagatt gaggagcagc agaagcaggt cattgtggag aagcttggtg agccagccca     240
aggctatgaa gatttcactg ccagccttcc tgctgatgag tgccgttatg ctgtttatga     300
ttttgagtat ctgactgaag ggaatgtccc taaaagcaga attttttttca ttgcatggtc     360
ccctgacaca tcaagggtga ggagcaagat gatctatgca agctccaaag acagattcaa     420
gagggagctg gatggaattc aagtagagct gcaagcaact gatcctactg agatgggtct     480
tgatgtgttc aaaagccggg ccaactaaaa tgattataga aaatagtagg ctttctggtg     540
ggagcagcac tccttaagcc ttagttactc atggaaaata tcctagtttg tgggatggtc     600
aacttgggta gttatggtcc caaactctct caattttcca agtgtggca taaattctat     660
tgcacctttt aacaagcttt gcttgttcca gtgtgtttta ttatgatttg tgatttatac     720
aaccttgcgt ttgagtgcca ttttagtcgt cttatccctt actagttgaa tttgtaactg     780
tttgtgttat cagacaaaaa atggggtttc ttcacttatt gacactcgtc atccactaat     840
gttttgtgac ttgttctggc cgatatatgc tttcttttgt atgggcatac aaaggcatct     900
tgttcatgct atattccttt tttgttttat ggtttggtgg aatgagattt tattcaactg     960
gttgattgtt cttgaaacca gagtgtactt cattcgtagc aatagcatct aagcggttta    1020
tggtc                                                                1025
```

<210> SEQ ID NO 42
<211> LENGTH: 801
<212> TYPE: DNA
<213> ORGANISM: Glycine max

<400> SEQUENCE: 42

```
ggattcccaa aatttctcat tctccctttc ctctccgaac cctcgatcac tctcacgcgc    60
tcctatattc gctcctccac cgtcgctctc tcgaacaacc acaacaccat cttcatcaca   120
tggcaaacgc agcatctggt atggcagtcc atgatgactg caagttgagg ttttttggagc  180
tgaaggcaaa aaggacacac cgtttcatag ttttttaagat tgaggagcag cagaagcagg  240
tcattgtgga gaagcttggt gagcctgccc agggctatga agatttcact gccagccttc   300
ctgctgacga gtgccgttat gctgtttatg attttgagta tctgactgaa gggaatgtcc   360
ctaaaagcag aattttttc attgcgtggt cccctgacac atcaagggtg aggagcaaga   420
tgatttatgc aagctccaaa gacagattca gagggagct ggatggaatt caagtagagt    480
tgcaagcaac tgatcctact gagatgggtc ttgatgtgtt caaaagccgt gccaactaaa   540
atgattatat aaaatagtag ctttctggt gggagcagca cccctgaagc cttagttact    600
catatggaaa atatcctagt ttgtgggatg gtcaacttgg gtagttatgg tcccaaactc   660
tcaatttcc aagttgtggc ataaaattct attgcacctt ttgacaagct ttgcttgttc    720
cagtgtgttt tattatgatt tgtgatttat acaacctttg cgtttgagtg ccatttagt   780
cgtcttatcc cttactagtt g                                             801
```

<210> SEQ ID NO 43
<211> LENGTH: 1501
<212> TYPE: DNA
<213> ORGANISM: Glycine max

<400> SEQUENCE: 43

```
ggagttcaca tgctatgaat ccgttatcat aaactccaaa gccatgatta caacataaag    60
agatgttatt aaaattgaaa taaataaaat ttgaggctta ggtcctcgtg cacataaact   120
tgcatgatga tttacagctc tctctcccac tttgagtctt gtggtaattt gaggtaaata   180
ttggatccaa ctcagcaact actagtaagc tttctctcaa agaaaaaaa aaaaaccact    240
agtaagcttt attttctagt gaagcaactg ctatagtctt gggttttgga gaaattgtca   300
ggtgtgccat taaattaaga gttgcgtcga ttatccttac cttttttata taaaaaaata   360
ttccatttaa ttttgattaa aatatatatt atttcacgac aaaaaaaata ctcgtgtaga   420
ttctatttat acaaatttgc tagattaaga aaattaagaa tagacaaatt ataatgtgac   480
ataaatattt ctatgattgc ttgaagtaaa atagcaaaaa ttagtttaaa ttgttttttat   540
ataattcaag tataaaattg atatatttt ctataaaagt gtcaacttt attttgtcata    600
cttttacaca atttttcatg atgtgatata attgataaat aatcttatac tttaagtata   660
aaattagaga ttgaattccc aaatataaaa ataattattat tgagagagat caacttctta   720
gataaatctt gatacttcga gtagcaccct gacttaaaaa atgtccttgg taaattttta   780
tttattaata tgatgcggtt ataaagtaaa ttcttattag ataattgtgt aaaaattcat   840
ctgtttttta tttaagaatg tgtatatagt tgattaattt aatctatata ataatttgta   900
cggaaaaaat atactatttg ggaccctgag attattatgt ttggtagaat ttgggaggtg   960
ggaagattgg atgttaggtg gaacgaggtc aggagacgac acatctggtc ggggagggga  1020
ggtagaaaaa ttatacattg acacaatagg ataattggta cctagtgaga taaaatttta  1080
```

```
aaaaaatata gatattcata ttataggtat tatgatttgg tatgaaagag aaaaaaagaa    1140
gatgaaaagt gtttaaaaaa taagtttaat atttatgcat tgaaatcatg atgaattatg    1200
agtagatgtg tgtttaatgt ccatctatca tcttcacagt atgggacaac acaaaagcaa    1260
tatgaatgtg atggaccaca attgggccct caagccccaa ttcggcccat tgggcaatcg    1320
aaaagaaaaa gcatgcgctg cggatattaa taattttgtg acgctccacc acaattcccc    1380
attcccaaaa tttctcattc tcoctttcct ctccgaaccc tcgatcactc tcacgcgctc    1440
ctatattcgc tcctccaccg tcgctctctc gaacaaccac aacaccatct tcatcacatg    1500
g                                                                   1501

<210> SEQ ID NO 44
<211> LENGTH: 128
<212> TYPE: DNA
<213> ORGANISM: Glycine max

<400> SEQUENCE: 44
cacaattccc catcccaaa atttctcatt ctcoctttcc tctccgaacc ctcgatcact      60
ctcacgcgct cctatattcg ctcctccacc gtcgctctct cgaacaacca caacaccatc    120
ttcatcac                                                             128
```

SOYBEAN ADF1 PROMOTER AND ITS USE IN CONSTITUTIVE EXPRESSION OF TRANSGENIC GENES IN PLANTS

This application claims the benefit of U.S. Provisional Application No. 61/681,751, filed Aug. 10, 2012, the entire content of which is herein incorporated by reference.

FIELD OF THE INVENTION

This invention relates to a plant promoter GM-ADF1 and fragments thereof and their use in altering expression of at least one heterologous nucleotide sequence in plants in a tissue-independent or constitutive manner.

BACKGROUND OF THE INVENTION

Recent advances in plant genetic engineering have opened new doors to engineer plants to have improved characteristics or traits, such as plant disease resistance, insect resistance, herbicidal resistance, yield improvement, improvement of the nutritional quality of the edible portions of the plant, and enhanced stability or shelf-life of the ultimate consumer product obtained from the plants. Thus, a desired gene (or genes) with the molecular function to impart different or improved characteristics or qualities, can be incorporated properly into the plant's genome. The newly integrated gene (or genes) coding sequence can then be expressed in the plant cell to exhibit the desired new trait or characteristics. It is important that appropriate regulatory signals must be present in proper configurations in order to obtain the expression of the newly inserted gene coding sequence in the plant cell. These regulatory signals typically include a promoter region, a 5' non-translated leader sequence and a 3' transcription termination/polyadenylation sequence.

A promoter is a non-coding genomic DNA sequence, usually upstream (5') to the relevant coding sequence, to which RNA polymerase binds before initiating transcription. This binding aligns the RNA polymerase so that transcription will initiate at a specific transcription initiation site. The nucleotide sequence of the promoter determines the nature of the RNA polymerase binding and other related protein factors that attach to the RNA polymerase and/or promoter, and the rate of RNA synthesis. The RNA is processed to produce messenger RNA (mRNA) which serves as a template for translation of the RNA sequence into the amino acid sequence of the encoded polypeptide. The 5' non-translated leader sequence is a region of the mRNA upstream of the coding region that may play a role in initiation and translation of the mRNA. The 3' transcription termination/polyadenylation signal is a non-translated region downstream of the coding region that functions in the plant cell to cause termination of the RNA synthesis and the addition of polyadenylate nucleotides to the 3' end.

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Certain promoters are able to direct RNA synthesis at relatively similar levels across all tissues of a plant. These are called "constitutive promoters" or "tissue-independent" promoters. Constitutive promoters can be divided into strong, moderate and weak according to their effectiveness to direct RNA synthesis. Since it is necessary in many cases to simultaneously express a chimeric gene (or genes) in different tissues of a plant to get the desired functions of the gene (or genes), constitutive promoters are especially useful in this consideration. Though many constitutive promoters have been discovered from plants and plant viruses and characterized, there is still an ongoing interest in the isolation of more novel constitutive promoters which are capable of controlling the expression of a chimeric gene or (genes) at different levels and the expression of multiple genes in the same transgenic plant for gene stacking.

SUMMARY OF THE INVENTION

This invention concerns an isolated polynucleotide comprising a promoter wherein said promoter comprises the nucleotide sequence set forth in SEQ ID NOs: 1, 2, 3, 4, 5, 6, 7 or 43 or said promoter comprises a functional fragment of the nucleotide sequence set forth in SEQ ID NOs: 1, 2, 3, 4, 5, 6, 7 or 43, or wherein said promoter comprises a nucleotide sequence having at least 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of SEQ ID NO:1, 2, 3, 4, 5, 6, 7 or 43.

In a second embodiment, the invention concerns an isolated polynucleotide comprising a promoter region of the plasma membrane intrinsic protein (ADF1) *Glycine max* gene as set forth in SEQ ID NO:1, wherein said promoter comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 100 6, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 12312, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 13013, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354 or 1355 consecutive nucleotides, wherein the first nucleotide deleted is the cytosine nucleotide ['C'] at position 1 of SEQ ID NO:1. This invention also concerns an isolated polynucleotide of the embodiments disclosed herein, wherein the polynucleotide is a constitutive promoter.

In a third embodiment, this invention concerns a recombinant DNA construct comprising at least one heterologous nucleotide sequence operably linked to the promoter of the invention.

In a fourth embodiment, this invention concerns a cell, plant, or seed comprising a recombinant DNA construct of the present disclosure.

In a fifth embodiment, this invention concerns plants comprising this recombinant DNA construct and seeds obtained from such plants.

In a sixth embodiment, this invention concerns a method of altering (increasing or decreasing) expression of at least one heterologous nucleic acid fragment in a plant cell which comprises:
(a) transforming a plant cell with the recombinant expression construct described above;
(b) growing fertile mature plants from the transformed plant cell of step (a);
(c) selecting plants containing the transformed plant cell wherein the expression of the heterologous nucleic acid fragment is increased or decreased.

In a seventh embodiment, this invention concerns a method for expressing a yellow fluorescent protein ZS-GREEN1 (GFP) in a host cell comprising:
(a) transforming a host cell with a recombinant expression construct comprising at least one ZS-GREEN1 nucleic acid fragment operably linked to a promoter wherein said promoter consists essentially of the nucleotide sequence set forth in SEQ ID NOs:1, 2, 3, 4, 5, 6, 7 or 43; and
(b) growing the transformed host cell under conditions that are suitable for expression of the recombinant DNA construct, wherein expression of the recombinant DNA construct results in production of increased levels of ZS-GREEN1 protein in the transformed host cell when compared to a corresponding nontransformed host cell.

In an eighth embodiment, this invention concerns an isolated nucleic acid fragment comprising a plant actin depolymerizing factor (ADF1) gene promoter.

In a ninth embodiment, this invention concerns a method of altering a marketable plant trait. The marketable plant trait concerns genes and proteins involved in disease resistance, herbicide resistance, insect resistance, carbohydrate metabolism, fatty acid metabolism, amino acid metabolism, plant development, plant growth regulation, yield improvement, drought resistance, cold resistance, heat resistance, and salt resistance.

In a tenth embodiment, this invention concerns an isolated polynucleotide linked to a heterologous nucleotide sequence. The heterologous nucleotide sequence encodes a protein involved in disease resistance, herbicide resistance, insect resistance; carbohydrate metabolism, fatty acid metabolism, amino acid metabolism, plant development, plant growth regulation, yield improvement, drought resistance, cold resistance, heat resistance, or salt resistance in plants.

BRIEF DESCRIPTION OF THE DRAWINGS AND SEQUENCE LISTINGS

The invention can be more fully understood from the following detailed description and the accompanying drawings and Sequence Listing that form a part of this application.

FIG. 1 is the relative expression of the soybean actin depolymerizing factor (ADF1) gene (PSO315053, Glyma15g13140.1) in twenty one soybean tissues by Illumina (Solexa) digital gene expression dual-tag-based mRNA profiling. The gene expression profile indicates that the ADF1 gene is expressed similarly in all the checked tissues.

Figure 2A:
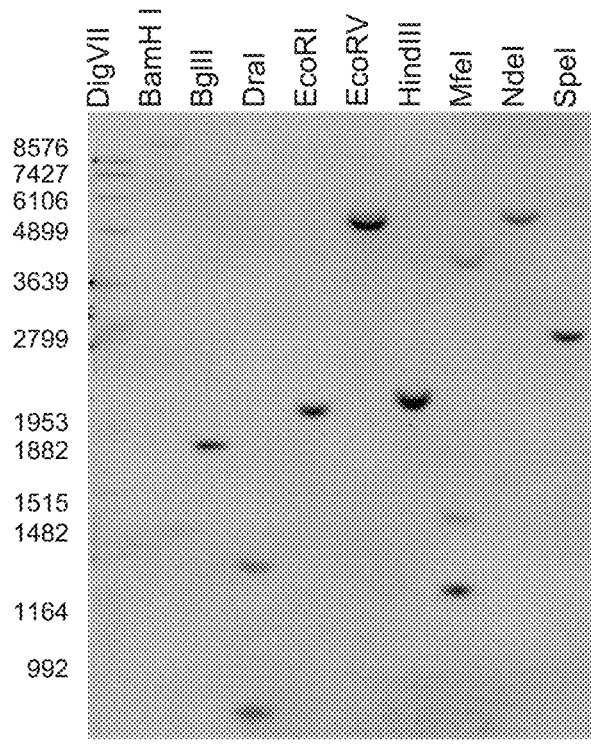
Figure 2B:
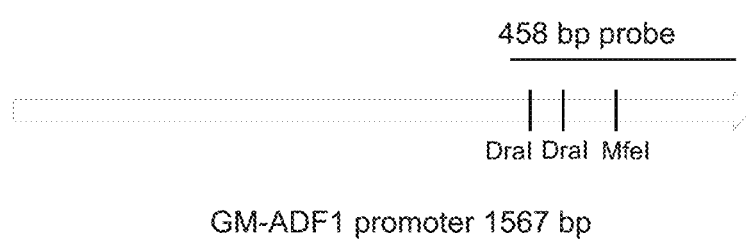

FIG. 2 is ADF1 promoter copy number analysis by Southern. FIG. 2A is the image of a Southern blot hybridized with a 458 bp ADF1 promoter probe made with primers QC532-S5 and QC532-A by PCR. FIG. 2B shows restriction enzyme recognitions sites in the ADF1 probe region.

Figure 3A:
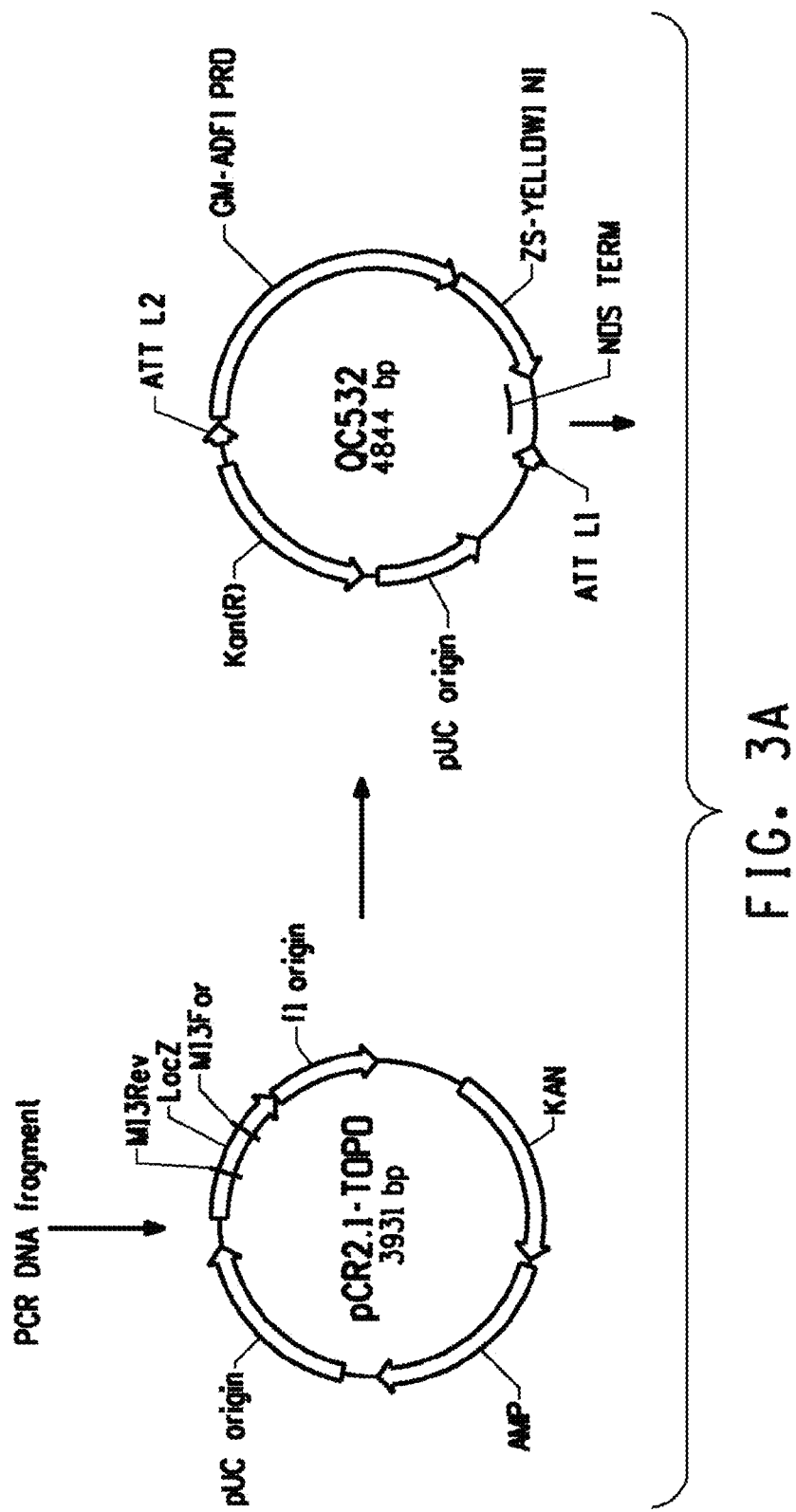
Figure 3B:
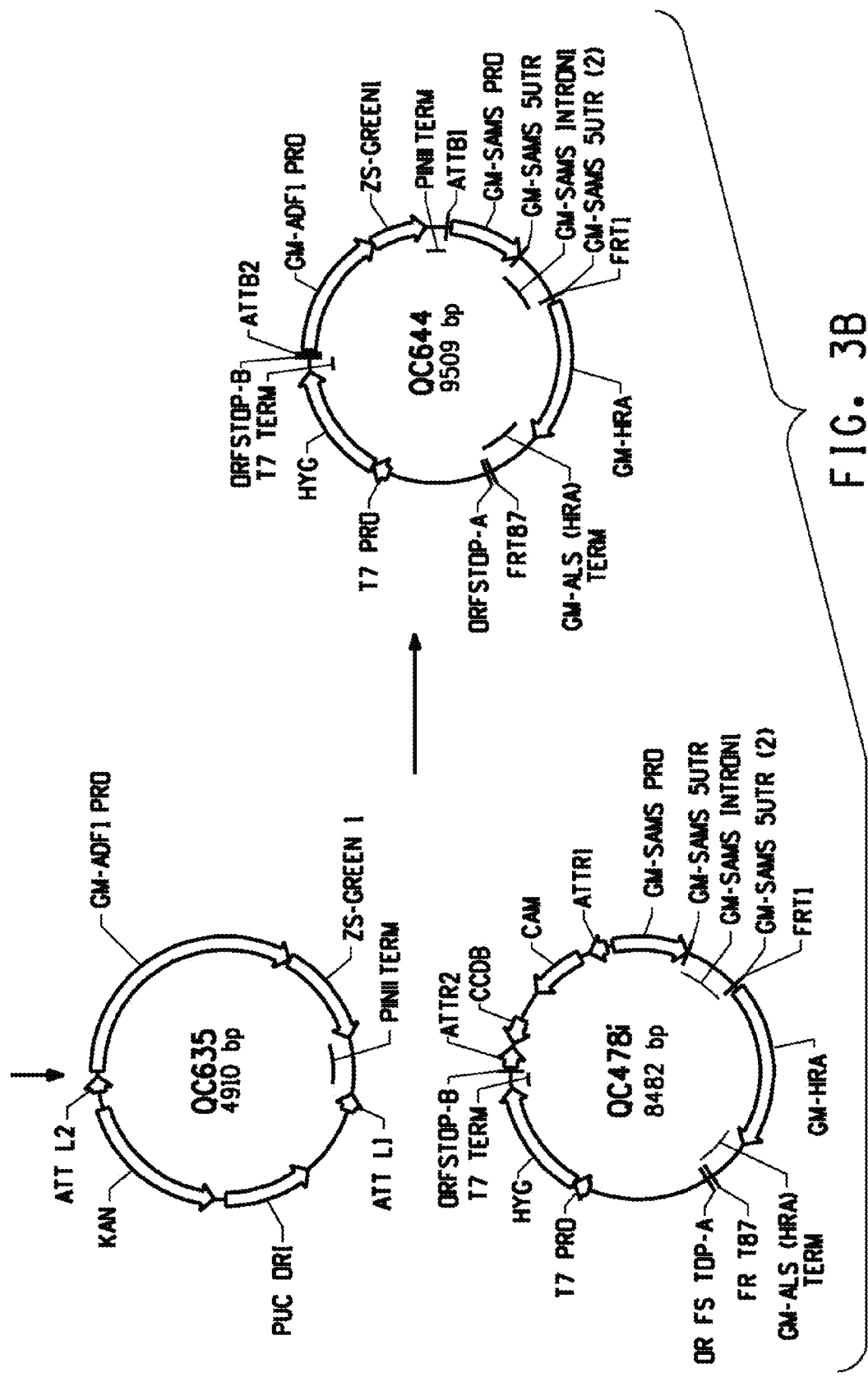

FIG. 3A-3B shows the maps of plasmids pCR2.1-TOPO, QC532, QC635, QC478i, and QC644. The 6995 bp AscI-AscI fragment of QC644 is used to produce transgenic soybean plants.

Figure 4A:
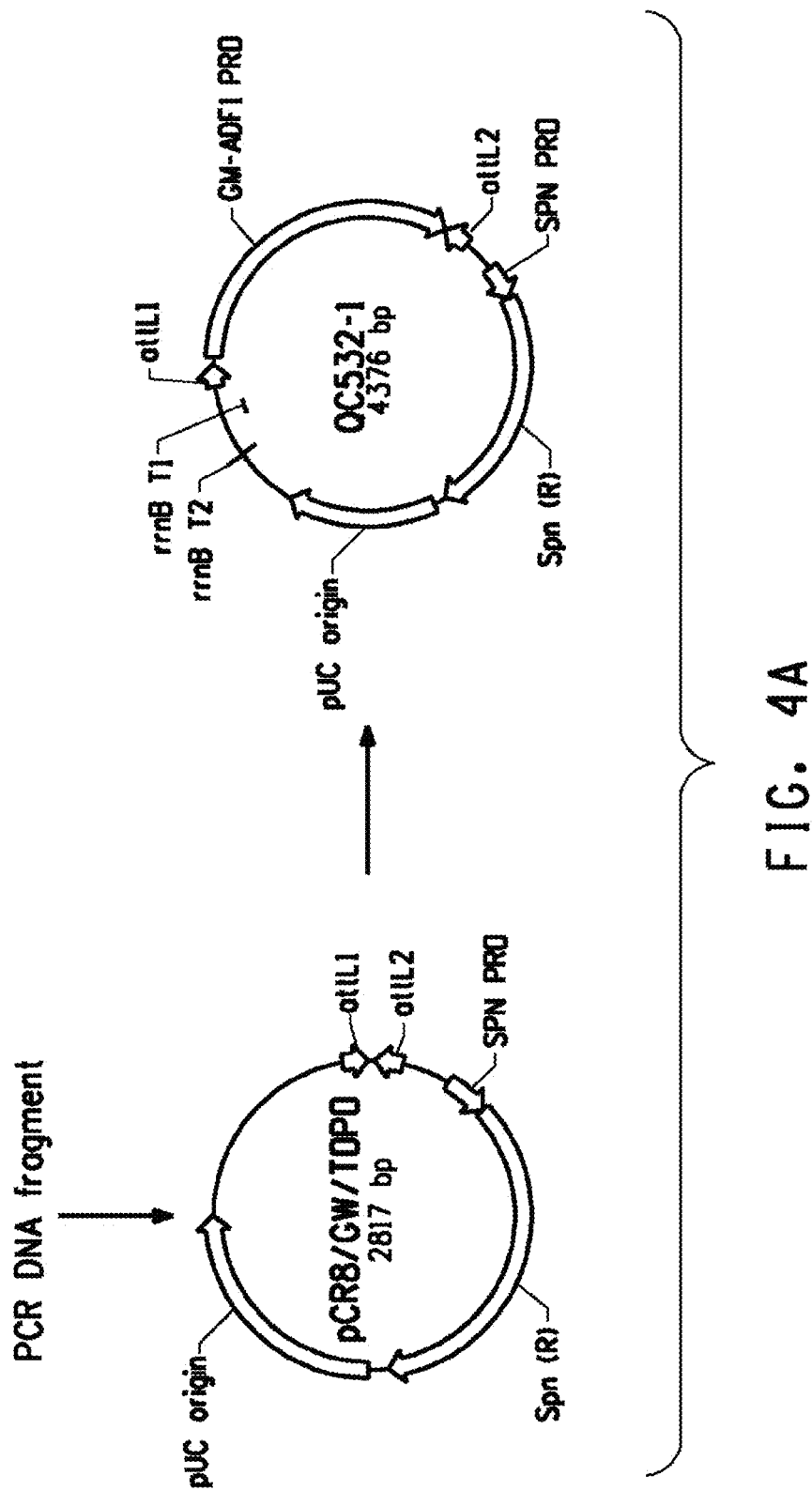
Figure 4B:
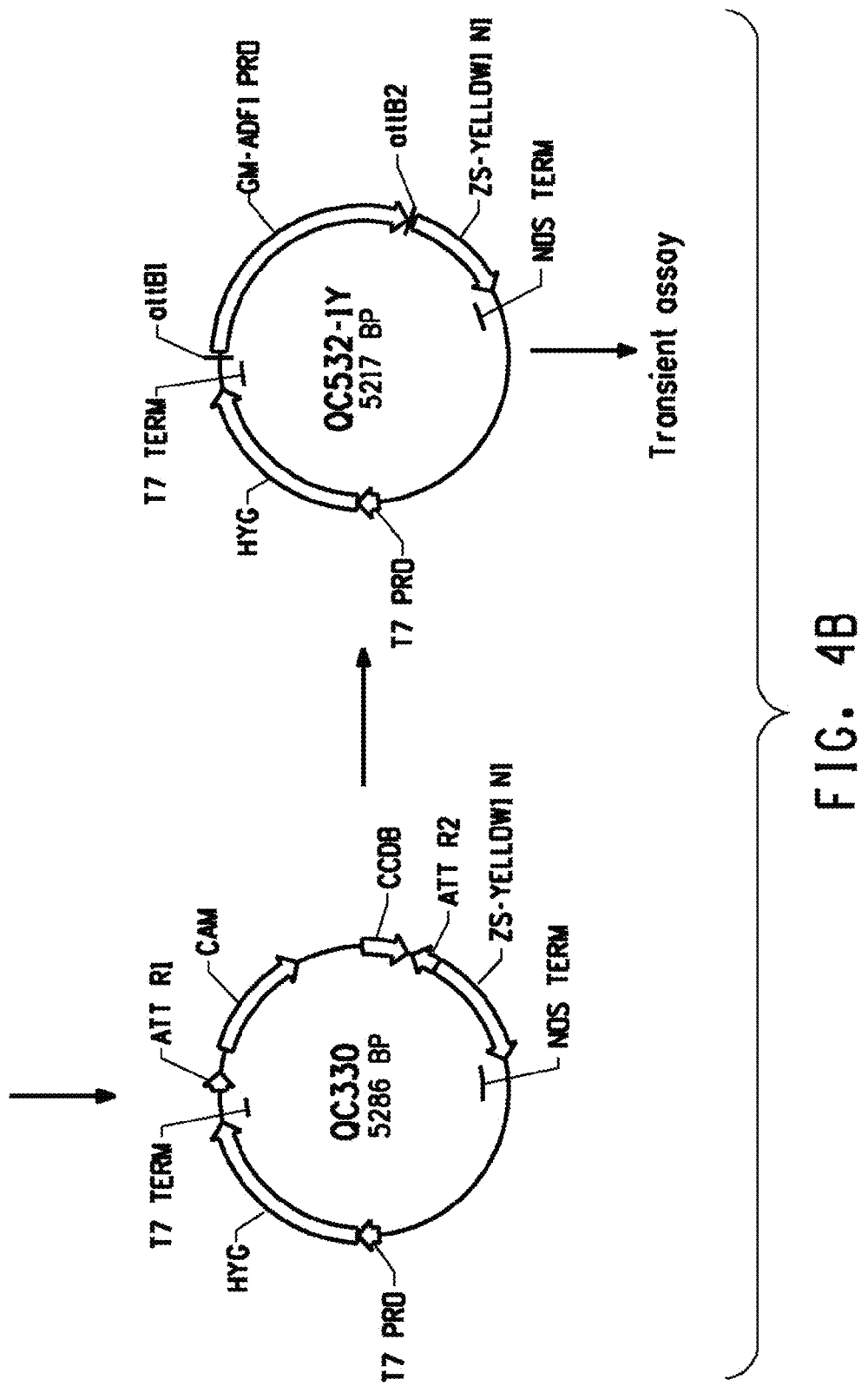
Figure 4C:
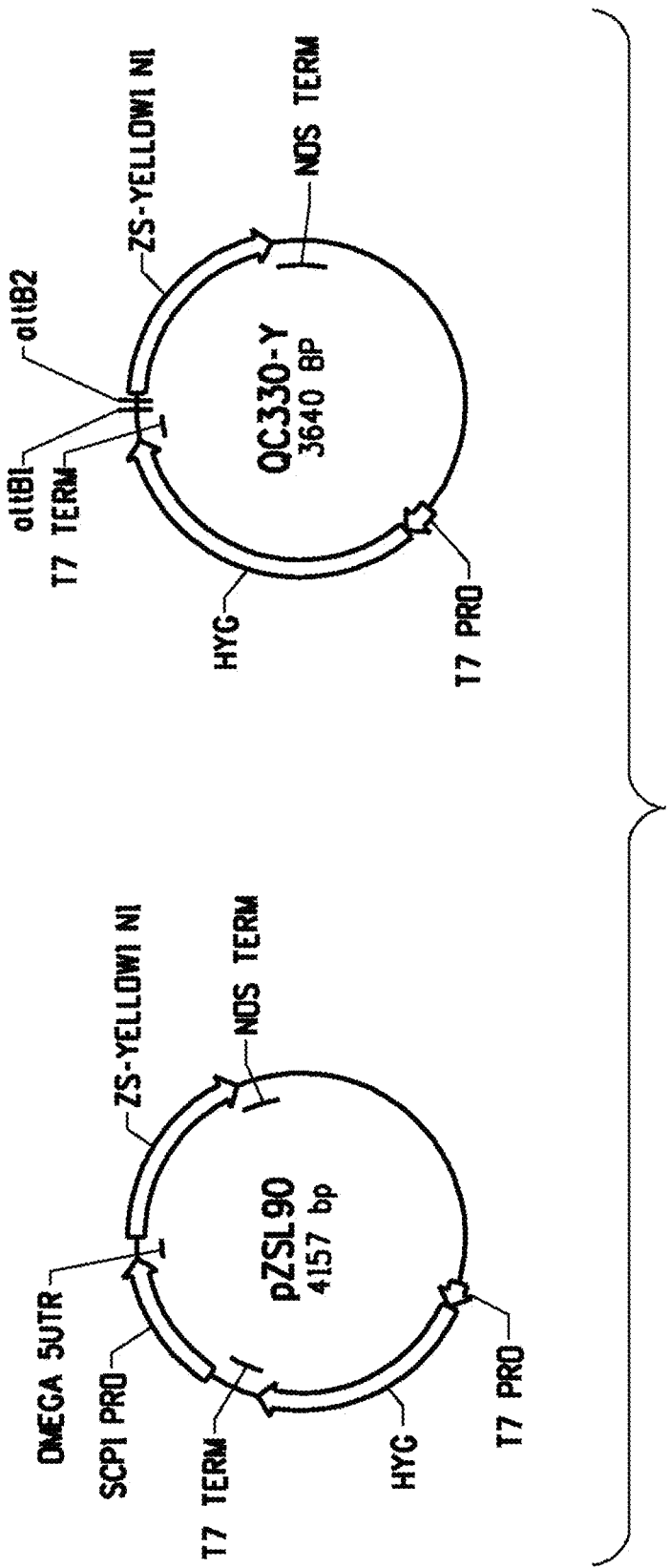

FIG. 4A-4B shows the maps of plasmids pCR8/GW/TOPO, QC532-1, QC330, and QC532-1Y containing a full length 1559 bp ADF1 promoter. Other promoter deletion constructs QC532-2Y, QC532-3Y, QC532-4Y, and QC532-5Y containing the 1243, 985, 770, 458, and 212 bp truncated ADF1 promoters, respectively, have the same map configuration, except for the truncated promoter sequences. FIG. 4C shows the maps of plasmids pZSL90 as a strong constitutive promoter (SCP1) positive control and QC330-Y as a promoter-less negative control in transient expression assays.

Figure 5:
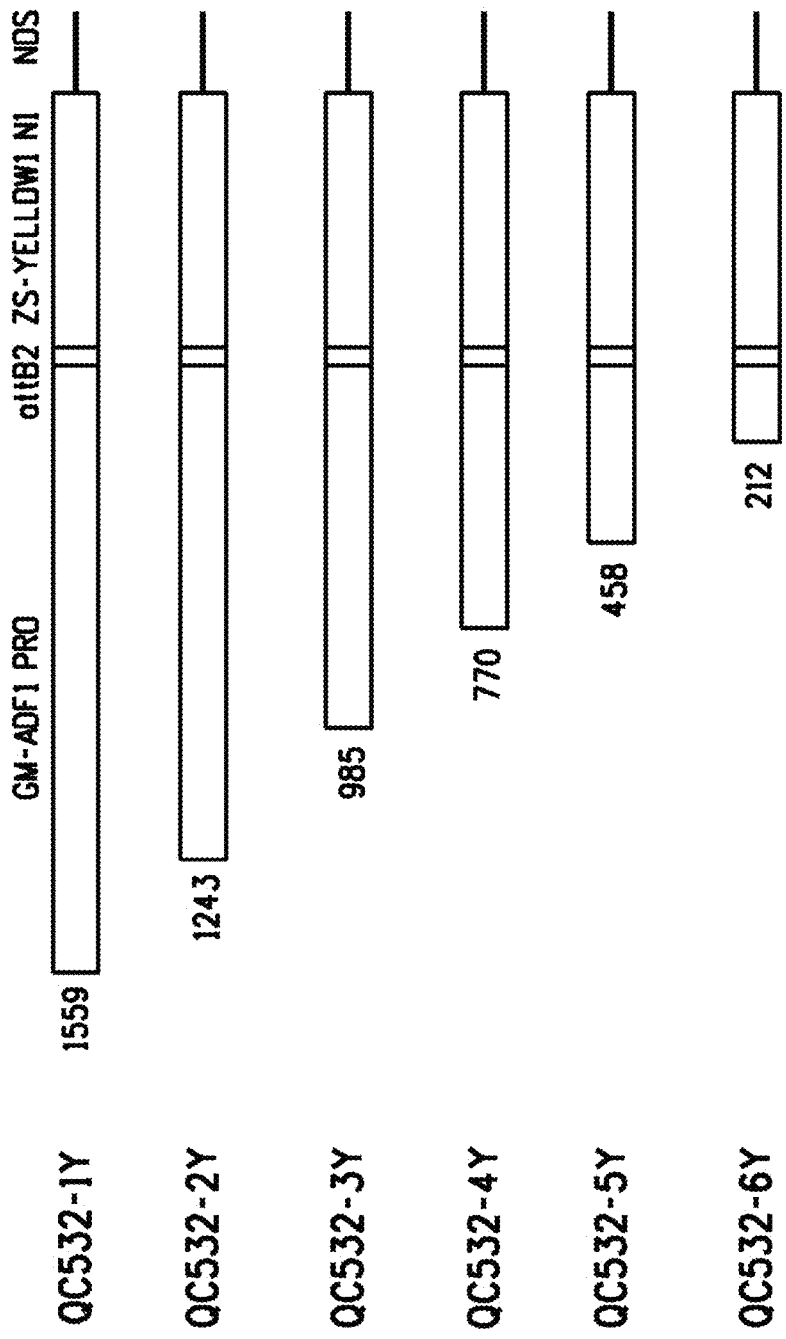

FIG. 5 is the schematic descriptions of the full length ADF1 promoter (QC532-1Y) and its progressive truncations in constructs QC532-1Y, QC532-2Y, QC532-3Y, QC532-4Y, QC532-5Y, and QC532-6Y, of the ADF1 promoter. The size of each promoter is given at the left end of each drawing. QC532-1Y has 1559 bp of the 1567 bp ADF1 promoter in QC532 with the XmaI and NcoI sites removed and like the other deletion constructs with the attB site between the promoter and ZS-YELLOW N1 reporter gene.

FIGS. 6A-6H show the transient expression of the fluorescent protein reporter gene ZS-YELLOW1 N1 in the cotyledons of germinating soybean seeds. FIG. 6A shows the expression of pZSL90. FIG. 6B shows the expression of QCC330-Y. The reporter gene is driven by the full length ADF1 promoter in QC532-1Y (FIG. 6C) or by progressively truncated ADF1 promoters in the transient expression constructs QC532-2Y (FIG. 6D), QC532-3Y (FIG. 6E), QC532-4Y (FIG. 6F), QC532-5Y (FIG. 6G) and QC532-6Y (FIG. 6H).

Figure 7I:
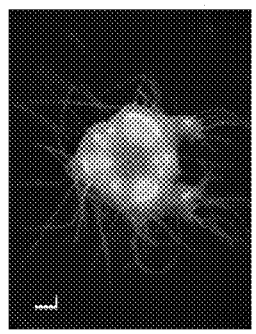
Figure 7J:
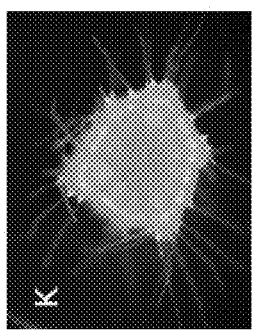
Figure 7K:
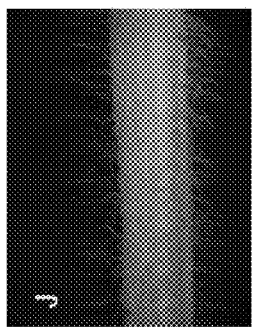
Figure 7L:
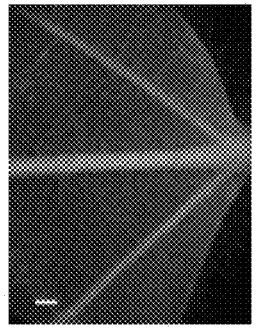
Figure 7M:
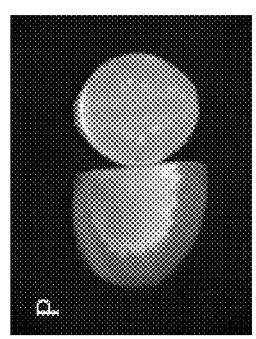
Figure 7N:
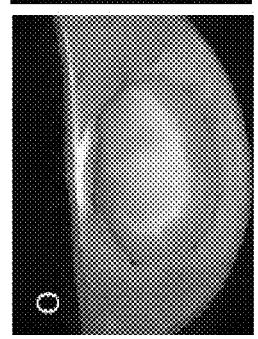
Figure 7O:
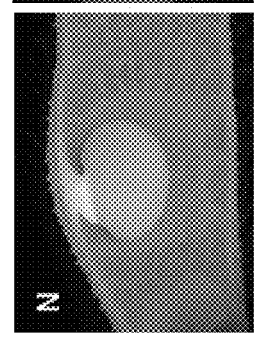
Figure 7P:
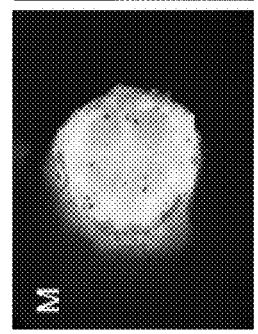

FIG. 7A-7P shows the stable expression of the fluorescent protein reporter gene ZS-GREEN1 in different tissues of transgenic soybean plants containing a single copy of ADF1:GFP DNA of construct QC644, comprising the 1567 bp ADF1 promoter of SEQ ID NO:1. (A: Embryonic callus, B: Young somatic embryos, C: Early cotyledon somatic embryos, D: Mature somatic embryos, E: Flower bud showing pedals and sepals, F: Open flower, G: Stamen, filaments and anthers, H: Longitudinal section of ovary showing ovules, I: Leaf, abaxial surface showing veins, J: Stem, K: Stem, longitudinal section showing vascular bundles, L: Petiole, cross section showing vascular bundles, M: Root, cross section showing vascular bundles, N: Young pod, open showing inner surface and a R3 seed, O: Filled pod, open showing inner surface and a R5 seed, P: Cross section of a R5 seed showing embryo and seed coat)

Figure 8A:
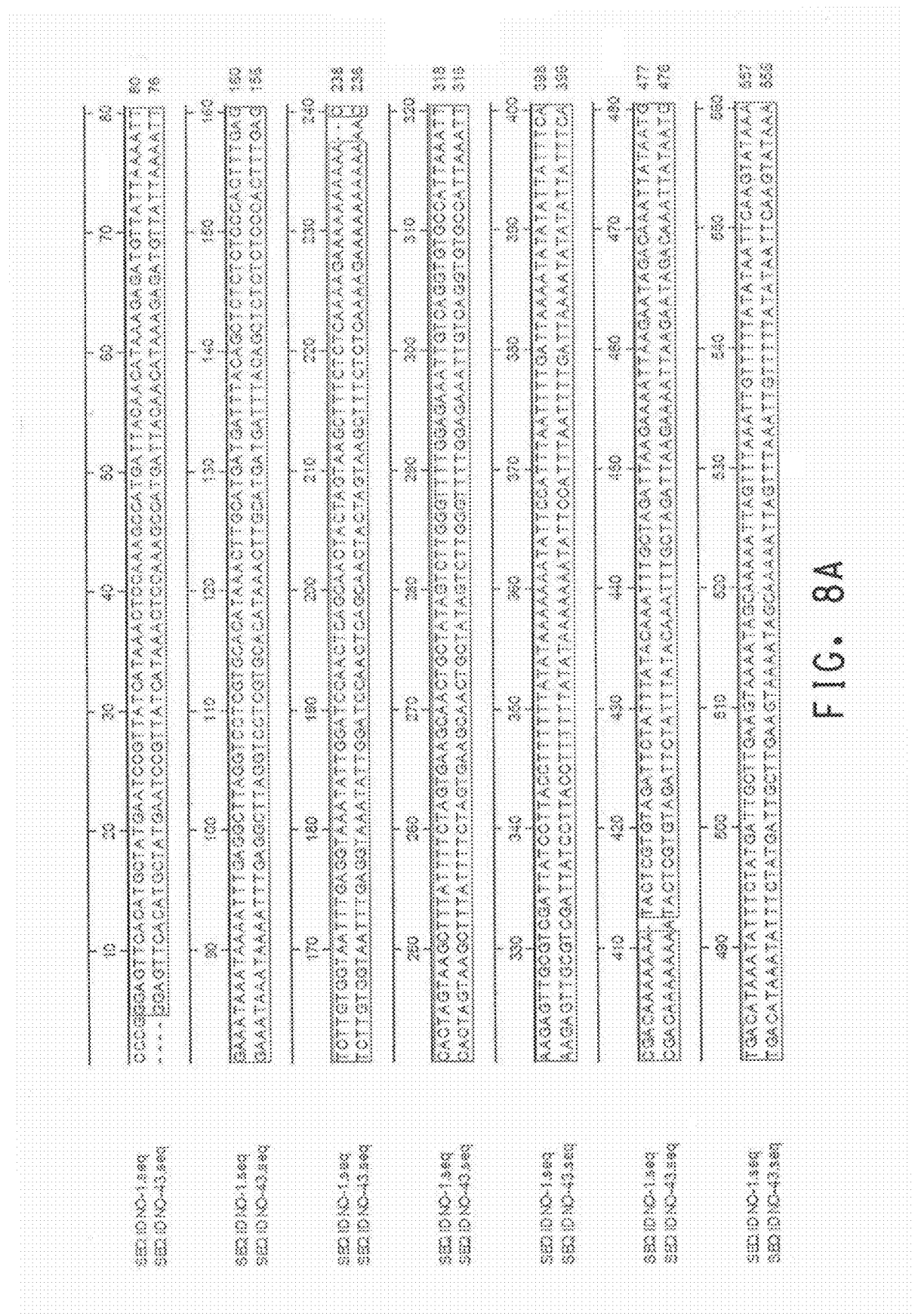
Figure 8B:
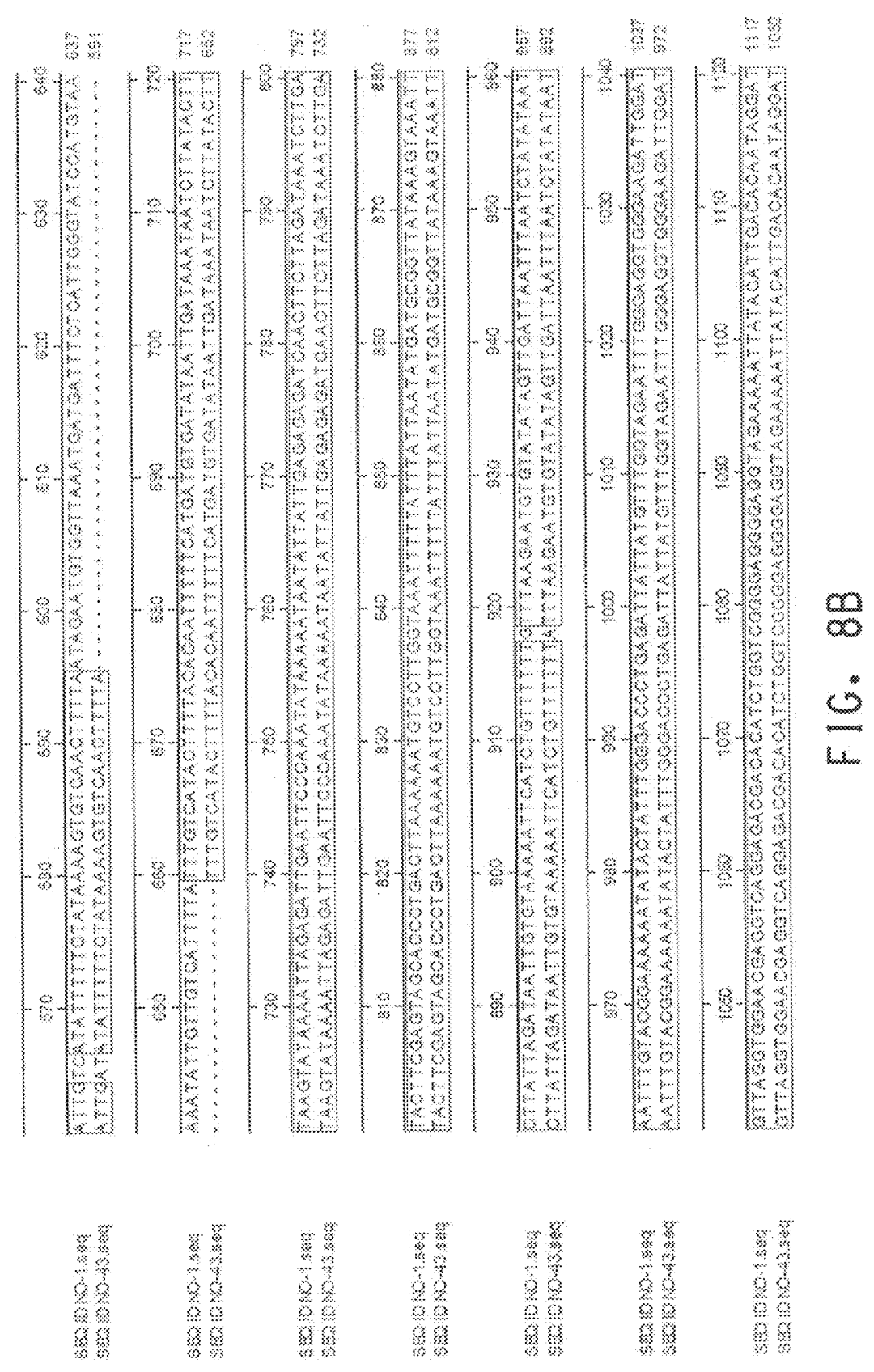
Figure 8C:
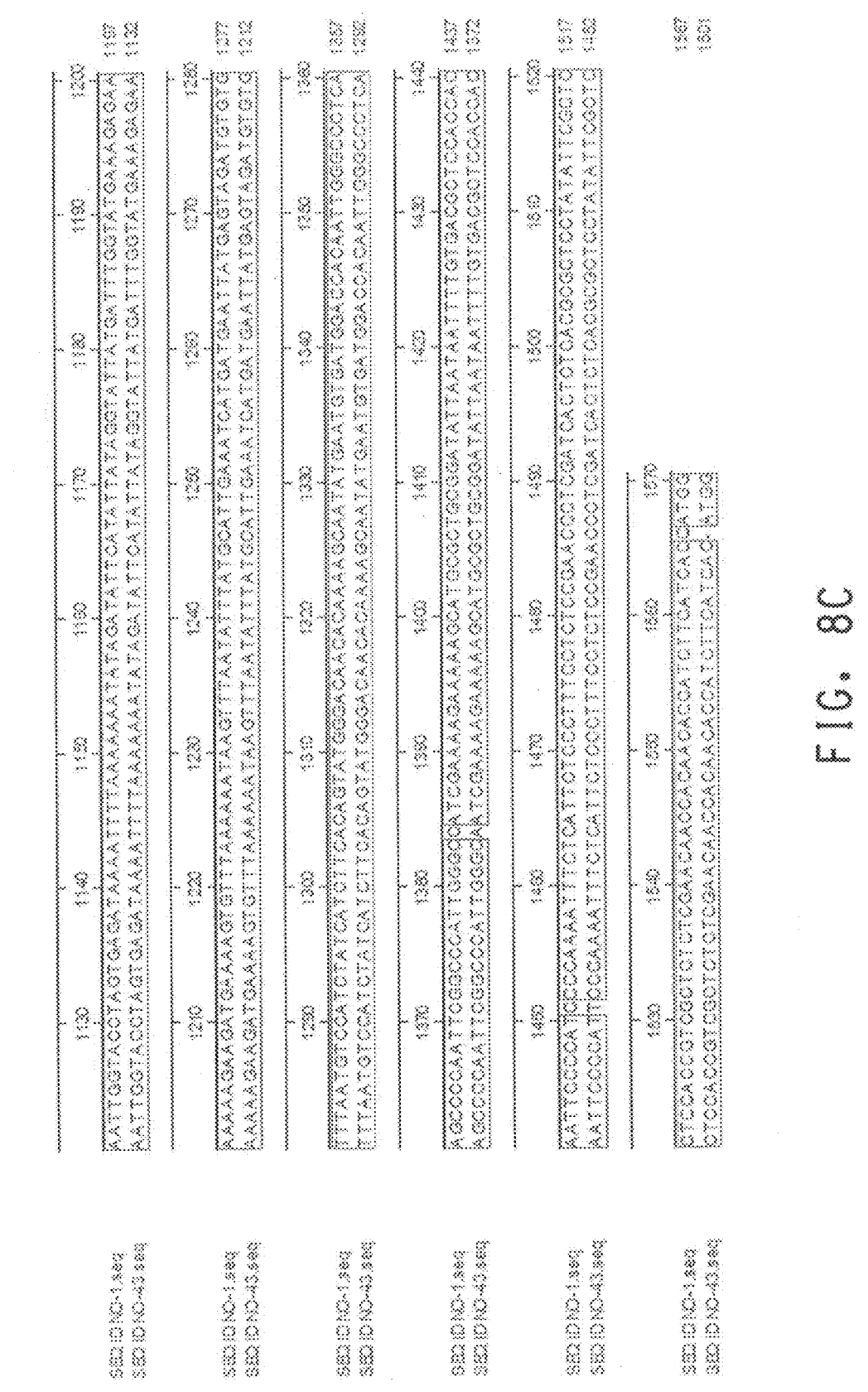
Figure 8D:
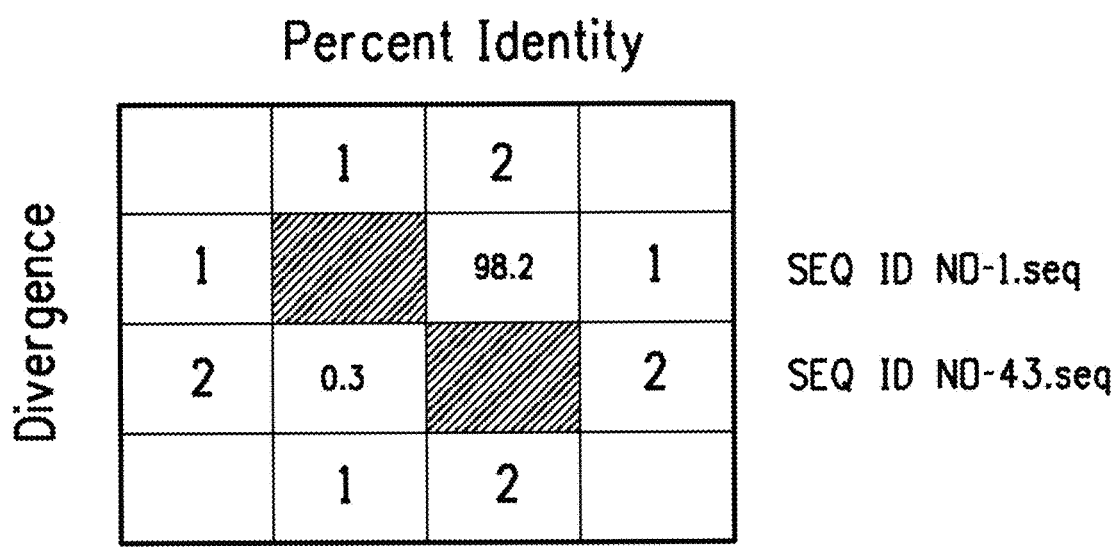

FIG. 8 A-C shows a nucleotide alignment of SEQ ID NO: 1, comprising the ADF1 promoter of the disclosure, and SEQ ID NO: 43, comprising a 1501 bp native soybean genomic DNA from Gm15:9788827 . . . 9790327 (Schmutz J. et al., Genome sequence of the palaeopolyploid soybean, Nature 463:178-183, 2010). FIG. 8-D shows the percent sequence identity between the ADF1 promoter of SEQ ID NO:1 and the corresponding native soybean genomic DNA of SEQ ID NO:43, based on the Clustal V method of alignment with pairwise alignment default parameters (KTUPLE=2, GAP PENALTY=5, WINDOW=4 and DIAGONALS SAVED=4).

The sequence descriptions summarize the Sequence Listing attached hereto. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219 (2):345-373 (1984).

SEQ ID NO:1 is a 1567 bp (base pair) DNA sequence comprising the full length soybean ADF1 promoter flanked by Xma1 (cccggg) and NcoI (ccatgg) restriction sites.

SEQ ID NO:2 is a 1559 bp form of the ADF1 promoter shown in SEQ ID NO:1 (bp 4-1562 of SEQ ID NO:1) with the 5' XmaI and 3' end NcoI sites removed.

SEQ ID NO:3 is a 1243 bp truncated form of the ADF1 promoter shown in SEQ ID NO:1 (bp 320-1562 of SEQ ID NO:1)

SEQ ID NO:4 is a 985 bp truncated form of the ADF1 promoter shown in SEQ ID NO:1 (bp 578-1562 of SEQ ID NO:1).

SEQ ID NO:5 is a 770 bp truncated form of the ADF1 promoter shown in SEQ ID NO:1 (bp 793-1562 of SEQ ID NO:1).

SEQ ID NO:6 is a 458 4 bp truncated form of the ADF1 promoter shown in SEQ ID NO:1 (bp 1105-1562 of SEQ ID NO:1).

SEQ ID NO:7 is a 212 bp truncated form of the ADF1 promoter shown in SEQ ID NO:1 (bp 1351-1562 of SEQ ID NO:1).

SEQ ID NO:8 is an oligonucleotide primer used as a gene-specific sense primer in the PCR amplification of the full length ADF1 promoter in SEQ ID NO:1 when paired with SEQ ID NO:9. A restriction enzyme XmaI recognition site CCCGGG is included for subsequent cloning.

SEQ ID NO:9 is an oligonucleotide primer used as a gene-specific antisense primer in the PCR amplification of the full length ADF1 promoter in SEQ ID NO:1 when paired with SEQ ID NO:8. A restriction enzyme NcoI recognition site CCATGG is included for subsequent cloning.

SEQ ID NO:10 is an oligonucleotide primer used as an antisense primer in the PCR amplifications of the truncated ADF1 promoters in SEQ ID NOs:2, 3, 4, 5, 6, or 7 when paired with SEQ ID NOs: 11, 12, 13, 14, 15, or 16, respectively.

SEQ ID NO:11 is an oligonucleotide primer used as a sense primer in the PCR amplification of the full length ADF1 promoter in SEQ ID NO:2 when paired with SEQ ID NO:10.

SEQ ID NO:12 is an oligonucleotide primer used as a sense primer in the PCR amplification of the truncated ADF1 promoter in SEQ ID NO:3 when paired with SEQ ID NO:10.

SEQ ID NO:13 is an oligonucleotide primer used as a sense primer in the PCR amplification of the truncated ADF1 promoter in SEQ ID NO:4 when paired with SEQ ID NO:10.

SEQ ID NO:14 is an oligonucleotide primer used as a sense primer in the PCR amplification of the truncated ADF1 promoter in SEQ ID NO:5 when paired with SEQ ID NO:10.

SEQ ID NO:15 is an oligonucleotide primer used as a sense primer in the PCR amplification of the truncated ADF1 promoter in SEQ ID NO:6 when paired with SEQ ID NO:10.

SEQ ID NO:16 is an oligonucleotide primer used as a sense primer in the PCR amplification of the truncated ADF1 promoter in SEQ ID NO:7 when paired with SEQ ID NO:10.

SEQ ID NO:17 is the 1084 bp nucleotide sequence of the putative soybean actin depolymerizing factor ADF1 cDNA (PSO315053). Nucleotides 1 to 132 are the 5' untranslated sequence, nucleotides 133 to 135 are the translation initiation codon, nucleotides 133 to 552 are the polypeptide coding region, nucleotides 550 to 552 are the termination codon, and nucleotides 553 to 1084 are part of the 3' untranslated sequence.

SEQ ID NO:18 is the predicted 139 aa (amino acid) long peptide sequence translated from the coding region of the putative soybean actin depolymerizing factor ADF1 nucleotide sequence SEQ ID NO:17.

SEQ ID NO:19 is the 4844 bp sequence of plasmid QC532.

SEQ ID NO:20 is the 4910 bp sequence of plasmid QC635.

SEQ ID NO:21 is the 8482 bp sequence of plasmid QC478i.

SEQ ID NO:22 is the 9509 bp sequence of plasmid QC644.

SEQ ID NO:23 is the 4376 bp sequence of plasmid QC532-1.

SEQ ID NO:24 is the 5286 bp sequence of plasmid QC330.

SEQ ID NO:25 is the 5217 bp sequence of plasmid QC532-1Y.

SEQ ID NO:26 is a sense primer used in quantitative PCR analysis of SAMS:HRA transgene copy numbers.

SEQ ID NO:27 is a FAM labeled fluorescent DNA oligo probe used in quantitative PCR analysis of SAMS:HRA transgene copy numbers.

SEQ ID NO:28 is an antisense primer used in quantitative PCR analysis of SAMS:HRA transgene copy numbers.

SEQ ID NO:29 is a sense primer used in quantitative PCR analysis of GM-ADF1:GFP transgene copy numbers.

SEQ ID NO:30 is a FAM labeled fluorescent DNA oligo probe used in quantitative PCR analysis of GM-ADF1:GFP transgene copy numbers.

SEQ ID NO:31 is an antisense primer used in quantitative PCR analysis of GM-ADF1:GFP transgene copy numbers.

SEQ ID NO:32 is a sense primer used as an endogenous control gene primer in quantitative PCR analysis of transgene copy numbers.

SEQ ID NO:33 is a VIC labeled DNA oligo probe used as an endogenous control gene probe in quantitative PCR analysis of transgene copy numbers.

SEQ ID NO:34 is an antisense primer used as an endogenous control gene primer in quantitative PCR analysis of transgene copy numbers.

SEQ ID NO:35 is the recombination site attL1 sequence in the GATEWAY® cloning system (Invitrogen, Carlsbad, Calif.).

SEQ ID NO:36 is the recombination site attL2 sequence in the GATEWAY® cloning system (Invitrogen).

SEQ ID NO:37 is the recombination site attR1 sequence in the GATEWAY® cloning system (Invitrogen).

SEQ ID NO:38 is the recombination site attR2 sequence in the GATEWAY® cloning system (Invitrogen).

SEQ ID NO:39 is the recombination site attB1 sequence in the GATEWAY® cloning system (Invitrogen).

SEQ ID NO:40 is the recombination site attB2 sequence in the GATEWAY® cloning system (Invitrogen).

SEQ ID NO:41 is the 1025 bp nucleotide sequence of the *Glycine max* actin depolymerizing factor 2-like (LOCI 00813011) mRNA (NCBI Accession XM_003534986) similar to the ADF1 gene (PSO315053) sequence SEQ ID NO:17.

SEQ ID NO:42 is a partial soybean uncharacterized LOCI 00305514 (LOC100305514) nucleotide sequence (NCBI accession NM_001249519). SEQ ID NO: 43 is a 1501 bp fragment of native soybean genomic DNA Gm15: 9788827 . . . 9790327 from cultivar "Williams82" (Schmutz J. et al. Nature 463: 178-183, 2010).

SEQ ID NO:44 is a 128 bp fragment of the 5' untranslated region of the ADF1 promoter.

DETAILED DESCRIPTION OF THE INVENTION

The disclosure of all patents, patent applications, and publications cited herein are incorporated by reference in their entirety.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth.

In the context of this disclosure, a number of terms shall be utilized.

An "isolated polynucleotide" refers to a polymer of ribonucleotides (RNA) or deoxyribonucleotides (DNA) that is single- or double-stranded, optionally containing synthetic, non-natural or altered nucleotide bases. An isolated polynucleotide in the form of DNA may be comprised of one or more segments of cDNA, genomic DNA or synthetic DNA.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

A "soybean ADF1 promoter", "GM-ADF1 promoter" or "ADF1 promoter" are used interchangeably herein, and refer to the promoter of a putative *Glycine max* gene with significant homology to actin depolymerizing factor (ADF) genes identified in various plant species including soybean that are deposited in National Center for Biotechnology Information (NCBI) database. The term "soybean ADF1 promoter" encompasses both a native soybean promoter and an engineered sequence comprising a fragment of the native soybean promoter with a DNA linker attached to facilitate cloning. A DNA linker may comprise a restriction enzyme site.

"Promoter" refers to a nucleic acid fragment capable of controlling transcription of another nucleic acid fragment. A promoter is capable of controlling the expression of a coding sequence or functional RNA. Functional RNA includes, but is not limited to, transfer RNA (tRNA) and ribosomal RNA (rRNA). The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. New promoters of various types useful in plant cells are constantly being discovered; numerous examples may be found in the compilation by Okamuro and Goldberg (Biochemistry of Plants 15:1-82 (1989)). It is further recognized that since in most cases the exact boundaries of regulatory sequences have not been completely defined, DNA fragments of some variation may have identical promoter activity.

"Promoter functional in a plant" is a promoter capable of controlling transcription in plant cells whether or not its origin is from a plant cell.

"Tissue-specific promoter" and "tissue-preferred promoter" are used interchangeably to refer to a promoter that is expressed predominantly but not necessarily exclusively in one tissue or organ, but that may also be expressed in one specific cell.

"Developmentally regulated promoter" refers to a promoter whose activity is determined by developmental events.

"Constitutive promoter" refers to promoters active in all or most tissues or cell types of a plant at all or most developing stages. As with other promoters classified as "constitutive" (e.g. ubiquitin), some variation in absolute levels of expression can exist among different tissues or stages. The term "constitutive promoter" or "tissue-independent" are used interchangeably herein.

The promoter nucleotide sequences and methods disclosed herein are useful in regulating constitutive expression of any heterologous nucleotide sequences in a host plant in order to alter the phenotype of a plant.

A "heterologous nucleotide sequence" refers to a sequence that is not naturally occurring with the plant promoter sequence of the invention. While this nucleotide sequence is heterologous to the promoter sequence, it may be homologous, or native, or heterologous, or foreign, to the plant host. However, it is recognized that the instant promoters may be used with their native coding sequences to increase or decrease expression resulting in a change in phenotype in the transformed seed. The terms "heterologous nucleotide sequence", "heterologous sequence", "heterologous nucleic acid fragment", and "heterologous nucleic acid sequence" are used interchangeably herein.

Among the most commonly used promoters are the nopaline synthase (NOS) promoter (Ebert et al., Proc. Natl. Acad. Sci. U.S.A. 84:5745-5749 (1987)), the octapine synthase (OCS) promoter, caulimovirus promoters such as the cauliflower mosaic virus (CaMV) 19S promoter (Lawton et al., Plant Mol. Biol. 9:315-324 (1987)), the CaMV 35S promoter (Odell et al., Nature 313:810-812 (1985)), and the figwort mosaic virus 35S promoter (Sanger et al., Plant Mol. Biol. 14:433-43 (1990)), the light inducible promoter from the small subunit of rubisco, the Adh promoter (Walker et al., Proc. Natl. Acad. Sci. U.S.A. 84:6624-66280 (1987), the sucrose synthase promoter (Yang et al., Proc. Natl. Acad. Sci. U.S.A. 87:4144-4148 (1990)), the R gene complex promoter (Chandler et al., Plant Cell 1:1175-1183 (1989)), the chlorophyll a/b binding protein gene promoter, etc. Other commonly used promoters are, the promoters for the potato tuber ADPGPP genes, the sucrose synthase promoter, the granule bound starch synthase promoter, the glutelin gene promoter, the maize waxy promoter, Brittle gene promoter, and Shrunken 2 promoter, the acid chitinase gene promoter, and the zein gene promoters (15 kD, 16 kD, 19 kD, 22 kD, and 27 kD; Perdersen et al., Cell 29:1015-1026 (1982)). A plethora of promoters is described in PCT Publication No. WO 00/18963 published on Apr. 6, 2000, the disclosure of which is hereby incorporated by reference.

The present invention encompasses functional fragments of the promoter sequences disclosed herein.

A "functional fragment" refer to a portion or subsequence of the promoter sequence of the present invention in which the ability to initiate transcription or drive gene expression (such as to produce a certain phenotype) is retained. Fragments can be obtained via methods such as site-directed mutagenesis and synthetic construction. As with the provided promoter sequences described herein, the functional fragments operate to promote the expression of an operably linked heterologous nucleotide sequence, forming a recombinant DNA construct (also, a chimeric gene). For example, the fragment can be used in the design of recombinant DNA constructs to produce the desired phenotype in a transformed plant. Recombinant DNA constructs can be designed for use in co-suppression or antisense by linking a promoter fragment in the appropriate orientation relative to a heterologous nucleotide sequence.

A nucleic acid fragment that is functionally equivalent to the promoter of the present invention is any nucleic acid fragment that is capable of controlling the expression of a coding sequence or functional RNA in a similar manner to the promoter of the present invention.

In an embodiment of the present invention, the promoters disclosed herein can be modified. Those skilled in the art can create promoters that have variations in the polynucleotide sequence. The polynucleotide sequence of the promoters of the present invention as shown in SEQ ID NOS: 1, 2, 3, 4, 5, 6, 7, and 43, may be modified or altered to enhance their control characteristics. As one of ordinary skill in the art will appreciate, modification or alteration of the promoter sequence can also be made without substantially affecting the promoter function. The methods are well known to those of skill in the art. Sequences can be modified, for example by insertion, deletion, or replacement of template sequences in a PCR-based DNA modification approach.

A "variant promoter", as used herein, is the sequence of the promoter or the sequence of a functional fragment of a promoter containing changes in which one or more nucleotides of the original sequence is deleted, added, and/or substituted, while substantially maintaining promoter function. One or more base pairs can be inserted, deleted, or substituted internally to a promoter. In the case of a promoter fragment, variant promoters can include changes affecting the transcription of a minimal promoter to which it is operably linked. Variant promoters can be produced, for example, by standard DNA mutagenesis techniques or by chemically synthesizing the variant promoter or a portion thereof.

Methods for construction of chimeric and variant promoters of the present invention include, but are not limited to, combining control elements of different promoters or duplicating portions or regions of a promoter (see for example, U.S. Pat. No. 4,990,607; U.S. Pat. No. 5,110,732; and U.S. Pat. No. 5,097,025). Those of skill in the art are familiar with the standard resource materials that describe specific conditions and procedures for the construction, manipulation, and isolation of macromolecules (e.g., polynucleotide molecules and plasmids), as well as the generation of recombinant organisms and the screening and isolation of polynucleotide molecules.

In some aspects of the present invention, the promoter fragments can comprise at least about 20 contiguous nucleotides, or at least about 50 contiguous nucleotides, or at least about 75 contiguous nucleotides, or at least about 100 contiguous nucleotides, or at least about 150 contiguous nucleotides, or at least about 200 contiguous nucleotides of SEQ ID NO:1, SEQ ID NO:2, SEQ ID NO:3, SEQ ID NO:4, SEQ ID NO:5, SEQ ID NO:6, SEQ ID NO:7 or SEQ ID NO:43. In another aspect of the present invention, the promoter fragments can comprise at least about 250 contiguous nucleotides, or at least about 300 contiguous nucleotides, or at least about 350 contiguous nucleotides, or at least about 400 contiguous nucleotides, or at least about 450 contiguous nucleotides, or at least about 500 contiguous nucleotides, or at least about 550 contiguous nucleotides, or at least about 600 contiguous nucleotides, or at least about 650 contiguous nucleotides, or at least about 700 contiguous nucleotides, or at least about 750 contiguous nucleotides, or at least about 800 contiguous nucleotides, or at least about 850 contiguous nucleotides, or at least about 900 contiguous nucleotides, or at least about 950 contiguous nucleotides, or at least about 1000 contiguous nucleotides, or at least about 1050 contiguous nucleotides, or at least about 1100 contiguous nucleotides, or at least about 1150 contiguous nucleotides, or at least about 1200 contiguous nucleotides, or at least about 1250 contiguous nucleotides, or at least about 1300 contiguous nucleotides, or at least about 1350 contiguous nucleotides of SEQ ID NO:1. In another aspect, a promoter fragment is the nucleotide sequence set forth in SEQ ID NO:2, SEQ ID NO:3, SEQ ID NO:4, SEQ ID NO:5, SEQ ID NO:6, SEQ ID NO:7 or SEQ ID NO:43. The nucleotides of such fragments will usually comprise the TATA recognition sequence of the particular promoter sequence. Such fragments may be obtained by use of restriction enzymes to cleave the naturally occurring promoter nucleotide sequences disclosed herein, by synthesizing a nucleotide sequence from the naturally occurring promoter DNA sequence, or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989.

The terms "full complement" and "full-length complement" are used interchangeably herein, and refer to a complement of a given nucleotide sequence, wherein the complement and the nucleotide sequence consist of the same number of nucleotides and are 100% complementary.

The terms "substantially similar" and "corresponding substantially" as used herein refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences.

The isolated promoter sequence of the present invention can be modified to provide a range of constitutive expression levels of the heterologous nucleotide sequence. Thus, less than the entire promoter regions may be utilized and the ability to drive expression of the coding sequence retained. However, it is recognized that expression levels of the mRNA may be decreased with deletions of portions of the promoter sequences. Likewise, the tissue-independent, constitutive nature of expression may be changed.

Modifications of the isolated promoter sequences of the present invention can provide for a range of constitutive expression of the heterologous nucleotide sequence. Thus, they may be modified to be weak constitutive promoters or strong constitutive promoters. Generally, by "weak promoter" is intended a promoter that drives expression of a coding sequence at a low level. By "low level" is intended at levels about $1/10,000$ transcripts to about $1/100,000$ transcripts to about $1/500,000$ transcripts. Conversely, a strong promoter drives expression of a coding sequence at high level, or at about $1/10$ transcripts to about $1/100$ transcripts to about $1/1,000$ transcripts.

Moreover, the skilled artisan recognizes that substantially similar nucleic acid sequences encompassed by this invention are also defined by their ability to hybridize, under moderately stringent conditions (for example, 0.5×SSC, 0.1% SDS, 60° C.) with the sequences exemplified herein, or to any portion of the nucleotide sequences reported herein and which are functionally equivalent to the promoter of the invention. Estimates of such homology are provided by either DNA-DNA or DNA-RNA hybridization under conditions of stringency as is well understood by those skilled in the art (Hames and Higgins, Eds.; In Nucleic Acid Hybridisation; IRL Press: Oxford, U.K., 1985). Stringency conditions can be adjusted to screen for moderately similar fragments, such as homologous sequences from distantly related organisms, to highly similar fragments, such as genes that duplicate functional enzymes from closely related organisms. Post-hybridization washes partially determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. Another set of stringent conditions uses higher temperatures in which the washes are identical to those above except for the temperature of the final two 30 min washes in 0.2×SSC, 0.5% SDS was increased to 60° C. Another set of highly stringent conditions uses two final washes in 0.1×SSC, 0.1% SDS at 65° C.

Preferred substantially similar nucleic acid sequences encompassed by this invention are those sequences that are 80% identical to the nucleic acid fragments reported herein or which are 80% identical to any portion of the nucleotide sequences reported herein. More preferred are nucleic acid fragments which are 90% identical to the nucleic acid sequences reported herein, or which are 90% identical to any portion of the nucleotide sequences reported herein. Most preferred are nucleic acid fragments which are 95% identical to the nucleic acid sequences reported herein, or which are 95% identical to any portion of the nucleotide sequences reported herein. It is well understood by one skilled in the art that many levels of sequence identity are useful in identifying related polynucleotide sequences. Useful examples of percent identities are those listed above, or also preferred is any integer percentage from 72% to 100%, such as 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%.

In one embodiment, this invention concerns an isolated polynucleotide comprising a promoter wherein said promoter comprises a nucleotide sequence having at least 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100% sequence identity, based on the Clustal V method of alignment with pairwise alignment default parameters (KTUPLE=2, GAP PENALTY=5, WINDOW=4 and DIAGONALS SAVED=4) when compared to the nucleotide sequence of SEQ ID NO:1. As described in Example 2, comparison of SEQ ID NO:1 to a soybean cDNA library revealed that SEQ ID NOs: 1, 2, 3, 4, 5, 6, 7, and 49 comprise a 5' untranslated region (5'UTR) of at least 128 base pairs (SEQ ID NO:43). It is known to one of skilled in the art that a 5' UTR region can be altered (deletion or substitutions of bases) or replaced by an alternative 5'UTR while maintaining promoter activity.

This 5'UTR region represents (128/1567)*100=8.2% of SEQ ID NO:1, (128/1559)*100=8.2% of SEQ ID NO:2, (128/1243)*100=10.3% of SEQ ID NO:3, (128/985) *100=13.0% of SEQ ID NO:4, (128/770)*100=16.6% of SEQ ID NO:5, (128/458)*100=27.9% of SEQ ID NO:6 and (128/212)*100=60.0% of SEQ ID NO:7 respectively, indicating that an isolated polynucleotide of 91.8% sequence identity to SEQ ID NO:1, or 91.8% sequence identity to SEQ ID NO:2, or 89.7% sequence identity to SEQ ID NO:3, or 87.0% sequence identity to SEQ ID NO:4, or 83.4% sequence identity to SEQ ID NO:5, or 72.1% sequence identity to SEQ ID NO:6, or 40% sequence identity to SEQ ID NO:7 can be generated while maintaining promoter activity.

A "substantially homologous sequence" refers to variants of the disclosed sequences such as those that result from site-directed mutagenesis, as well as synthetically derived sequences. A substantially homologous sequence of the present invention also refers to those fragments of a particular promoter nucleotide sequence disclosed herein that operate to promote the constitutive expression of an operably linked heterologous nucleic acid fragment. These promoter fragments will comprise at least about 20 contiguous nucleotides, preferably at least about 50 contiguous nucleotides, more preferably at least about 75 contiguous nucleotides, even more preferably at least about 100 contiguous nucleotides of the particular promoter nucleotide sequence disclosed herein. The nucleotides of such fragments will usually comprise the TATA recognition sequence of the particular promoter sequence. Such fragments may be obtained by use of restriction enzymes to cleave the naturally occurring promoter nucleotide sequences disclosed herein; by synthesizing a nucleotide sequence from the naturally occurring promoter DNA sequence; or may be obtained through the use of PCR technology. See particularly, Mullis et al., Methods Enzymol. 155:335-350 (1987), and Higuchi, R. In PCR Technology: Principles and Applications for DNA Amplifications; Erlich, H. A., Ed.; Stockton Press Inc.: New York, 1989. Again, variants of these promoter fragments, such as those resulting from site-directed mutagenesis, are encompassed by the compositions of the present invention.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

Sequence alignments and percent identity calculations may be determined using a variety of comparison methods designed to detect homologous sequences including, but not limited to, the Megalign® program of the LASERGENE® bioinformatics computing suite (DNASTAR® Inc., Madison, Wis.). Unless stated otherwise, multiple alignment of the sequences provided herein were performed using the Clustal V method of alignment (Higgins and Sharp (1989) *CABIOS*. 5:151-153) with the default parameters (GAP PENALTY=10, GAP LENGTH PENALTY=10). Default parameters for pairwise alignments and calculation of percent identity of protein sequences using the Clustal V method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences, using the Clustal V program, it is possible to obtain "percent identity" and "divergence" values by viewing the "sequence distances" table on the same program; unless stated otherwise, percent identities and divergences provided and claimed herein were calculated in this manner.

Alternatively, the Clustal W method of alignment may be used. The Clustal W method of alignment (described by Higgins and Sharp, *CABIOS*. 5:151-153 (1989); Higgins, D. G. et al., *Comput. Appl. Biosci.* 8:189-191 (1992)) can be found in the MegAlign™ v6.1 program of the LASER-GENE® bioinformatics computing suite (DNASTAR® Inc., Madison, Wis.). Default parameters for multiple alignment correspond to GAP PENALTY=10, GAP LENGTH PENALTY=0.2, Delay Divergent Sequences=30%, DNA Transition Weight=0.5, Protein Weight Matrix=Gonnet Series, DNA Weight Matrix=IUB. For pairwise alignments the default parameters are Alignment=Slow-Accurate, Gap Penalty=10.0, Gap Length=0.10, Protein Weight Matrix=Gonnet 250 and DNA Weight Matrix=IUB. After alignment of the sequences using the Clustal W program, it is possible to obtain "percent identity" and "divergence" values by viewing the "sequence distances" table in the same program.

In one embodiment the % sequence identity is determined over the entire length of the molecule (nucleotide or amino acid).

A "substantial portion" of an amino acid or nucleotide sequence comprises enough of the amino acid sequence of a polypeptide or the nucleotide sequence of a gene to afford putative identification of that polypeptide or gene, either by manual evaluation of the sequence by one skilled in the art, or by computer-automated sequence comparison and identification using algorithms such as BLAST (Altschul, S. F. et al., *J. Mol. Biol.* 215:403-410 (1993)) and Gapped Blast (Altschul, S. F. et al., *Nucleic Acids Res.* 25:3389-3402 (1997)). BLASTN refers to a BLAST program that compares a nucleotide query sequence against a nucleotide sequence database.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" or "recombinant expression construct", which are used interchangeably, refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

An "intron" is an intervening sequence in a gene that is transcribed into RNA but is then excised in the process of generating the mature mRNA. The term is also used for the excised RNA sequences. An "exon" is a portion of the sequence of a gene that is transcribed and is found in the mature messenger RNA derived from the gene, but is not necessarily a part of the sequence that encodes the final gene product.

The "translation leader sequence" refers to a polynucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D., *Molecular Biotechnology* 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., *Plant Cell* 1:671-680 (1989).

"RNA transcript" refers to a product resulting from RNA polymerase-catalyzed transcription of a DNA sequence. When an RNA transcript is a perfect complementary copy of a DNA sequence, it is referred to as a primary transcript or it may be a RNA sequence derived from posttranscriptional processing of a primary transcript and is referred to as a mature RNA. "Messenger RNA" ("mRNA") refers to RNA that is without introns and that can be translated into protein by the cell. "cDNA" refers to a DNA that is complementary to and synthesized from an mRNA template using the enzyme reverse transcriptase. The cDNA can be single-stranded or converted into the double-stranded by using the Klenow fragment of DNA polymerase I. "Sense" RNA refers to RNA transcript that includes mRNA and so can be translated into protein within a cell or in vitro. "Antisense RNA" refers to a RNA transcript that is complementary to all or part of a target primary transcript or mRNA and that blocks expression or transcripts accumulation of a target gene (U.S. Pat. No. 5,107,065). The complementarity of an antisense RNA may be with any part of the specific gene transcript, i.e. at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The terms "initiate transcription", "initiate expression", "drive transcription", and "drive expression" are used interchangeably herein and all refer to the primary function of a promoter. As detailed throughout this disclosure, a promoter is a non-coding genomic DNA sequence, usually upstream (5') to the relevant coding sequence, and its primary function is to act as a binding site for RNA polymerase and initiate transcription by the RNA polymerase. Additionally, there is "expression" of RNA, including functional RNA, or the expression of polypeptide for operably linked encoding nucleotide sequences, as the transcribed RNA ultimately is translated into the corresponding polypeptide.

The term "expression", as used herein, refers to the production of a functional end-product e.g., an mRNA or a protein (precursor or mature).

The term "expression cassette" as used herein, refers to a discrete nucleic acid fragment into which a nucleic acid sequence or fragment can be moved.

Expression or overexpression of a gene involves transcription of the gene and translation of the mRNA into a precursor or mature protein. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression or transcript accumulation of identical or substantially similar foreign or endogenous genes (U.S. Pat. No. 5,231,020). The mechanism of co-suppression may be at the DNA level (such as DNA methylation), at the transcriptional level, or at posttranscriptional level.

Co-suppression constructs in plants previously have been designed by focusing on overexpression of a nucleic acid sequence having homology to an endogenous mRNA, in the sense orientation, which results in the reduction of all RNA having homology to the overexpressed sequence (see Vaucheret et al., Plant J. 16:651-659 (1998); and Gura, Nature 404:804-808 (2000)). The overall efficiency of this phenomenon is low, and the extent of the RNA reduction is widely variable. Recent work has described the use of "hairpin" structures that incorporate all, or part, of an mRNA encoding sequence in a complementary orientation that results in a potential "stem-loop" structure for the expressed RNA (PCT Publication No. WO 99/53050 published on Oct. 21, 1999; and PCT Publication No. WO 02/00904 published on Jan. 3, 2002). This increases the frequency of co-suppression in the recovered transgenic plants. Another variation describes the use of plant viral sequences to direct the suppression, or "silencing", of proximal mRNA encoding sequences (PCT Publication No. WO 98/36083 published on Aug. 20, 1998). Genetic and molecular evidences have been obtained suggesting that dsRNA mediated mRNA cleavage may have been the conserved mechanism underlying these gene silencing phenomena (Elmayan et al., Plant Cell 10:1747-1757 (1998); Galun, In Vitro Cell. Dev. Biol. Plant 41(2):113-123 (2005); Pickford et al, Cell. Mol. Life Sci. 60(5):871-882 (2003)).

As stated herein, "suppression" refers to a reduction of the level of enzyme activity or protein functionality (e.g., a phenotype associated with a protein) detectable in a transgenic plant when compared to the level of enzyme activity or protein functionality detectable in a non-transgenic or wild type plant with the native enzyme or protein. The level of enzyme activity in a plant with the native enzyme is referred to herein as "wild type" activity. The level of protein functionality in a plant with the native protein is referred to herein as "wild type" functionality. The term "suppression" includes lower, reduce, decline, decrease, inhibit, eliminate and prevent. This reduction may be due to a decrease in translation of the native mRNA into an active enzyme or functional protein. It may also be due to the transcription of the native DNA into decreased amounts of mRNA and/or to rapid degradation of the native mRNA. The term "native enzyme" refers to an enzyme that is produced naturally in a non-transgenic or wild type cell. The terms "non-transgenic" and "wild type" are used interchangeably herein.

"Altering expression" refers to the production of gene product(s) in transgenic organisms in amounts or proportions that differ significantly from the amount of the gene product(s) produced by the corresponding wild-type organisms (i.e., expression is increased or decreased).

"Transformation" as used herein refers to both stable transformation and transient transformation.

"Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms.

"Transient transformation" refers to the introduction of a nucleic acid fragment into the nucleus, or DNA-containing organelle, of a host organism resulting in gene expression without genetically stable inheritance.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

"Transgenic" refers to any cell, cell line, callus, tissue, plant part or plant, the genome of which has been altered by the presence of a heterologous nucleic acid, such as a recombinant DNA construct, including those initial transgenic events as well as those created by sexual crosses or asexual propagation from the initial transgenic event. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

"Genome" as it applies to plant cells encompasses not only chromosomal DNA found within the nucleus, but organelle DNA found within subcellular components (e.g., mitochondrial, plastid) of the cell.

"Plant" includes reference to whole plants, plant organs, plant tissues, seeds and plant cells and progeny of same. Plant cells include, without limitation, cells from seeds, suspension cultures, embryos, meristematic regions, callus tissue, leaves, roots, shoots, gametophytes, sporophytes, pollen, and microspores.

The terms "monocot" and "monocotyledonous plant" are used interchangeably herein. A monocot of the current invention includes the Gramineae.

The terms "dicot" and "dicotyledonous plant" are used interchangeably herein. A dicot of the current invention includes the following families: Brassicaceae, Leguminosae, and Solanaceae.

"Progeny" comprises any subsequent generation of a plant.

"Transgenic plant" includes reference to a plant which comprises within its genome a heterologous polynucleotide. For example, the heterologous polynucleotide is stably integrated within the genome such that the polynucleotide is passed on to successive generations. The heterologous polynucleotide may be integrated into the genome alone or as part of a recombinant DNA construct.

"Transient expression" refers to the temporary expression of often reporter genes such as β-glucuronidase (GUS), fluorescent protein genes ZS-GREEN1, ZS-YELLOW1 N1, AM-CYAN1, DS-RED in selected certain cell types of the host organism in which the transgenic gene is introduced temporally by a transformation method. The transformed materials of the host organism are subsequently discarded after the transient gene expression assay.

Standard recombinant DNA and molecular cloning techniques used herein are well known in the art and are described more fully in Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989") or Ausubel, F. M., Brent, R., Kingston, R. E., Moore, D. D., Seidman, J. G., Smith, J. A. and Struhl, K., Eds.; In Current Protocols in Molecular Biology; John Wiley and Sons: New York, 1990 (hereinafter "Ausubel et al., 1990").

"PCR" or "Polymerase Chain Reaction" is a technique for the synthesis of large quantities of specific DNA segments, consisting of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps comprises a cycle.

The terms "plasmid", "vector" and "cassette" refer to an extra chromosomal element often carrying genes that are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "recombinant DNA construct" or "recombinant expression construct" is used interchangeably and refers to a discrete polynucleotide into which a nucleic acid sequence or fragment can be moved. Preferably, it is a plasmid vector or a fragment thereof comprising the promoters of the present invention. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., EMBO J. 4:2411-2418 (1985); De Almeida et al., Mol. Gen. Genetics 218:78-86 (1989)), and thus that multiple events must be screened in order to obtain lines displaying the desired expression level and pattern. Such screening may be accomplished by PCR and Southern analysis of DNA, RT-PCR and Northern analysis of mRNA expression, Western analysis of protein expression, or phenotypic analysis.

Various changes in phenotype are of interest including, but not limited to, modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in a change in phenotype of the transformed plant.

Genes of interest are reflective of the commercial markets and interests of those involved in the development of the crop. Crops and markets of interest change, and as developing nations open up world markets, new crops and technologies will emerge also. In addition, as our understanding of agronomic characteristics and traits such as yield and heterosis increase, the choice of genes for transformation will change accordingly. General categories of genes of interest include, but are not limited to, those genes involved in information, such as zinc fingers, those involved in communication, such as kinases, and those involved in housekeeping, such as heat shock proteins. More specific categories of transgenes, for example, include, but are not limited to, genes encoding important traits for agronomics, insect resistance, disease resistance, herbicide resistance, sterility, grain or seed characteristics, and commercial products. Genes of interest include, generally, those involved in oil, starch, carbohydrate, or nutrient metabolism as well as those affecting seed size, plant development, plant growth regulation, and yield improvement. Plant development and growth regulation also refer to the development and growth regulation of various parts of a plant, such as the flower, seed, root, leaf and shoot.

Other commercially desirable traits are genes and proteins conferring cold, heat, salt, and drought resistance.

Disease and/or insect resistance genes may encode resistance to pests that have great yield drag such as for example, anthracnose, soybean mosaic virus, soybean cyst nematode, root-knot nematode, brown leaf spot, Downy mildew, purple seed stain, seed decay and seedling diseases caused commonly by the fungi—*Pythium* sp., *Phytophthora* sp., *Rhizoctonia* sp., *Diaporthe* sp. Bacterial blight caused by the bacterium *Pseudomonas syringae* pv. Glycinea. Genes conferring insect resistance include, for example, *Bacillus thuringiensis* toxic protein genes (U.S. Pat. Nos. 5,366,892; 5,747,450; 5,737,514; 5,723,756; 5,593,881; and Geiser et al (1986) Gene 48:109); lectins (Van Damme et al. (1994) Plant Mol. Biol. 24:825); and the like.

Herbicide resistance traits may include genes coding for resistance to herbicides that act to inhibit the action of acetolactate synthase (ALS), in particular the sulfonylurea-type herbicides (e.g., the acetolactate synthase ALS gene containing mutations leading to such resistance, in particular the S4 and/or HRA mutations). The ALS-gene mutants encode resistance to the herbicide chlorsulfuron. Glyphosate acetyl transferase (GAT) is an N-acetyltransferase from *Bacillus licheniformis* that was optimized by gene shuffling for acetylation of the broad spectrum herbicide, glyphosate, forming the basis of a novel mechanism of glyphosate tolerance in transgenic plants (Castle et al. (2004) *Science* 304, 1151-1154).

Antibiotic resistance genes include, for example, neomycin phosphotransferase (npt) and hygromycin phosphotransferase (hpt). Two neomycin phosphotransferase genes are used in selection of transformed organisms: the neomycin phosphotransferase I (nptI) gene and the neomycin phosphotransferase II (npIII) gene. The second one is more widely used. It was initially isolated from the transposon Tn5 that was present in the bacterium strain *Escherichia coli* K12. The gene codes for the aminoglycoside 3'-phosphotransferase (denoted aph(3')-II or NPTII) enzyme, which inactivates by phosphorylation a range of aminoglycoside antibiotics such as kanamycin, neomycin, geneticin and paroromycin. NPTII is widely used as a selectable marker for plant transformation. It is also used in gene expression and regulation studies in different organisms in part because N-terminal fusions can be constructed that retain enzyme activity. NPTII protein activity can be detected by enzymatic assay. In other detection methods, the modified substrates, the phosphorylated antibiotics, are detected by thin-layer chromatography, dot-blot analysis or polyacrylamide gel electrophoresis. Plants such as maize, cotton, tobacco, *Arabidopsis*, flax, soybean and many others have been successfully transformed with the nptII gene.

The hygromycin phosphotransferase (denoted hpt, hph or aphIV) gene was originally derived from *Escherichia coli*. The gene codes for hygromycin phosphotransferase (HPT), which detoxifies the aminocyclitol antibiotic hygromycin B. A large number of plants have been transformed with the hpt gene and hygromycin B has proved very effective in the selection of a wide range of plants, including monocotyledonous. Most plants exhibit higher sensitivity to hygromycin B than to kanamycin, for instance cereals. Likewise, the hpt gene is used widely in selection of transformed mammalian cells. The sequence of the hpt gene has been modified for its use in plant transformation. Deletions and substitutions of amino acid residues close to the carboxy (C)-terminus of the enzyme have increased the level of resistance in certain plants, such as tobacco. At the same time, the hydrophilic C-terminus of the enzyme has been maintained and may be essential for the strong activity of HPT. HPT activity can be checked using an enzymatic assay. A non-destructive callus induction test can be used to verify hygromycin resistance.

Genes involved in plant growth and development have been identified in plants. One such gene, which is involved in cytokinin biosynthesis, is isopentenyl transferase (IPT). Cytokinin plays a critical role in plant growth and development by stimulating cell division and cell differentiation (Sun et al. (2003), Plant Physiol. 131: 167-176).

Calcium-dependent protein kinases (CDPK), a family of serine-threonine kinase found primarily in the plant kingdom, are likely to function as sensor molecules in calcium-mediated signaling pathways. Calcium ions are important second messengers during plant growth and development (Harper et al. Science 252, 951-954 (1993); Roberts et al. Curr. Opin. Cell Biol. 5, 242-246 (1993); Roberts et al. Annu. Rev. Plant Mol. Biol. 43, 375-414 (1992)).

Nematode responsive protein (NRP) is produced by soybean upon the infection of soybean cyst nematode. NRP has homology to a taste-modifying glycoprotein miraculin and the NF34 protein involved in tumor formation and hyper response induction. NRP is believed to function as a defense-inducer in response to nematode infection (Tenhaken et al. BMC Bioinformatics 6:169 (2005)).

The quality of seeds and grains is reflected in traits such as levels and types of fatty acids or oils, saturated and unsaturated, quality and quantity of essential amino acids, and levels of carbohydrates. Therefore, commercial traits can also be encoded on a gene or genes that could increase for example methionine and cysteine, two sulfur containing amino acids that are present in low amounts in soybeans. Cystathionine gamma synthase (CGS) and serine acetyl transferase (SAT) are proteins involved in the synthesis of methionine and cysteine, respectively.

Other commercial traits can encode genes to increase for example monounsaturated fatty acids, such as oleic acid, in oil seeds. Soybean oil for example contains high levels of polyunsaturated fatty acids and is more prone to oxidation than oils with higher levels of monounsaturated and saturated fatty acids. High oleic soybean seeds can be prepared by recombinant manipulation of the activity of oleoyl 12-desaturase (Fad2). High oleic soybean oil can be used in applications that require a high degree of oxidative stability, such as cooking for a long period of time at an elevated temperature.

Raffinose saccharides accumulate in significant quantities in the edible portion of many economically significant crop species, such as soybean (*Glycine max* L. Merrill), sugar beet (*Beta vulgaris*), cotton (*Gossypium hirsutum* L.), canola (*Brassica* sp.) and all of the major edible leguminous crops including beans (*Phaseolus* sp.), chick pea (*Cicer arietinum*), cowpea (*Vigna unguiculata*), mung bean (*Vigna radiata*), peas (*Pisum sativum*), lentil (*Lens culinaris*) and lupine (*Lupinus* sp.). Although abundant in many species, raffinose saccharides are an obstacle to the efficient utilization of some economically important crop species.

Down regulation of the expression of the enzymes involved in raffinose saccharide synthesis, such as galactinol synthase for example, would be a desirable trait.

In certain embodiments, the present invention contemplates the transformation of a recipient cell with more than one advantageous transgene. Two or more transgenes can be supplied in a single transformation event using either distinct transgene-encoding vectors, or a single vector incorporating two or more gene coding sequences. Any two or more transgenes of any description, such as those conferring herbicide, insect, disease (viral, bacterial, fungal, and nematode), or drought resistance, oil quantity and quality, or those increasing yield or nutritional quality may be employed as desired.

Actin-depolymerizing factors (ADF) and cofilins are a family of small actin-binding proteins found in all eukaryotic cells. Members of this family remodel the actin cytoskeleton, for example during cytokinesis. Cytoskeleton remodeling is a dynamic process whereby F-actin turnover occurs via polymerization, depolymerization, severing, nucleation, as well as large scale translocation events. ADF and cofilin-1 promote cytoskeletal dynamics by depolymerizing actin filaments by severing actin filaments and also increasing the rate at which monomers leave the filament's pointed end. Cofilin-1 and ADF seem to play overlapping roles in cells since the knockdown phenotype of either protein could be rescued by the overexpression of the other (Maciver and Hussey, Genome Biology 3:3007.1-3007.12 (2002); Hotulainen et al., Molecular Biology of the Cell 16:649-664 (2005)). The actin cytoskeleton plays an integral role in a variety of cellular processes in plants such as tip growth, pollen tube growth. Actin filament arrays are constantly remodeled as the needs of cells change as well as during responses to biotic and abiotic stimuli. Several actin binding proteins have been implicated in remodeling cortical F-actin filaments in plants (Augustine et al, Plant Journal 54:863-875 (2008); Augustine et al., Plant Cell 23:3696-3710 (2011); Henty et al., Plant Cell 23:3711-3726 (2011)). It is demonstrated herein that the soybean actin depolymerizing factor gene promoter GM-ADF1 can, in fact, be used as a constitutive promoter to drive expression of transgenes in plants, and that such promoter can be isolated and used by one skilled in the art.

This invention concerns an isolated nucleic acid fragment comprising a constitutive actin-depolymerizing factor gene ADF1 promoter. This invention also concerns an isolated nucleic acid fragment comprising a promoter wherein said promoter consists essentially of the nucleotide sequence set forth in SEQ ID NO:1, or an isolated polynucleotide comprising a promoter wherein said promoter comprises the nucleotide sequence set forth in SEQ ID NOs: 1, 2, 3, 4, 5, 6, 7 or 43 or a functional fragment of SEQ ID NOs: 1, 2, 3, 4, 5, 6, 7 or 43.

The expression patterns of ADF1 gene and its promoter are set forth in Examples 1-7.

The promoter activity of the soybean genomic DNA fragment SEQ ID NO:1 upstream of the ADF1 protein coding sequence was assessed by linking the fragment to a green fluorescence reporter gene, ZS-GREEN1 (GFP) (Tsien, Annu. Rev. Biochem. 67:509-544 (1998); Matz et al., Nat. Biotechnol. 17:969-973 (1999)), transforming the promoter:GFP expression cassette into soybean, and analyzing GFP expression in various cell types of the transgenic plants (see Example 6 and 7). GFP expression was detected in most parts of the transgenic plants. These results indicated that the nucleic acid fragment contained a constitutive promoter.

It is clear from the disclosure set forth herein that one of ordinary skill in the art could perform the following procedure:

1) operably linking the nucleic acid fragment containing the ADF1 promoter sequence to a suitable reporter gene; there are a variety of reporter genes that are well known to those skilled in the art, including the bacterial GUS gene, the firefly luciferase gene, and the cyan, green, red, and yellow fluorescent protein genes; any gene for which an easy and reliable assay is available can serve as the reporter gene.

2) transforming a chimeric ADF1 promoter:reporter gene expression cassette into an appropriate plant for expression of the promoter. There are a variety of appropriate plants which can be used as a host for transformation that are well known to those skilled in the art, including the dicots, *Arabidopsis*, tobacco, soybean, oilseed rape, peanut, sunflower, safflower, cotton, tomato, potato, cocoa and the monocots, corn, wheat, rice, barley and palm.

3) testing for expression of the ADF1 promoter in various cell types of transgenic plant tissues, e.g., leaves, roots, flowers, seeds, transformed with the chimeric ADF1 promoter:reporter gene expression cassette by assaying for expression of the reporter gene product.

In another aspect, this invention concerns a recombinant DNA construct comprising at least one heterologous nucleic acid fragment operably linked to any promoter, or combination of promoter elements, of the present invention. Recombinant DNA constructs can be constructed by operably linking the nucleic acid fragment of the invention ADF1 promoter or a fragment that is substantially similar and functionally equivalent to any portion of the nucleotide sequence set forth in SEQ ID NOs: 1, 2, 3, 4, 5, 6, 7 or 43 to a heterologous nucleic acid fragment. Any heterologous nucleic acid fragment can be used to practice the invention. The selection will depend upon the desired application or phenotype to be achieved. The various nucleic acid sequences can be manipulated so as to provide for the nucleic acid sequences in the proper orientation. It is believed that various combinations of promoter elements as described herein may be useful in practicing the present invention.

In another aspect, this invention concerns a recombinant DNA construct comprising at least one acetolactate synthase (ALS) nucleic acid fragment operably linked to ADF1 promoter, or combination of promoter elements, of the present invention. The acetolactate synthase gene is involved in the biosynthesis of branched chain amino acids in plants and is the site of action of several herbicides including sulfonyl urea. Expression of a mutated acetolactate synthase gene encoding a protein that can no longer bind the herbicide will enable the transgenic plants to be resistant to the herbicide (U.S. Pat. No. 5,605,011, U.S. Pat. No. 5,378,824). The mutated acetolactate synthase gene is also widely used in plant transformation to select transgenic plants.

In another embodiment, this invention concerns host cells comprising either the recombinant DNA constructs of the invention as described herein or isolated polynucleotides of the invention as described herein. Examples of host cells which can be used to practice the invention include, but are not limited to, yeast, bacteria, and plants.

Plasmid vectors comprising the instant recombinant expression construct can be constructed. The choice of plasmid vector is dependent upon the method that will be used to transform host cells. The skilled artisan is well aware of the genetic elements that must be present on the plasmid vector in order to successfully transform, select and propagate host cells containing the chimeric gene.

Methods for transforming dicots, primarily by use of *Agrobacterium tumefaciens*, and obtaining transgenic plants have been published, among others, for cotton (U.S. Pat. No. 5,004,863, U.S. Pat. No. 5,159,135); soybean (U.S. Pat. No. 5,569,834, U.S. Pat. No. 5,416,011); *Brassica* (U.S. Pat. No. 5,463,174); peanut (Cheng et al., Plant Cell Rep. 15:653-657 (1996), McKently et al., Plant Cell Rep. 14:699-703 (1995)); *papaya* (Ling et al., Bio/technology 9:752-758 (1991)); and pea (Grant et al., Plant Cell Rep. 15:254-258 (1995)). For a review of other commonly used methods of plant transformation see Newell, C. A., Mol. Biotechnol. 16:53-65 (2000). One of these methods of transformation uses *Agrobacterium rhizogenes* (Tepfler, M. and Casse-Delbart, F., Microbiol. Sci. 4:24-28 (1987)). Transformation of soybeans using direct delivery of DNA has been published using PEG fusion (PCT Publication No. WO 92/17598), electroporation (Chowrira et al., Mol. Biotechnol. 3:17-23 (1995); Christou et al., Proc. Natl. Acad. Sci. U.S.A. 84:3962-3966 (1987)), microinjection, or particle bombardment (McCabe et al., Biotechnology 6:923-926 (1988); Christou et al., Plant Physiol. 87:671-674 (1988)).

There are a variety of methods for the regeneration of plants from plant tissues. The particular method of regeneration will depend on the starting plant tissue and the particular plant species to be regenerated. The regeneration, development and cultivation of plants from single plant protoplast transformants or from various transformed explants is well known in the art (Weissbach and Weissbach, Eds.; In Methods for Plant Molecular Biology; Academic Press, Inc.: San Diego, Calif., 1988). This regeneration and growth process typically includes the steps of selection of transformed cells, culturing those individualized cells through the usual stages of embryonic development or through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the present invention containing a desired polypeptide is cultivated using methods well known to one skilled in the art.

In addition to the above discussed procedures, practitioners are familiar with the standard resource materials which describe specific conditions and procedures for the construction, manipulation and isolation of macromolecules (e.g., DNA molecules, plasmids, etc.), generation of recombinant DNA fragments and recombinant expression constructs and the screening and isolating of clones, (see for example, Sambrook, J. et al., In Molecular Cloning: A Laboratory Manual; 2$^{nd}$ ed.; Cold Spring Harbor Laboratory Press: Cold Spring Harbor, N.Y., 1989; Maliga et al., In Methods in Plant Molecular Biology; Cold Spring Harbor Press, 1995; Birren et al., In Genome Analysis: Detecting Genes, 1; Cold Spring Harbor: New York, 1998; Birren et al., In Genome Analysis: Analyzing DNA, 2; Cold Spring Harbor: New York, 1998; Clark, Ed., In Plant Molecular Biology: A Laboratory Manual; Springer: New York, 1997).

The skilled artisan will also recognize that different independent transformation events will result in different levels and patterns of expression of the chimeric genes (Jones et al., EMBO J. 4:2411-2418 (1985); De Almeida et al., Mol. Gen. Genetics 218:78-86 (1989)). Thus, multiple events must be screened in order to obtain lines displaying the desired expression level and pattern. Such screening may be accomplished by Northern analysis of mRNA expression, Western analysis of protein expression, or phenotypic analysis. Also of interest are seeds obtained from transformed plants displaying the desired gene expression profile.

The level of activity of the ADF1 promoter is weaker than that of many known strong promoters, such as the CaMV 35S promoter (Atanassova et al., Plant Mol. Biol. 37:275-285 (1998); Battraw and Hall, Plant Mol. Biol. 15:527-538 (1990); Holtorf et al., Plant Mol. Biol. 29:637-646 (1995); Jefferson et al., EMBO J. 6:3901-3907 (1987); Wilmink et al., Plant Mol. Biol. 28:949-955 (1995)), the *Arabidopsis* ubiquitin extension protein promoters (Callis et al., J. Biol. Chem. 265(21):12486-12493 (1990)), a tomato ubiquitin gene promoter (Rollfinke et al., Gene 211:267-276 (1998)), a soybean heat shock protein promoter, and a maize H3 histone gene promoter (Atanassova et al., Plant Mol. Biol. 37:275-285 (1998)). Universal moderate expression of chimeric genes in most plant cells makes the ADF1 promoter of the instant invention especially useful when moderate constitutive expression of a target heterologous nucleic acid fragment is required.

Another general application of the ADF1 promoter of the invention is to construct chimeric genes that can be used to reduce expression of at least one heterologous nucleic acid fragment in a plant cell. To accomplish this, a chimeric gene designed for gene silencing of a heterologous nucleic acid fragment can be constructed by linking the fragment to the ADF1 promoter of the present invention. (See U.S. Pat. No. 5,231,020, and PCT Publication No. WO 99/53050 published on Oct. 21, 1999, PCT Publication No. WO 02/00904 published on Jan. 3, 2002, and PCT Publication No. WO 98/36083 published on Aug. 20, 1998, for methodology to block plant gene expression via cosuppression.) Alternatively, a chimeric gene designed to express antisense RNA for a heterologous nucleic acid fragment can be constructed by linking the fragment in reverse orientation to the ADF1 promoter of the present invention. (See U.S. Pat. No. 5,107,065 for methodology to block plant gene expression via antisense RNA.) Either the cosuppression or antisense chimeric gene can be introduced into plants via transformation. Transformants wherein expression of the heterologous nucleic acid fragment is decreased or eliminated are then selected.

This invention also concerns a method of altering (increasing or decreasing) the expression of at least one heterologous nucleic acid fragment in a plant cell which comprises:
(a) transforming a plant cell with the recombinant expression construct described herein;
(b) growing fertile mature plants from the transformed plant cell of step (a);
(c) selecting plants containing a transformed plant cell wherein the expression of the heterologous nucleic acid fragment is increased or decreased.

Transformation and selection can be accomplished using methods well-known to those skilled in the art including, but not limited to, the methods described herein.

Non-limiting examples of methods and compositions disclosed herein are as follows:
1. An isolated polynucleotide comprising:
   (a) a nucleotide sequence comprising the sequence set forth in SEQ ID NO:1, SEQ ID NO:2, SEQ ID NO:3, SEQ ID NO:4, SEQ ID NO:5, SEQ ID NO:6, or SEQ ID NO:7, or a functional fragment thereof; or,
   (b) a full-length complement of (a); or,
   (c) a nucleotide sequence comprising a sequence having at least 72% sequence identity, based on the Clustal V method of alignment with pairwise alignment default parameters (KTUPLE=2, GAP PENALTY=5, WINDOW=4 and DIAGONALS SAVED=4), when compared to the nucleotide sequence of (a);
   wherein said nucleotide sequence is a promoter.
2. The isolated polynucleotide of embodiment 1, wherein the polynucleotide is a constitutive promoter.
3. The isolated polynucleotide of embodiment 1, wherein the nucleotide sequence of (c) has at least 95% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:1.
3b. The isolated polynucleotide of embodiment 1, wherein the nucleotide sequence of (c) has at least 98.2% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:1.
4. The isolated polynucleotide of embodiment 3, wherein the nucleotide sequence is SEQ ID NO: 43.
5. An isolated polynucleotide comprising a promoter region of the ADF1 *Glycine max* gene as set forth in SEQ ID NO:1, wherein said promoter comprises a deletion at the 5'-terminus of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 100 6, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 11311, 1132, 1133, 1134, 1135, 1136, 1137, 1138, 1139, 1140, 1141, 1142, 1143, 1144, 1145, 1146, 1147, 1148, 1149, 1150, 11511, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 12312, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 13013, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354 or 1355 consecutive nucleotides, wherein the first nucleotide deleted is the cytosine nucleotide ['C'] at position 1 of SEQ ID NO:1.

5b. The isolated polynucleotide of embodiment 5, wherein the polynucleotide is a constitutive promoter.

6. A recombinant DNA construct comprising the isolated polynucleotide of any one of embodiments 1-5 operably linked to at least one heterologous nucleotide sequence.

7. A vector comprising the recombinant DNA construct of claim 6.

8. A cell comprising the recombinant DNA construct of claim 6.

9. The cell of claim 8, wherein the cell is a plant cell.

10. A transgenic plant having stably incorporated into its genome the recombinant DNA construct of claim 6.

11. The transgenic plant of claim 10 wherein said plant is a dicot plant.

12. The transgenic plant of claim 11 wherein the plant is soybean.

13. A transgenic seed produced by the transgenic plant of claim 10.

14. The recombinant DNA construct according to claim 6, wherein the at least one heterologous nucleotide sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.

15. The recombinant DNA construct according to claim 6, wherein the at least one heterologous nucleotide sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

16. A method of expressing a coding sequence or a functional RNA in a plant comprising:
    a) introducing the recombinant DNA construct of claim 6 into the plant, wherein the at least one heterologous nucleotide sequence comprises a coding sequence or a functional RNA;
    b) growing the plant of step a); and
    c) selecting a plant displaying expression of the coding sequence or the functional RNA of the recombinant DNA construct.

17. A method of transgenically altering a marketable plant trait, comprising:
    a) introducing a recombinant DNA construct of claim 6 into the plant;
    b) growing a fertile, mature plant resulting from step a); and
    c) selecting a plant expressing the at least one heterologous nucleotide sequence in at least one plant tissue based on the altered marketable trait.

18. The method of claim 17 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

19. A method for altering expression of at least one heterologous nucleic acid fragment in plant comprising:
    (a) transforming a plant cell with the recombinant DNA construct of claim 6;
    (b) growing fertile mature plants from transformed plant cell of step (a); and
    (c) selecting plants containing the transformed plant cell wherein the expression of the heterologous nucleic acid fragment is increased or decreased.

20. The method of claim 19 wherein the plant is a soybean plant.

21. A method for expressing a green fluorescent protein ZS-GREEN1 in a host cell comprising:
    (a) transforming a host cell with the recombinant DNA construct of claim 6; and,
    (b) growing the transformed host cell under conditions that are suitable for expression of the recombinant DNA construct, wherein expression of the recombinant DNA construct results in production of increased levels of ZS GREEN1 protein in the transformed host cell when compared to a corresponding non-transformed host cell.

22. A plant stably transformed with a recombinant DNA construct comprising a soybean constitutive promoter and a heterologous nucleic acid fragment operably linked to said constitutive promoter, wherein said constitutive promoter is a capable of controlling expression of said heterologous nucleic acid fragment in a plant cell, and further wherein said constitutive promoter comprises a fragment of SEQ ID NO:1.

EXAMPLES

The present invention is further defined in the following Examples, in which parts and percentages are by weight and degrees are Celsius, unless otherwise stated. Sequences of promoters, cDNA, adaptors, and primers listed in this invention all are in the 5' to 3' orientation unless described otherwise. Techniques in molecular biology were typically performed as described in Ausubel, F. M. et al., In Current Protocols in Molecular Biology; John Wiley and Sons: New York, 1990 or Sambrook, J. et al., In Molecular Cloning: A Laboratory Manual; $2^{nd}$ ed.; Cold Spring Harbor Laboratory Press: Cold Spring Harbor, N.Y., 1989 (hereinafter "Sambrook et al., 1989"). It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

Identification of Soybean Constitutive Promoter Candidate Genes

Soybean expression sequence tags (EST) were generated by sequencing randomly selected clones from cDNA libraries constructed from different soybean tissues. Multiple EST sequences could often be found with different lengths representing the different regions of the same soybean gene. If more EST sequences representing the same gene are frequently found from a tissue-specific cDNA library such as a flower library than from a leaf library, there is a possibility that the represented gene could be a flower preferred gene candidate. Likewise, if similar numbers of ESTs for the same gene were found in various libraries constructed from different tissues, the represented gene could be a constitutively expressed gene. Multiple EST sequences representing the same soybean gene were compiled electronically based on their overlapping sequence homology into a unique full length sequence representing the gene. These assembled unique gene sequences were accumulatively collected in Pioneer Hi-Bred Intl proprietary searchable databases.

To identify constitutive promoter candidate genes, searches were performed to look for gene sequences that were found at similar frequencies in leaf, root, flower, embryos, pod, and also in other tissues. One unique gene PSO315053 was identified in the search to be a moderate constitutive gene candidate. PSO315053 cDNA sequence (SEQ ID NO:17) as well as its putative translated protein sequence (SEQ ID NO:18) were used to search National Center for Biotechnology Information (NCBI) databases. Both PSO315053 nucleotide and amino acid sequences were found to have high homology to actin depolymerizing factor like genes discovered in several plant species including a soybean actin depolymerizing factor 2-like (LOCI 00813011) mRNA (SEQ ID NO:41; NCBI accession XM_003534986) and a partial but identical soybean uncharacterized LOC100305514 (LOC100305514) mRNA (SEQ ID NO:42; NCBI accession NM_001249519).

Solexa digital gene expression dual-tag-based mRNA profiling using the Illumina (Genome Analyzer) GA2 machine is a restriction enzyme site anchored tag-based technology, in this regard similar to Mass Parallel Signature Sequence transcript profiling technique (MPSS), but with two key differences (Morrissy et al., Genome Res. 19:1825-1835 (2009); Brenner et al., Proc. Natl. Acad. Sci. USA 97:1665-70 (2000)). Firstly, not one but two restriction enzymes were used, DpnII and NlaI, the combination of which increases gene representation and helps moderate expression variances. The aggregate occurrences of all the resulting sequence reads emanating from these DpnII and NlaI sites, with some repetitive tags removed computationally were used to determine the overall gene expression levels. Secondly, the tag read length used here is 21 nucleotides, giving the Solexa tag data higher gene match fidelity than the shorter 17-mers used in MPSS. Soybean mRNA global gene expression profiles are stored in a Pioneer proprietary database TDExpress (Tissue Development Expression Browser). Candidate genes with different expression patterns can be searched, retrieved, and further evaluated.

The actin depolymerizing factor gene PSO315053 (ADF1) corresponds to predicted gene Glyma15g13140.1 in the soybean genome, sequenced by the DOE-JGI Community Sequencing Program consortium (Schmutz J, et al., Nature 463:178-183 (2010)). The ADF1 expression profiles in twenty one tissues were retrieved from the TDExpress database using the gene ID Glyma15g13140.1 and presented as parts per ten millions (PP™) averages of three experimental repeats (FIG. 1). The ADF1 gene is expressed in all checked tissues at moderate levels with higher expressions detected in root, petiole, and stem to qualify as a candidate gene from which to clone a moderate constitutive promoter.

Example 2

Isolation of Soybean ADF1 Promoter

The PSO315053 cDNA sequence was BLAST searched against the soybean genome sequence database sequence (Schmutz J, et al., Nature 463:178-183 (2010) to identify corresponding genomic DNA. The ~1.5 kb sequence upstream of the PSO315053 start codon ATG was selected as ADF1 promoter to be amplified by PCR (polymerase chain reaction). The primers shown in SEQ ID NO:8 and 9 were then designed to amplify by PCR the putative full length 1567 bp ADF1 promoter from soybean genomic DNA (SEQ ID NO:1). SEQ ID NO:8 contains a recognition site for the restriction enzyme XmaI. SEQ ID NO:9 contains a recognition site for the restriction enzyme NcoI. The XmaI and NcoI sites were included for subsequent cloning.

PCR cycle conditions were 94° C. for 4 minutes; 35 cycles of 94° C. for 30 seconds, 60° C. for 1 minute, and 68° C. for 2 minutes; and a final 68° C. for 5 minutes before holding at 4° C. using the Platinum high fidelity Taq DNA polymerase (Invitrogen). The PCR reaction was resolved using agarose gel electrophoresis to identify the right size PCR product representing the ~1.6 Kb ADF1 promoter. The PCR fragment was first cloned into pCR2.1-TOPO vector by TA cloning (Invitrogen). Several clones containing the ~1.6 Kb DNA insert were sequenced and only one clone with the correct ADF1 promoter sequence was selected for further cloning. The plasmid DNA of the selected clone was digested with XmaI and NcoI restriction enzymes to move the ADF1 promoter upstream of the ZS-YELLOW N1 (YFP) fluorescent reporter gene in QC532 (FIG. 3A, SEQ ID NO:19). Construct QC532 contains the recombination sites AttL1 and AttL2 (SEQ ID NO:35 and 36) to qualify as a GATEWAY® cloning entry vector (Invitrogen). The 1567 bp sequence upstream of the ADF1 gene PSO315053 start codon ATG including the XmaI and NcoI sites is herein designated as soybean ADF1 promoter GM-ADF1 PRO of SEQ ID NO:1. Comparison of SEQ ID NO:1 to a soybean cDNA library revealed that SEQ ID NO: 1 comprised a 5' untranslated region (5'UTR) at its 3' end of at least 128 base pairs (SEQ ID NO:44). It is known to one of skilled in the art that a 5' UTR region can be altered (deletion or substitutions of bases) or replaced by an alternative 5'UTR while maintaining promoter activity.

Example 3

ADF1 Promoter COPY Number Analysis

Southern hybridization analysis was performed to examine whether additional copies or sequences with significant similarity to the ADF1 promoter exist in the soybean genome. Soybean 'Jack' wild type genomic DNA was digested with nine different restriction enzymes, BamHI, BglII, DraI, EcoRI, EcoRV, HindIII, MfeI, NdeI, and SpeI and distributed in a 0.7% agarose gel by electrophoresis. The DNA was blotted onto Nylon membrane and hybridized at 60° C. with digoxigenin labeled ADF1 promoter DNA probe in Easy-Hyb Southern hybridization solution, and then sequentially washed 10 minutes with 2×SSC/0.1% SDS at room temperature and 3×10 minutes at 65° C. with 0.1× SSC/0.1% SDS according to the protocol provided by the manufacturer (Roche Applied Science, Indianapolis, Ind.). The ADF1 promoter probe was labeled by PCR using the DIG DNA labeling kit (Roche Applied Science) with primers QC532-S5 (SEQ ID NO:15) and QC532-A (SEQ ID NO:10) and QC532 plasmid DNA (SEQ ID NO:19) as the template to make a 458 bp long probe covering the 3' half of the ADF1 promoter (FIG. 2B).

One of the nine restriction enzymes DraI would cut the 458 bp ADF1 promoter probe region twice into 40, 75, and 343 bp fragments so only the 3' ADF1 promoter fragment corresponding to the 343 bp probe fragment would be readily detected by Southern hybridization with the 458 bp ADF1 probe (FIG. 2B). The 40 bp might still be able to detect the 5' half of the ADF1 promoter but the 75 bp middle fragment would be too small to be retained on the Southern blot. Another enzyme MfeI would also cut the 458 bp ADF1 promoter probe region once into 240 and 218 by fragments so both the 5' and 3' ADF1 promoter fragments should be readily detected. None of the other seven restriction enzymes BamHI, BglII, EcoRI, EcoRV, HindIII, NdeI, and SpeI would cut the ADF1 promoter probe region. Therefore, only one band would be expected to be hybridized for each of the seven digestions if only one copy of ADF1 promoter sequence exists in soybean genome (FIG. 2B). The observation that only one band was detected in all digestions with the seven enzymes without recognition sites in the 458 bp ADF1 promoter region suggested that there is only one copy of the ADF1 promoter sequence in soybean genome (FIG. 2A). However, that observation that two equally strong bands were detected in DraI digestion and three bands were detected in MfeI digestion suggested that there might be another sequence similar to part of the 458 bp ADF1 promoter probe in soybean genome. The DIGVII molecular markers used on the Southern blot are 8576, 7427, 6106, 4899, 3639, 2799, 1953, 1882, 1515, 1482, 1164, and 992 bp.

Since the whole soybean genome sequence is now publically available (Schmutz J, et al., Nature 463:178-183 (2010)), the ADF1 promoter copy numbers can also be evaluated by searching the soybean genome with the 1567 bp promoter sequence (SEQ ID NO:1). Consistent with above Southern analysis, only one sequence Gm15: 9788827-9790327 matching the ADF1 promoter sequence 5-1567 bp with some mismatches in the middle was identified. The mismatches are probably due to the difference between the cultivars Williams 82 used in the soybean genome sequence project and Jack used in the ADF1 promoter cloning. The 5' end 6 bp and 3' end 6 bp of the 1567 bp ADF1 promoter may not match the genomic Gm15 sequence since they are artificially added XmaI and NcoI sites. In addition, a short sequence Gm09:1494836-1495068 shares many identical base pairs with the 3' half 1342-1567 of the ADF1 promoter and might correspond to the extra Southern bands detected in DraI and MfeI digestions (FIG. 2A).

FIG. 8 A-C shows a nucleotide sequence alignment of SEQ ID NO: 1, comprising the full length ADF1 promoter of the disclosure, and SEQ ID NO: 43, comprising a 1501 bp native soybean genomic DNA from Gm15:9788827 . . . 9790327 (Schmutz J. et al., Nature 463:178-183, 2010). As shown in FIG. 8-D, the ADF1 promoter of SEQ ID NO:1 is 98.2% identical to SEQ ID NO:43, based on the Clustal Vmethod of alignment with pairwise alignment default parameters (KTUPLE=2, GAP PENALTY=5, WINDOW=4 and DIAGONALS SAVED=4). Based on the data described in Examples 1-7, it is believed that SEQ ID NO:43 has promoter activity.

Example 4

ADF1:GFP Reporter Gene Constructs and Soybean Transformation

The ADF1 promoter was moved from QC532 and placed upstream of the green fluorescent reporter gene ZS-GREEN1 (GFP) in a GATEWAY® entry vector QC635 (SEQ ID NO:20; FIG. 3B). The ADF1:GFP cassette was moved into a GATEWAY® destination vector QC478i (SEQ ID NO:21) by LR Clonase® (Invitrogen) mediated DNA recombination between the attL1 and attL2 recombination sites (SEQ ID NO:35, and 36, respectively) in QC635 and the attR1-attR2 recombination sites (SEQ ID NO:37, and 38, respectively) in QC478i to make the final transformation construct QC644 (SEQ ID NO:22; FIG. 3B).

Since the GATEWAY® destination vector QC478i already contains a soybean transformation selectable marker gene SAMS:HRA, the resulting DNA construct QC644 has the ADF1:GFP gene expression cassette linked to the SAMS:HRA cassette (FIG. 3B). Two 21 bp recombination sites attB1 and attB2 (SEQ ID NO:39, and 40, respectively) were newly created recombination sites resulting from DNA recombination between attL1 and attR1, and between attL2 and attR2, respectively. The 6995 bp DNA fragment containing the linked ADF1:GFP and SAMS:HRA expression cassettes was isolated from plasmid QC644 (SEQ ID NO:22) with AscI digestion, separated from the vector backbone fragment by agarose gel electrophoresis, and purified from the gel with a DNA gel extraction kit (QIAGEN®, Valencia, Calif.). The purified DNA fragment was transformed to soybean cultivar Jack by the method of particle gun bombardment (Klein et al., Nature 327:70-73 (1987); U.S. Pat. No. 4,945,050) as described in detail below to study the ADF1 promoter activity in stably transformed soybean plants.

The same methodology as outlined above for the ADF1: GFP expression cassette construction and transformation can be used with other heterologous nucleic acid sequences encoding for example a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and salt resistance in plants.

Soybean somatic embryos from the Jack cultivar were induced as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, Calif.). To 50 µl of a 60 mg/ml 1.0 mm gold particle suspension were added (in order): 30 µl of 30 ng/µl QC589 DNA fragment ADF1:GFP+SAMS: HRA, 20 µl of 0.1 M spermidine, and 25 µl of 5 M $CaCl_2$. The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 100 ng/ml chlorsulfuron as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 100 ng/ml chlorsulfuron selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production.

Genomic DNA were extracted from somatic embryo samples and analyzed by quantitative PCR using a 7500 real time PCR system (Applied Biosystems, Foster City, Calif.) with gene-specific primers and FAM-labeled fluorescence probes to check copy numbers of both the SAMS:HRA expression cassette and the ADF1:GFP expression cassette. The qPCR analysis was done in duplex reactions with a heat shock protein (HSP) gene as the endogenous controls and a transgenic DNA sample with a known single copy of SAMS:HRA or GFP transgene as the calibrator. The endogenous control HSP probe was labeled with VIC and the target gene SAMS:HRA or GFP probe was labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

The primers and probes used in the qPCR analysis are listed below.
SAMS forward primer: SEQ ID NO:26
FAM labeled ALS probe: SEQ ID NO:27
ALS reverse primer: SEQ ID NO:28
GFP forward primer: SEQ ID N0:29
FAM labeled GFP probe: SEQ ID NO:30
GFP reverse primer: SEQ ID NO:31
HSP forward primer: SEQ ID NO:32
VIC labeled HSP probe: SEQ ID NO:33
HSP reverse primer: SEQ ID NO:34

Only transgenic soybean events containing 1 or 2 copies of both the SAMS:HRA expression cassette and the ADF1:GFP expression cassette were selected for further gene expression evaluation and seed production (see Table 1). Events negative for GFP qPCR or with more than 2 copies for the SAMS:HRA qPCR were not further followed. GFP expressions are described in detail in EXAMPLE 7 and are also summarized in Table 1.

TABLE 1

Relative transgene copy numbers and YFP expression of ADF1:GFP transgenic plants

| Event ID | GFP expression | GFP qPCR | SAMS:HRA qPCR |
|---|---|---|---|
| 8133.8.5 | + | 0.9 | 0.7 |
| 8133.8.7 | + | 0.8 | 0.3 |
| 8133.8.8 | + | 1.8 | 0.9 |
| 8133.8.9 | + | 1.6 | 1.9 |
| 8133.8.10 | + | 1.1 | 0.7 |
| 8133.8.13 | + | 1.7 | 1.2 |
| 8133.8.15 | + | 1.8 | 0.6 |
| 8133.8.17 | + | 1.7 | 1.7 |
| 8133.9.2 | + | 1.9 | 1.5 |
| 8133.9.3 | + | 0.5 | 0.5 |
| 8133.9.4 | + | 2.0 | 0.7 |
| 8133.9.7 | + | 1.8 | 1.6 |
| 8133.9.8 | + | 0.8 | 0.9 |
| 8133.9.15 | + | 1.8 | 1.5 |
| 8133.9.18 | + | 1.8 | 1.7 |
| 8133.9.19 | + | 1.6 | 1.7 |
| 8133.9.27 | + | 0.8 | 0.7 |
| 8133.9.31 | + | 2.0 | 1.4 |
| 8133.9.32 | + | 1.7 | 1.5 |
| 8133.9.34 | + | 2.0 | 2.2 |
| 8133.9.39 | + | 1.5 | 1.3 |

Example 5

Construction of ADF1 Promoter Deletion Constructs

To define the transcriptional elements controlling the ADF1 promoter activity, the 1559 bp fragment (SEQ ID NO:2) and five 5' unidirectional deletion fragments 1243 bp, 985 bp, 770 bp, 458 bp, and 212 bp in length corresponding to SEQ ID NO:3, 4, 5, 6, and 7, respectively, were made by PCR amplification from the full length soybean ADF1 promoter contained in the original construct QC532 (FIG. 3A). The same antisense primer QC532-A (SEQ ID NO:10) was used in the amplification by PCR of all the six ADF1 promoter fragments (SEQ ID NOs: 2, 3, 4, 5, 6, and 7) by pairing with different sense primers SEQ ID NOs:11, 12, 13, 14, 15, and 16, respectively. Each of the PCR amplified promoter DNA fragments was cloned into the GATEWAY® cloning ready TA cloning vector pCR8/GW/TOPO (Invitrogen) and clones with the correct orientation, relative to the GATEWAY® recombination sites attL1 and attL2, were selected by sequence confirmation. The map of construct QC532-1 (SEQ ID NO:23) containing the near full length ADF1 promoter fragment (SEQ ID NO:2) is shown in FIG. 4A. The maps of constructs QC532-2, 3, 4, 5, and 6 containing the truncated ADF1 promoter fragments SEQ ID NOs: 3, 4, 5, 6, and 7 are similar to QC532-1 map and are not showed. The promoter fragment in the right orientation was subsequently cloned into a GATEWAY® destination vector QC330 (SEQ ID NO:24) by GATEWAY® LR Clonase® reaction (Invitrogen) to place the promoter fragment in front of the reporter gene YFP (see the example map QC532-1Y in FIG. 4B and SEQ ID NO:25). A 21 bp GATEWAY® recombination site attB2 (SEQ ID NO:40) was inserted between the promoter and the YFP reporter gene coding region as a result of the GATEWAY® cloning process. The maps and sequences of constructs QC532-2Y, 3Y, 4Y, 5Y, and 6Y containing the ADF1 promoter fragments SEQ ID NOs: 3, 4, 5, 6, and 7 are similar to QC532-1Y map and sequence and are not showed.

The ADF1:YFP promoter deletion constructs were delivered into germinating soybean cotyledons by gene gun bombardment for transient gene expression study. A similar construct pZSL90 with a constitutive promoter SCP1 (U.S. Pat. No. 6,555,673) driving YFP expression and a promoterless construct QC330-Y were used as positive and negative controls, respectively (FIG. 4C). The six ADF1 promoter fragments analyzed are schematically described in FIG. 5.

Example 6

Transient Expression Analysis of ADF1:YFP Constructs

The constructs containing the full length and truncated ADF1 promoter fragments (QC532-1Y, 2Y, 3Y, 4Y, 5Y, and 6Y) were tested by transiently expressing the ZS-YELLOW1 N1 (YFP) reporter gene in germinating soybean cotyledons. Soybean seeds were rinsed with 10% TWEEN® 20 in sterile water, surface sterilized with 70% ethanol for 2 minutes and then by 6% sodium hypochloride for 15 minutes. After rinsing the seeds were placed on wet filter paper in Petri dish to germinate for 4-6 days under light at 26° C. Green cotyledons were excised and placed inner side up on a 0.7% agar plate containing Murashige and Skoog media for particle gun bombardment. The DNA and gold particle mixtures were prepared similarly as described in EXAMPLE 4 except with more DNA (100 ng/µl). The bombardments were also carried out under similar parameters as described in EXAMPLE 4. YFP expression was checked under a Leica MZFLIII stereo microscope equipped with UV light source and appropriate light filters (Leica Microsystems Inc., Bannockburn, Ill.) and pictures were taken approximately 24 hours after bombardment with 8× magnification using a Leica DFC500 camera with settings as 0.60 gamma, 1.0 gain, 0.70 saturation, 61 color hue, 56 color saturation, and 0.51 second exposure.

The full length ADF1 promoter construct QC532-1Y had comparable yellow fluorescence signals in transient expression assay as the positive control pZSL90 by showing small yellow dots in red background. Each dot represented a single cotyledon cell which appeared larger if the fluorescence signal was strong or smaller if the fluorescence signal was weak even under the same magnification (FIG. 6). QC532-2Y had some fewer yellow dots probably due to the fluctuation of DNA actually delivered to the cotyledons in different bombardments. The attB2 site inserted between the ADF1 promoter and YFP gene did not seem to interfere with promoter activity and reporter gene expression for the deletion constructs. The deletion constructs QC532-2Y, QC532-3Y, QC532-4Y and QC532-5Y showed a slight reduction in yellow fluorescence signals (yellow dots in FIG. 6) comparable to the 1559 bp ADF1 promoter construct QC532-1Y (FIG. 6), indicating that these promoter fragments are all functional at similar strength. The shortest deletion construct QC532-6Y also showed yellow dots, though smaller and very faint, suggesting that as short as 212 bp ADF1 promoter sequence upstream of the start codon ATG was long enough for the minimal expression of a reporter gene.

The data clearly indicates that all deletion constructs are functional as a constitutive promoter and as such SEQ ID NO: 2, 3, 5, 6, 7 are all functional fragments of SEQ ID NO:1.

Example 7

ADF1:GFP Expression in Stable Transgenic Soybean Plants

The stable expression of the fluorescent protein reporter gene ZS-GREEN1 (GFP) driven by the full length ADF1 promoter (SEQ ID NO:1) in transgenic soybean plants is shown in FIG. 7A-P.

ZS-GREEN1 (GFP) gene expression was tested at different stages of transgenic plant development for yellow fluorescence emission under a Leica MZFLIII stereo microscope equipped with appropriate fluorescent light filters. Green fluorescence was detectable in globular and young heart stage somatic embryos during the suspension culture period of soybean transformation (FIG. 7A, B). Moderate GFP expression was continuously detected in differentiating somatic embryos placed on solid medium and then throughout later stages until fully developed drying down somatic embryos (FIG. 7C, D). The negative section of a positive embryo cluster emitted weak red color due to auto fluorescence from the chlorophyll contained in soybean green tissues including embryos. The reddish green fluorescence indicated that the GFP expression was moderate since everything would be bright green if the GFP gene was driven by a strong constitutive promoter. When transgenic plants regenerated, GFP expression was detected in most tissues checked, such as flower, leaf, stem, root, pod, and seed (FIG. 7E-P). Negative controls for most tissue types displayed in FIG. 7 are not shown, but any green tissue such as leaf or stem negative for GFP expression would look red and any white tissue such as root and petal would look dull yellowish under the GFP fluorescent light filter.

A soybean flower consists of five sepals, five petals including one standard large upper petal, two large side petals, and two small lower petals called kneel to enclose ten stamens and one pistil. The pistil consists of a stigma, a style, and an ovary in which there are 2-4 ovules. A stamen consists of a filament, and an anther on its tip. The filaments of nine of the stamens are fused and elevated as a single structure with a posterior stamen remaining separate. Pollen grains reside inside anther chambers and are released during pollination the day before the fully opening of the flower. Fluorescence signals were detected in the sepals and petals of both flower buds and open flowers and also in the stamens and pistil inside the flower especially in anthers and the inner lining of the pistil and also weakly in ovules (FIG. 7E-H).

Green fluorescence was detected weakly in fully developed leaf and stem or leaf petiole surface (FIG. 7I, J), but strongly in root (FIG. 7M) of T0 adult plant. Strong fluorescence signals were primarily detected in the vascular bundles especially the phloem of stem, leaf petiole, and root as clearly showed in their cross sections (FIG. 7K-M).

Weak fluorescence signals were detected in developing seeds and pod coats of the ADF1:GFP transgenic plants from young R3 pod of ~5 mm long, to full R4 pod of ~20 mm long, until elongated pods filled with R5, R6 seeds (FIG. 7N-P). Strong fluorescence signals were concentrated in the funiculus tissue or ovule stalk and its extending pod coat edge and in seed coat close to the funiculus. The seed and pod development stages were defined according to descriptions in Fehr and Caviness, IWSRBC 80:1-12 (1977).

In conclusion, ADF1:GFP expression was detected moderately in most tissues throughout transgenic plant development indicating that the soybean ADF1 promoter is a moderate constitutive promoter.

What is claimed is:

1. A recombinant DNA construct comprising a nucleotide sequence comprising:
   (a) the sequence set forth in SEQ ID NO: 1, SEQ ID NO: 2, SEQ ID NO: 3, SEQ ID NO: 4, SEQ ID NO: 5, SEQ ID NO: 6, SEQ ID NO: 43, or SEQ ID NO: 7; or
   (b) a full-length complement of the sequence of (a);
   wherein said nucleotide sequence is operably to at least one heterologous nucleotide sequence to be expressed.

2. A vector comprising the recombinant DNA construct of claim 1.

3. A cell comprising the recombinant DNA construct of claim 1.

4. The cell of claim 3, wherein the cell is a plant cell.

5. A transgenic plant having stably incorporated into its genome the recombinant DNA construct of claim 1.

6. The transgenic plant of claim 5 wherein said plant is a dicot plant.

7. The transgenic plant of claim 6 wherein the plant is soybean.

8. A transgenic seed produced by the transgenic plant of claim 5, wherein the transgenic seed has stably incorporated into its genome the recombinant DNA construct of claim 1.

9. The recombinant DNA construct according to claim 1, wherein the at least one heterologous nucleotide sequence comprises a nucleotide sequence selected from the group consisting of: a reporter nucleotide sequence, a selection marker nucleotide sequence, a nucleotide sequence conferring disease resistance, a nucleotide sequence conferring herbicide resistance, a nucleotide sequence conferring insect resistance, a nucleotide sequence involved in carbohydrate metabolism, a nucleotide sequence involved in fatty acid metabolism, a nucleotide sequence invoked in amino acid metabolism, a nucleotide sequence involved in plant development, a nucleotide sequence involved in plant growth regulation, a nucleotide sequence involved in yield improvement, a nucleotide sequence involved in drought resistance, a nucleotide sequence involved in cold resistance, a nucleo- tide sequence involved in heat resistance, and a nucleotide sequence involved in salt resistance in plants.

10. The recombinant DNA construct according to claim 1, wherein the at least one heterologous nucleotide sequence encodes a protein selected from the group consisting of: a reporter protein, a selection marker, a protein conferring disease resistance, a protein conferring herbicide resistance, a protein conferring insect resistance, a protein involved in carbohydrate metabolism, a protein involved in fatty acid metabolism, a protein involved in amino acid metabolism, a protein involved in plant development, a protein involved in plant growth regulation, a protein involved in yield improvement, a protein involved in drought resistance, a protein involved in cold resistance, a protein involved in heat resistance, and a protein involved in salt resistance in plants.

11. A method of expressing a coding sequence or a functional RNA in a plant comprising:
   a) introducing the recombinant DNA construct of claim 1 into the plant, wherein the at least one heterologous nucleotide sequence comprises a coding sequence or a functional RNA;
   b) growing the plant of step a); and
   c) selecting a plant displaying expression of the coding sequence or the functional RNA of the recombinant DNA construct.

12. A method of transgenically altering a marketable plant trait, the method comprising:
   a) introducing the recombinant DNA construct of claim 1 into the plant, wherein the at least one heterologous nucleotide sequence to be expressed confers the altered marketable trait;
   b) growing a fertile, mature plant resulting from step a); and
   c) selecting a plant comprising the at least one heterologous nucleotide sequence in at least one plant tissue for the altered marketable trait.

13. The method of claim 12 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

14. A method for altering expression of at least one heterologous nucleic acid fragment in plant comprising:
   (a) transforming a plant cell with the recombinant DNA construct of claim 1;
   (b) growing fertile mature plants from transformed plant cell of step (a); and
   (c) selecting plants containing the transformed plant cell wherein the expression of the heterologous nucleic acid fragment is increased or decreased.

15. The method of claim 14 wherein the plant is a soybean plant.

16. A method for expressing a green fluorescent protein ZS-GREEN1 in a host cell, the method comprising:
   (a) transforming a host cell with the recombinant DNA construct of claim 1, wherein said at least one heterologous nucleotide sequence to be expressed encodes the ZS-GREEN1 fluorescent protein, and
   (b) growing the transformed host cell under conditions that are suitable for expression of the recombinant DNA construct, wherein expression of the recombinant DNA construct results in production of increased levels of the ZS-GREEN1 protein in the transformed host cell when compared to a non-transformed host cell.

17. A plant comprising a recombinant DNA construct comprising a soybean constitutive promoter operably linked a heterologous nucleic acid, wherein said constitutive promoter comprises a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, and SEQ ID NO: 43.

* * * * *